(12) United States Patent
Warthoe

(10) Patent No.: US 7,473,551 B2
(45) Date of Patent: Jan. 6, 2009

(54) NANO-MECHANIC MICROSENSORS AND METHODS FOR DETECTING TARGET ANALYTES

(75) Inventor: Peter Warthoe, Copenhagen (DK)

(73) Assignee: Atonomics A/S, Copenhagen (DK)

( * ) Notice: Subject to any disclaimer, the term of this patent is extended or adjusted under 35 U.S.C. 154(b) by 443 days.

(21) Appl. No.: 11/134,821

(22) Filed: May 20, 2005

(65) Prior Publication Data

US 2006/0024813 A1    Feb. 2, 2006

(30) Foreign Application Priority Data

May 21, 2004   (DK)   .......................... PA 2004 00802

(51) Int. Cl.
*G01N 33/543* (2006.01)

(52) U.S. Cl. ................ 435/287.2; 310/311; 310/313 R; 310/313 B; 310/340; 435/5; 435/6; 435/7.2; 435/7.21; 435/7.32; 435/287.9; 436/513; 436/514; 436/515; 436/524; 436/527; 436/518

(58) Field of Classification Search ....................... None
See application file for complete search history.

(56) References Cited

U.S. PATENT DOCUMENTS

| 4,236,893 | A | 12/1980 | Rice |
| 4,242,096 | A | 12/1980 | Oliveira et al. |
| 4,314,821 | A | 2/1982 | Rice |
| 4,469,863 | A | 9/1984 | Ts'o et al. |
| 4,683,195 | A | 7/1987 | Mullis |
| 4,683,202 | A | 7/1987 | Mullis |
| 5,034,506 | A | 7/1991 | Summerton et al. |
| 5,061,336 | A | 10/1991 | Soane |
| 5,071,531 | A | 12/1991 | Soane |
| 5,110,745 | A | 5/1992 | Kricka et al. |
| 5,124,246 | A | 6/1992 | Urdea et al. |
| 5,126,022 | A | 6/1992 | Soane et al. |
| 5,130,257 | A | 7/1992 | Baer et al. |
| 5,135,627 | A | 8/1992 | Soane |
| 5,185,243 | A | 2/1993 | Ullman et al. |
| 5,216,141 | A | 6/1993 | Benner |
| 5,235,033 | A | 8/1993 | Summerton et al. |
| 5,242,828 | A | 9/1993 | Bergström et al. |

(Continued)

FOREIGN PATENT DOCUMENTS

DE    199 16 638 A1    11/2000

(Continued)

OTHER PUBLICATIONS

Barie, N., et al., "Covalent bound sensing layers on surface acoustic wave (SAW) biosensors," *Biosens. Bioelectron.* 16(9-12):979-987 (Dec. 2001).

(Continued)

*Primary Examiner*—Christopher L Chin
(74) *Attorney, Agent, or Firm*—The Nath Law Group; Gary M. Nath; Tanya E. Harkins

(57) ABSTRACT

The present invention relates generally to methods and compositions for analyzing test samples containing target analytes including proteins and nucleic acids. The invention uses a surface acoustic wave sensor in combination with a hydrogel to obtain an ultra sensitive non-fluorescent detection system.

27 Claims, 28 Drawing Sheets

U.S. PATENT DOCUMENTS

| | | | |
|---|---|---|---|
| 5,283,037 A | 2/1994 | Baer et al. | |
| 5,296,375 A | 3/1994 | Kricka et al. | |
| 5,304,487 A | 4/1994 | Wilding et al. | |
| 5,306,644 A | 4/1994 | Myerholtz et al. | |
| 5,359,100 A | 10/1994 | Urdea et al. | |
| 5,386,023 A | 1/1995 | Sanghri et al. | |
| 5,478,756 A | 12/1995 | Gizeli et al. | |
| 5,486,335 A | 1/1996 | Wilding et al. | |
| 5,492,840 A * | 2/1996 | Malmqvist et al. | 436/518 |
| 5,498,392 A | 3/1996 | Wilding et al. | |
| 5,545,730 A | 8/1996 | Urdea et al. | |
| 5,569,364 A | 10/1996 | Hooper et al. | |
| 5,571,670 A | 11/1996 | Urdea et al. | |
| 5,573,907 A | 11/1996 | Carrino et al. | |
| 5,580,731 A | 12/1996 | Chang et al. | |
| 5,585,069 A | 12/1996 | Zanzucchi et al. | |
| 5,587,128 A | 12/1996 | Wilding et al. | |
| 5,591,584 A | 1/1997 | Chang et al. | |
| 5,593,838 A | 1/1997 | Zanzucchi et al. | |
| 5,594,117 A | 1/1997 | Urdea et al. | |
| 5,594,118 A | 1/1997 | Urdea et al. | |
| 5,597,909 A | 1/1997 | Urdea et al. | |
| 5,602,240 A | 2/1997 | DeMesmaeker et al. | |
| 5,603,351 A | 2/1997 | Cherukuri et al. | |
| 5,616,464 A | 4/1997 | Albagli et al. | |
| 5,624,802 A | 4/1997 | Urdea et al. | |
| 5,631,337 A | 5/1997 | Sassi et al. | |
| 5,632,876 A | 5/1997 | Zanzucchi et al. | |
| 5,635,352 A | 6/1997 | Urdea et al. | |
| 5,635,358 A | 6/1997 | Wilding et al. | |
| 5,637,469 A | 6/1997 | Wilding et al. | |
| 5,637,684 A | 6/1997 | Cook et al. | |
| 5,643,738 A | 7/1997 | Zanzucchi et al. | |
| 5,644,048 A | 7/1997 | Yau | |
| 5,681,484 A | 10/1997 | Zanzucchi et al. | |
| 5,681,697 A | 10/1997 | Urdea et al. | |
| 5,681,702 A | 10/1997 | Collins et al. | |
| 5,726,026 A | 3/1998 | Wilding et al. | |
| 5,747,169 A | 5/1998 | Fan et al. | |
| 5,750,015 A | 5/1998 | Soane et al. | |
| 5,755,942 A | 5/1998 | Zanzucchi et al. | |
| 5,767,259 A | 6/1998 | Albagli et al. | |
| 5,770,029 A | 6/1998 | Nelson et al. | |
| 5,846,708 A | 12/1998 | Hollis et al. | |
| 6,670,461 B1 | 12/2003 | Wengel et al. | |
| 6,960,617 B2 * | 11/2005 | Omidian et al. | 521/102 |
| 6,974,707 B1 * | 12/2005 | Barie et al. | 436/529 |
| 2002/0068157 A1 | 6/2002 | Wischerhoff | |

FOREIGN PATENT DOCUMENTS

| | | |
|---|---|---|
| EP | 0 320 308 B1 | 6/1989 |
| EP | 0 336 731 B1 | 10/1989 |
| EP | 0 439 182 B1 | 7/1991 |
| EP | 0 637 996 B1 | 2/1995 |
| EP | 0 637 998 B1 | 2/1995 |
| WO | WO 89/09835 A1 | 10/1989 |
| WO | WO 89/12696 A1 | 12/1989 |
| WO | WO 90/01069 A1 | 2/1990 |
| WO | WO 91/07087 A1 | 5/1991 |
| WO | WO 92/01931 A1 | 7/1991 |
| WO | WO 96/15450 A1 | 5/1996 |
| WO | WO 96/39252 A1 | 12/1996 |
| WO | WO 96/39260 A1 | 12/1996 |
| WO | WO 97/16561 A1 | 5/1997 |
| WO | WO 97/16835 A1 | 5/1997 |
| WO | WO 97/27324 A1 | 7/1997 |
| WO | WO 97/43629 A1 | 11/1997 |
| WO | WO 98/13683 A1 | 4/1998 |
| WO | WO 03/019981 A3 | 3/2003 |

OTHER PUBLICATIONS

Beaucage, S., et al., "The functionalization of oligonucleotides via phosphoramidite derivatives," *Tetrahedron* 49(10):1925-1963 (Mar. 1993).

Brill, W., et al., "Synthesis of oligodeoxynucleoside phosphorodithioates via thioamidites," *J. Am. Chem. Soc.* 111(6):2321-2322 (Mar. 1989).

Carlsson, C., et al., "Screening for genetic mutations," *Nature* 380(6571):207 (Mar. 1996).

Chaki, N., et al., "Self-assembled monlayers as a tunable platform for biosensor applications," *Biosens. Bioelect.* 17:1-12 (2002).

De Mesmaeker, A., et al., "Comparison of rigid and flexible backbones in antisense oligonucleotides," *Bioorg. Med. Chem. Lett.* 4(3):395-398 (Feb. 1994).

Dempcy, R., et al., "Synthesis of a thymidyl pentamer of deoxyribonucleoic guanidine and binding studies with DNA homopolynucleotides," *Proc. Natl. Acad. Sci. USA* 92(13):6097-6101 (Jun. 1995).

Egholm, M., "PNA hybridizes to complementary oligonucleotides obeying the Watson-Crick hydrogen-bonding rules," *Nature* 365(6446):566-568 (Oct. 1993).

Egholm, M., et al., "Peptide nucleic acids (PNA). Oligonucleotide analogs with an achiral peptide backbone," *J. Am. Chem. Soc.* 114(5):1895 (Feb. 1992).

Gao, X., et al., "Unusual conformation of a 3'-thioformacetal linkage in a DNA duplex," *J. Biomol. NMR* 4(1):17-34 (Jan. 1994).

Holding, C., et al., "Diagnosis of β-thalassaemia by DNA amplification in single blastomeres from mouse preimplantation embryos," *Lancet* 2(8662):532-535 (Sep. 1989).

Horn, T., et al., "Oligonucleotides with alternating anionic and cationic phosphoramidate linkages: Synthesis and hybridization of stereouniform isomers," *Tetrahedron Lett.* 37(6):743 (Feb. 1996).

Jenkins, G., et al., "The biosynthesis of carbocyclic nucleosides," *Chem. Soc. Rev.* 3:169-176 (1995).

Josse, F., et al., "Guided shear horizontal surface acoustic wave sensors for chemical and biochemical detection in liquids," *Anal. Chem.* 73(24):5937-5944 (Dec. 2001).

Letsinger, R., et al., "Cationic oligonucleotides," *J. Am. Chem. Soc.* 110(13):4470-4471 (Jun. 1988).

Letsinger, R., et al., "Effects of pendant groups at phosphorus on binding properties of d-ApA analogues," *Nucleic Acids Res.* 14(8):3487-3499 (Apr. 1986).

Mag, M., et al., "Synthesis and selective cleavage of an oligodeoxynucleotide containing a bridged internucleotide 5'-phosphorothioate linkage," *Nucleic Acids Res.* 19(7):1437-1441 (Apr. 1991).

Meier, C., et al., "Peptide nucleic acids (PNAs)—unusual properties of nonionic oligonucleotide analogues," *Angew. Chem. Int. Ed. Eng.* 31(8):1008-1010 (Aug. 1992).

Nickerson, D., et al., "Automated DNA diagnostics using an ELISA-based oligonucletide ligation assay," *Proc. Natl. Acad. Sci. USA* 87(22):8923-8927 (Nov. 1990).

Pyun, J., et al., "Development of a biosensor for *E. coli* based on a flexural plante wave (FPW) tranducer," *Biosens. Bioelectron.* 13(7-8):839-845 (Oct. 1998).

Qian, X., et al., "Array of self-assembled monolayers for studying inhibition of bacterial adhesion," *Anal. Chem.* 74(8):1805-1810 (Apr. 2002).

Rapp, M., et al., "Modification of commercially available LOW-LOSS SAW devices towards an immunosensor for in situ measurements in water," *1995 IEEE Int. Ultrasonics Symp.*, Seattle, WA (Nov. 7-10, 1995).

Sidransky, D., et al., "Identification of p53 gene mutations in bladder cancers and urine samples," *Science* 252(5006):706-709 (May 1991).

Sprinzl, M., et al., "Enzymatic incorporation of ATP and CTP analogues into the 3' end of tRNA," *Eur. J. Biochem.* 81(3):579-589 (Dec. 1977).

Stubbs, D., et al., "Gas phase activity of anti-FITC antibodies immobilized on a surface acoustic wave resonator device," *Biosens. Bioelectron.* 17(6-7):471-477 (Jun. 2002).

Tijssen, P., "Overview of principles of hybridization and the strategy of nucleic acid assays," in *Laboratory Techniques in Biochemistry and Molecular Biology—Hybridization with Nucleic Acid Probes*, vol. 24, P. Tijssen (ed.), Elsevier Co. Ltd.: Amsterdam, NL (1993).

Van Den Hul, H.J., et al., "Well-characterized monodisperse latexes," *J. Colloid Interface Sci.* 28(2):336-337 (Oct. 1968).

von Kiedrowski, G., et al., "Parabolic growth of a self-replicating hexadeoxynycleotide bearing a 3'-5'-phosphoramidate linkage," *Angew. Chem. Int. Ed. Engl.* 30(4):423-426 (Apr. 1991).

Welsch, W., et al., "Development of a surface acoustic wave immunosensor," *Anal. Chem.* 68(13):2000-2004 (Jul. 1996).

* cited by examiner

SAW chip (2x2mm)   Unit (um)

SEQUENCE LISTING

```
<160> NUMBER OF SEQ ID NOS: 1

<210> SEQ ID NO 1
<211> LENGTH: 20
<212> TYPE: DNA
<213> ORGANISM: Homo sapiens

<400> SEQUENCE: 1
atataccgaa gaggcgcaga                                                     20
```

NANO-MECHANIC MICROSENSORS AND METHODS FOR DETECTING TARGET ANALYTES

CROSS REFERENCE TO RELATED APPLICATIONS

This application claims the benefit under 35 U.S.C. 365(c) of PA 2004 00802, filed May 21, 2004, which is expressly hereby incorporated by reference.

FIELD OF THE INVENTION

The present invention generally relates to a surface acoustic wave sensor coated with a hydrogel containing a molecular recognition component. The microsensors find application in numerous chemical, environmental and medical applications.

BACKGROUND OF THE INVENTION

Sensitive detection of analytes, such as biological analytes, continues to be a significant challenge in analytical detection methods. Frequently, detection methods require processing of multiple samples. In addition, modification of analyte molecules is often required prior to their detection. Further, analytical detection methods should be easy, rapid, and reproducible. This is particularly important when highly specialized methods and reagents, such as diagnostic methods, are unavailable.

Conventional bioanalytical methods in particular have several deficiencies. For example, hybridization of nucleic acid molecules is generally detected by autoradiography or phosphor image analysis when the hybridization probe contains a radioactive label or by densitometer when the hybridization probe contains a label, such as biotin or digoxin. The label can in turn be recognized by an enzyme-coupled antibody or ligand. Most modern biomolecule detection methods require modification of the molecule e.g. DNA or RNA or protein, making current detection methods expensive and labor intensive.

Acoustic wave sensor technology has shown broad application in detecting materials. Acoustic wave sensors detect materials by generating and observing an acoustic wave. As the acoustic wave propagates through or on the surface of the material, any changes to the characteristics of the propagation path affect the velocity and/or amplitude of the wave. The amplitude, frequency, and/or phase characteristics of the sensor can be measured and correlated to a corresponding physical quantity.

Several different types of acoustic wave devices have been developed, but all have only limited success in measuring water soluble or biological samples. Bulk acoustic waves (BAW) propagate through a medium. The most commonly used BAW devices are the thickness shear mode (TSM) resonator and the shear-horizontal acoustic plate mode (SH-APM) sensor. Conversely, waves that propagate on the surface of the substrate are known as surface waves. The most widely used surface wave devices are the surface acoustic wave sensor and the shear-horizontal surface acoustic wave (SH-SAW) sensor, also known as the surface transverse wave (STW) sensor. All acoustic wave sensors will function in gaseous or vacuum environments, but very few of them will operate efficiently when they are in contact with liquids.

Of the known acoustic sensors for liquid sensing, the Love wave sensor, a special class of the shear-horizontal SAW, has the highest sensitivity. To make a Love wave sensor, a dielectric waveguide coating is placed on a SH-SAW device such that the energy of the shear horizontal waves is focused in that coating. A biorecognition coating is then placed on the waveguide coating, forming the complete biosensor. Successful detection of anti-goat IgG in the concentration range of ng/ml using a 110 MHz YZ-cut SH-SAW with a polymer Love wave guide coating has been achieved [E. Gizeli et al. 1997. "Antibody Binding to a Functionalized Supported Lipid Layer: A Direct Acoustic Immunosensor," Anal Chem, Vol. 69:4808-4813.].

A comparison between different SAW sensors has recently been described (Biomolecular Sensors, Eds. Electra Gizeli and Christoffer R. Lowe (2002). They describes a 124 MHz Love wave sensor have a sensitivity of 1.92 mg/cm2. The use of SAW sensors for detection of biological compounds been reported in, for example, U.S. Pat. No. 5,478,756, WO9201931 and WO03019981, each of which is incorporated herein by reference in its entirety.

Conventional SAW devices are a poor choice for liquid detection, as the vertical component of the propagating wave is suppressed by the liquid-air barrier. One acoustic wave sensor that function in liquids is a shear-horizontal SAW sensor. If the cut of the piezoelectric crystal material is rotated appropriately, waves propagate horizontally and parallel to a liquid surface. This dramatically reduces loss when liquids come into contact with the propagating medium, allowing the SH-SAW sensor to operate as a biosensor. Many efforts at detecting liquid solution analytes (such as biological molecules) have focused on defining the interaction between the acoustic wave and the properties of the solid/liquid interface, as well as designing higher frequency SAW devises operating in the GHz range.

The present application provides a solution to the inability of SAW devices to measure analytes, including biomolecules, in liquids.

SUMMARY OF THE INVENTION

The present application is directed to microsensors for detecting the presence of a target analyte in a sample solution. The microsensor includes a SAW sensor having a hydrogel located on the sensor surface. The hydrogel further includes an immobilized molecular recognition component that is capable of detecting the target analyte.

The microsensor can also include a reference surface acoustic wave sensor surface having a hydrogel located on the reference surface. For example, the hydrogel on the reference surface does not contain the molecular recognition component. Alternatively, the control can be a measure of a sample solution that does not comprise the target analyte. The difference between the signal of the reference surface and the first sensor surface determines the presence of the target analyte.

Non-limiting examples of molecular recognition components include nucleic acids, nucleotides, nucleosides, nucleic acid analogues such as PNA and LNA molecules, proteins, peptides, antibodies including IgA, IgG, IgM, IgE, enzymes, enzymes cofactors, enzyme substrates, enzymes inhibitors, membrane receptors, kinases, Protein A, Poly U, Poly A, Poly lysine, triazine dye, boronic acid, thiol, heparin, membrane receptors, polysaccharides, coomassie blue, azure A, metal-binding peptides, sugar, carbohydrate, chelating agents, prokaryotic cells and eukaryotic cells.

Non-limiting examples of target analytes include nucleic acids, proteins, peptides, antibodies, enzymes, carbohydrates, chemical compounds, and gasses. Other exemplary target analytes include Troponin I, Troponin T, allergens, or immunoglobulins such as IgE. In certain applications, the target analyte is capable of binding more than one molecular recognition component.

In still other aspects, the hydrogel includes a polymerized monomer or hydrogel, a cross linking agent and, optionally, a chemical or UV-light activated inducer agent. Exemplary hydrogels include acrylamide, purified agarose, N-vinylpyrolidone, methacrylate, N-isopropylacrylamide, substituted acrylamide and poly(ethylene glycol) diacrylate (PEG-DA). Other exemplary monomers and dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycol- dimethacrylate, N,N'-methylenebi sacrylamide, polyethyleneglycold iacrylate(PEGDA), polyethyleneglycoldimethacrylate(PEGDMA), polyethyleneglycoldiacrylate(PEGDA), polyethyleneglycoldimethacrylate (PEGDMA), poly(vinyliden fluoride)(PVdF) based polymer, a polyacrylonitrile(PAN) based polymer, a polymethylmethacrylate(PMMA) based polymer, a polyvinyl chloride (PVC) based polymer, and a mixture of the poly(vinyliden fluoride)(PVdF) based polymer, polyacrylonitrile(PAN) based polymer, polymethylmethacrylate(PMMA) based polymer, and polyvinyl chloride(PVC) based polymer, and mixtures therof.

Exemplary cross linking agents and/or chemical or UV-light activated inducer agents include N,N'-methylenebisacrylamide, methylenebismethacrylamide ethyleneglycol-dimethacrylate and agent N,N'-methylenebisacrylamide. Irgacure 2959 (Ciba); 2,2-dimethoxy-2-phenylacetophenone, 2-methoxy-2-phenylacetone, benzyl-dimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1,1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyl-tioxantone, chloro tioxantone, 2,2-chlorobenzophenone, benzyl benzoate, and benzoyl benzoate, TEMED, and ammonium persulfate (APS).

The present application is also directed to methods of detecting a target analyte in a sample solution. A molecular recognition component is immobilized in a hydrogel located on a surface of a surface acoustic wave sensor. The sensor is contacted with the sample under conditions promoting binding of the analyte in the sample to the recognition component. A change in phase shift or frequency of a surface acoustic wave is then detected. The change determines the presence of the analyte in the sample.

In other aspects, the hydrogel also includes a crystalline colloidal array of charged particles polymerized within the hydrogel. Non-limiting examples of charged colloidal particles include colloidal polystyrene, polymethylmethacrylate, silicon dioxide, aluminum oxide, polytetrafluoroethylene and poly N-isopropylacrylamide.

A target analyte can be detected in any sample. Exemplary samples include blood, serum, plasma and urine. The method can be used for diagnostic purposes.

In another aspect, the application is directed to methods of making SAW sensors. A SAW sensor can be constructed by adding a layer of $SiO_2$ to a first sensor surface of a surface acoustic wave device, (b) attaching a linker to the $SiO_2$ layer, the linker comprising a silane group and a first comonomer, wherein the silane group reacts to attach the linker to the layer of $SiO_2$ layer; and (c) contacting the first comonomer with a medium comprising a second comonomer and a molecular recognition component under polymerisation conditions that result in a hydrogel being formed on the $SiO_2$ layer, wherein the hydrogel comprises the molecular recognition component. The medium of step (c) further comprises a cross-linking agent and a polymerisation initiator. The medium can be hydrophilic. In other variations, the hydrogel can be an ion-free gel.

The molecular recognition component can be linked to the hydrogel. For example, the molecular recognition component can be linked to the hydrogel by a first linking molecule.

Alternatively, the molecular recognition component can be linked to the hydrogel by a first linking molecule that binds to a second linking molecule attached to the hydrogel. Exemplary first or second linking molecule can be avidin and biotin.

In still other variations, the hydrogel can be hydrolyzed before adding the molecular recognition component.

The present application is further directed to a handheld instrument including the microsensors disclosed herein for detecting biological agents.

(4) GMBS croslinker; (5) having special design 25 bases oligonucleotide, having an internal HinP1 I site, an acrylamide group (Acrydite) in the 5'end and an amino group in the 3'end; (6) The polyacrylamide film.

Figure 3:
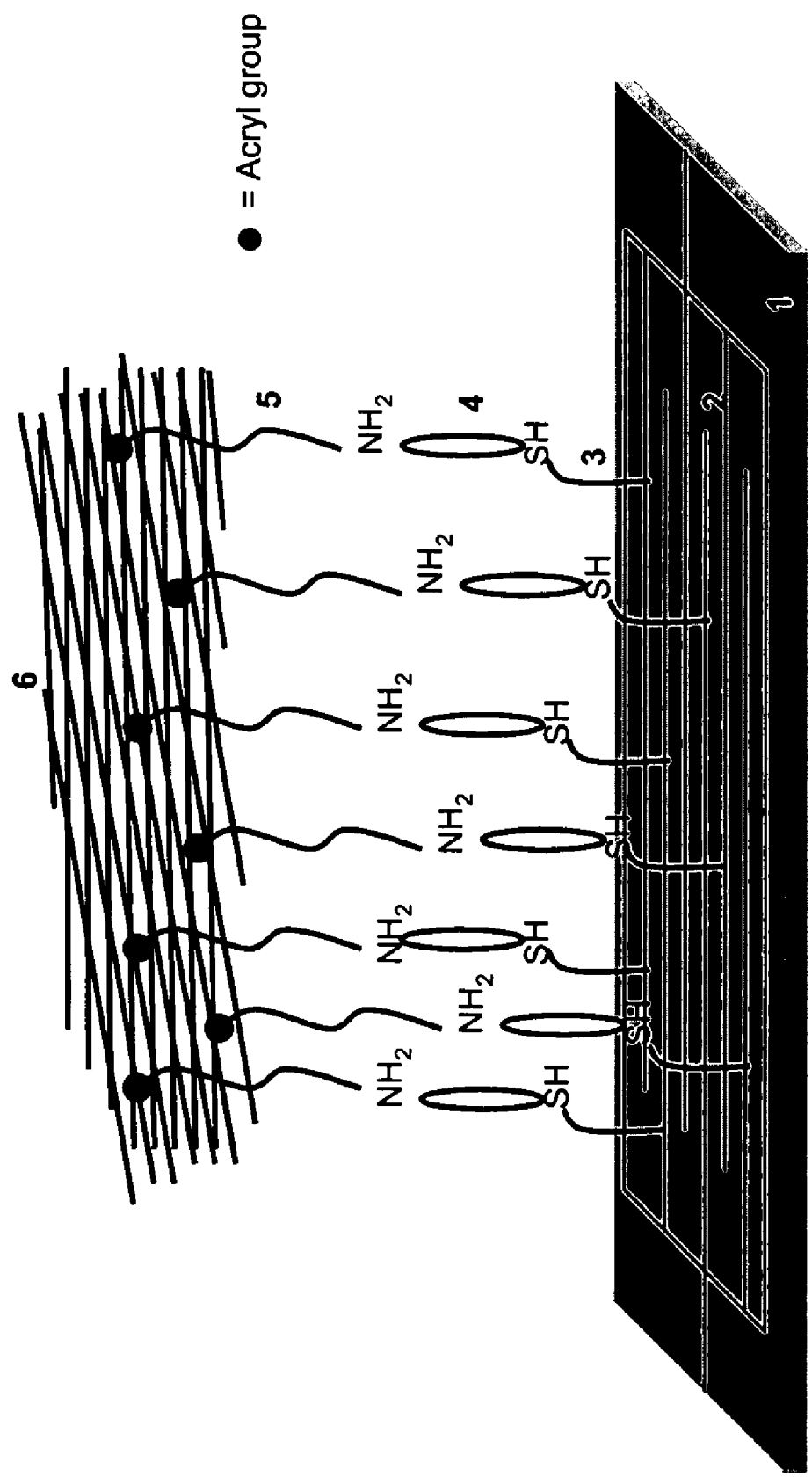
FIG. 3A depicts a schematic drawing of the SAW sensor surface having special design 25 bases oligonucleotide, having an internal HinP1 I site, an acrylamide group (Acrydite) in the 5'end and an amino group in the 3'end, attached to the SAW surface via linker molecule (3) and (4). This special oligonucleotide is taking part of an acrylamide polymerization process (6). (1) The SAW sensor surface; (2) The gold IDT on the surface; (3) 3(mercaptopropyl)trimethoxy silane.
Figure 3:
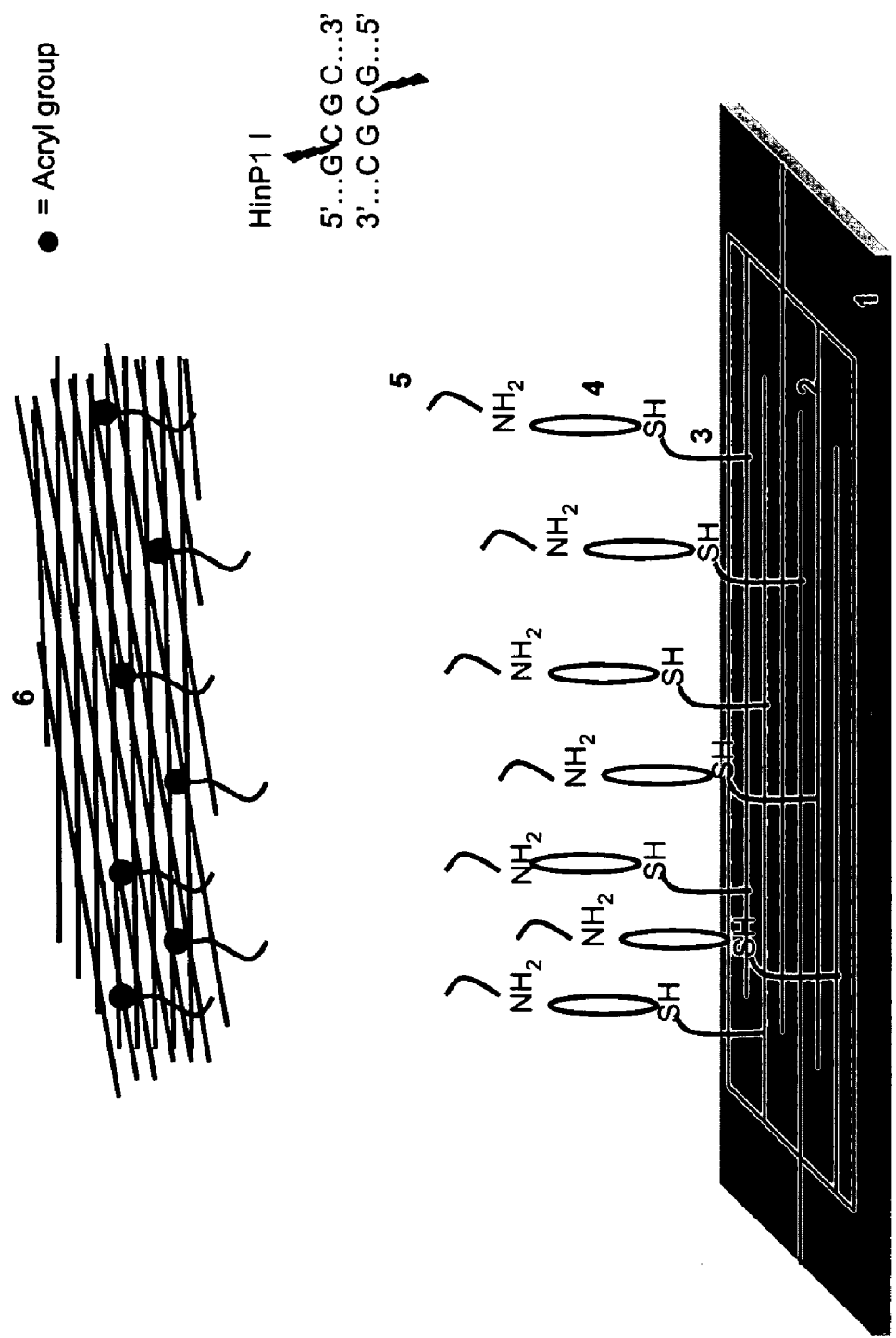

FIG. 3B are identical to FIG. 3A exact that the (5) oligonucleotide have been been cut with the restriction enzyme HinP1 to loosen the polymerized acrylamide net from the SAW surface.

Figure 4:
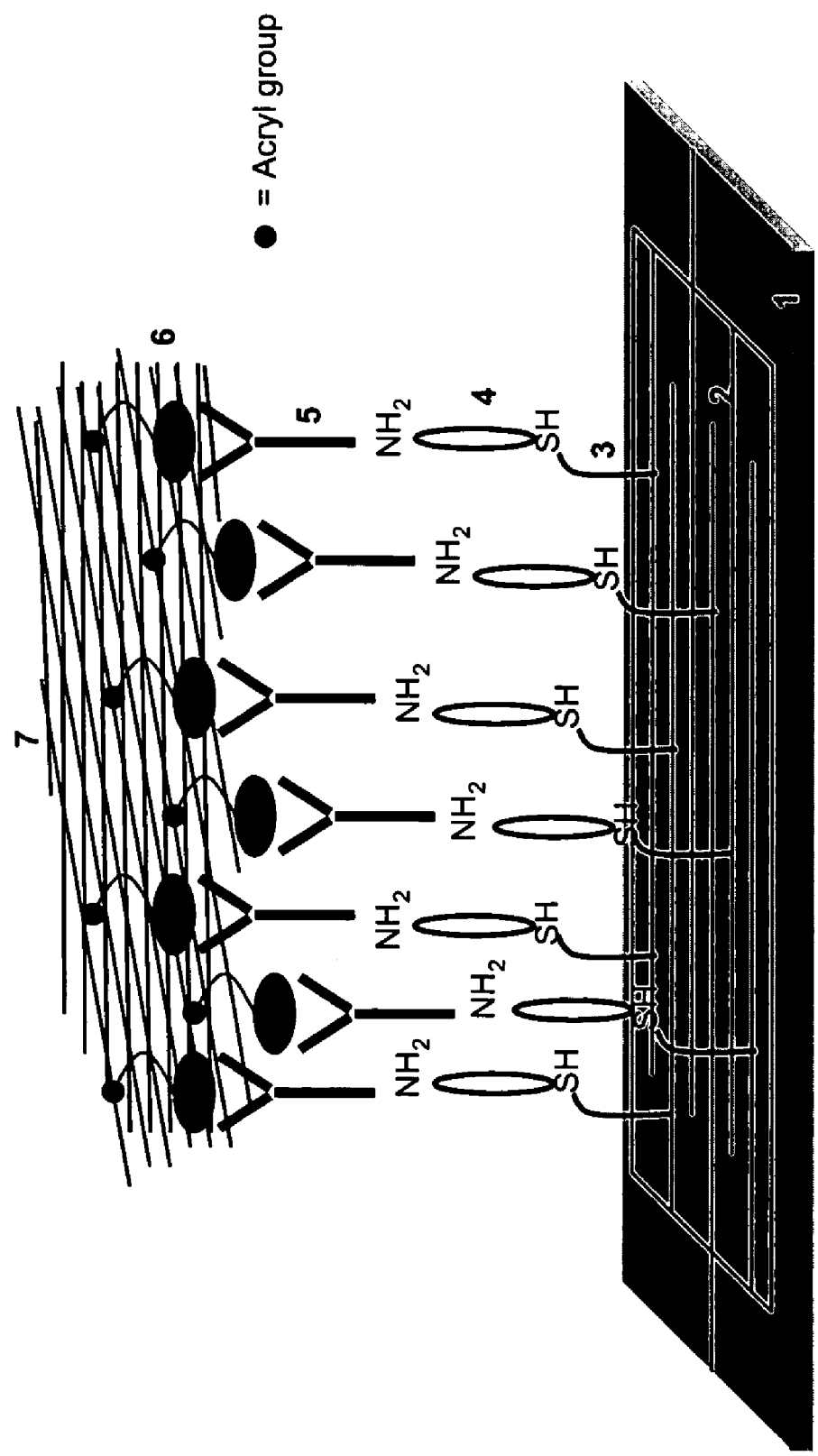
Figure 4:
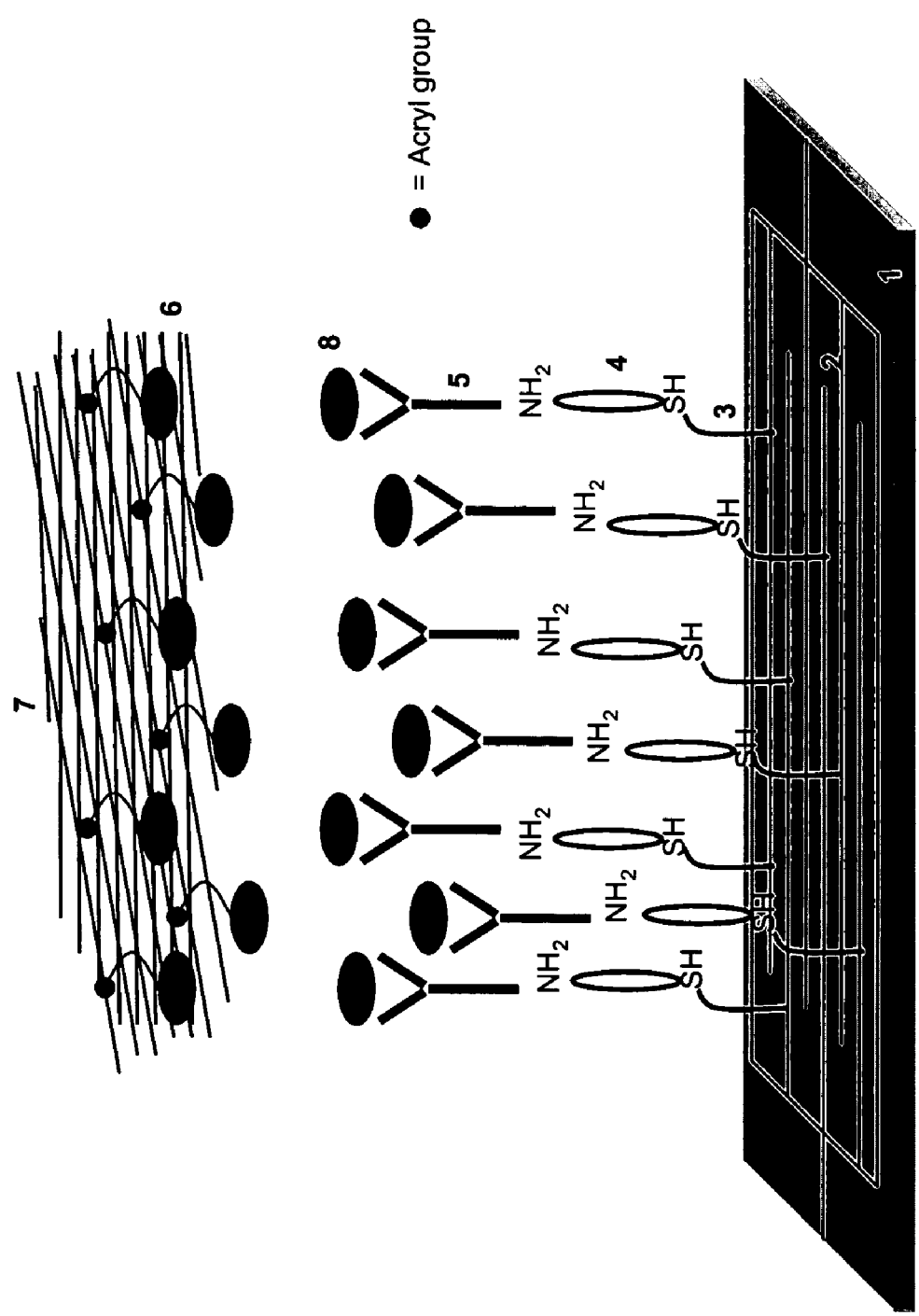

FIG. 4A depicts a schematic drawing of the SAW sensor surface having an antibody (5) attached via linker molecule (3) and (4). The antibody are hybridised with a metacrylic-modified antigen (6). The metacrylic-modified antigen is taken part of the polymerization process (7). (1); The SAW sensor surface; (2) The gold IDT on the surface; (3) 3(mercaptopropyl)trimethoxy silane; (4) GMBS crosslinker; (5) The antibody; (6) metacrylic-modified antigen; (7) The polyacrylamide hydrogel.

FIG. 4B are identical to FIG. 3A exact that a competing non-modified antigen (8) is relishing the polyacrylamide hydrogel from the SAW sensor surface.

FIG. 5A depicts a picture of the front side of the print card where the two SAW sensors where attached using standard flip chip technology. (1) SAW reference sensor; (2) SAW sensing sensor; (3)-(8) electric connections coming from the two SAW sensors; (9) the print card substrate (aluminium oxide); (10) special design gasket.

Figure 5:
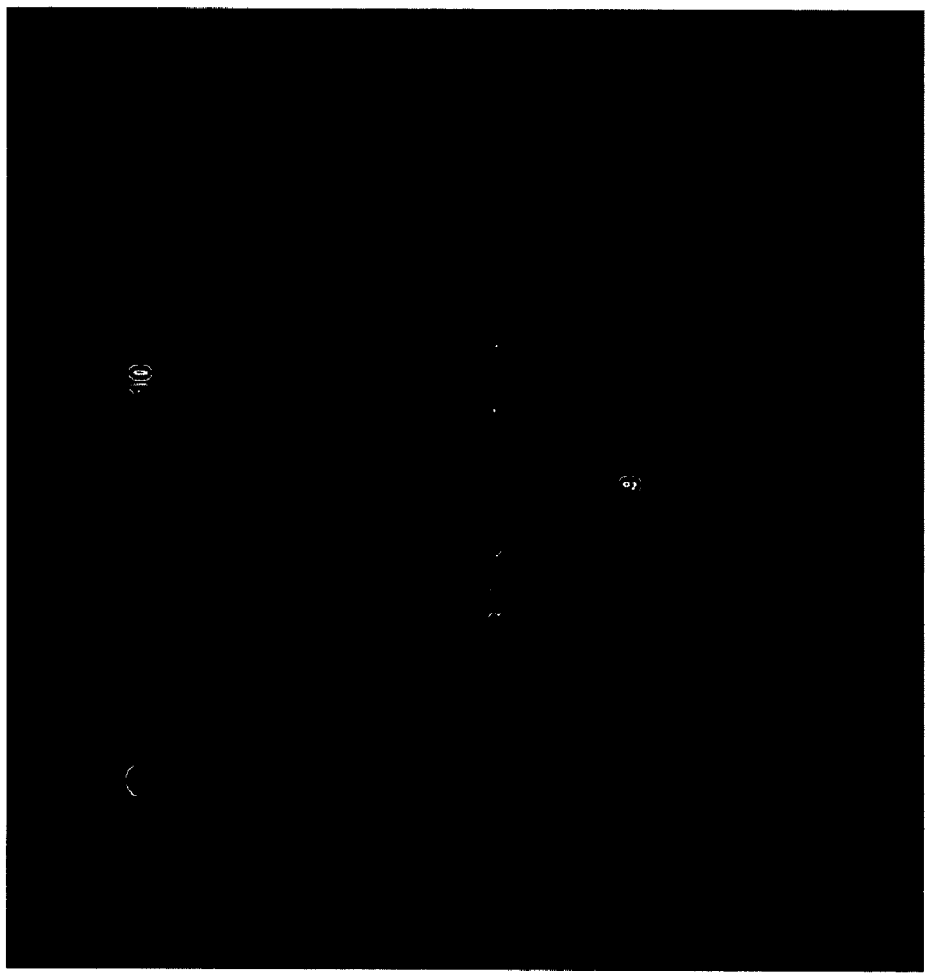
Figure 5B:
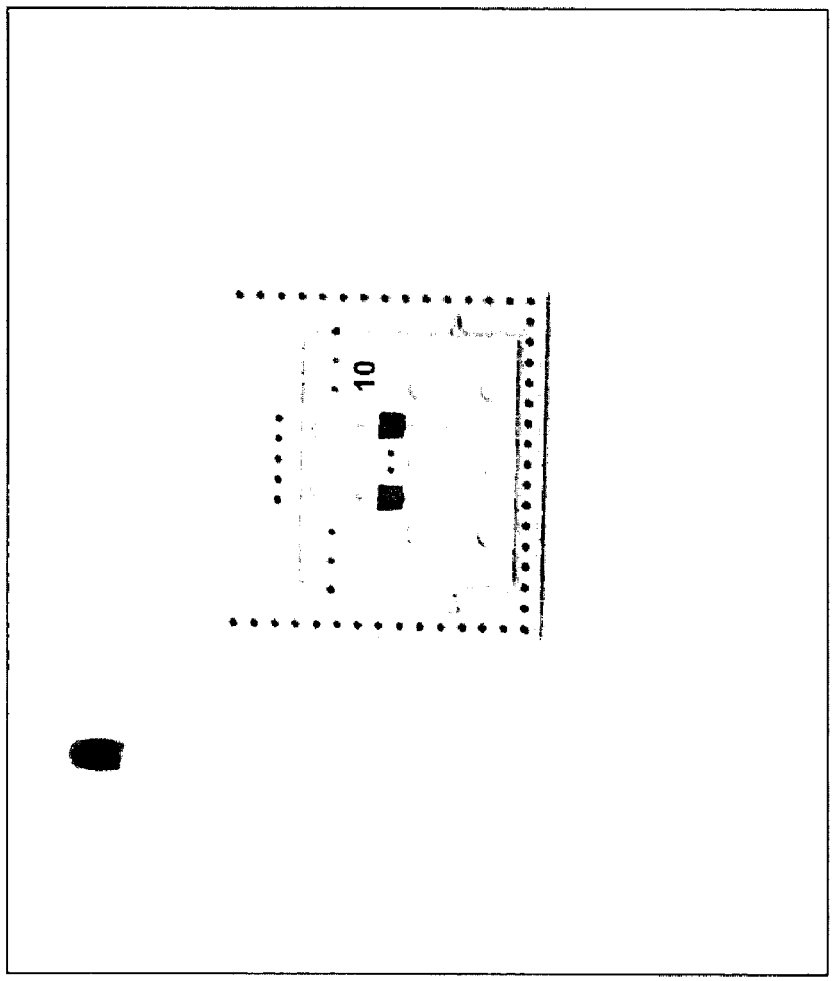

FIG. 5B depicts a picture identical to FIG. 5A where the gasket has been placed on top to the print card (10).

Figure 6A:
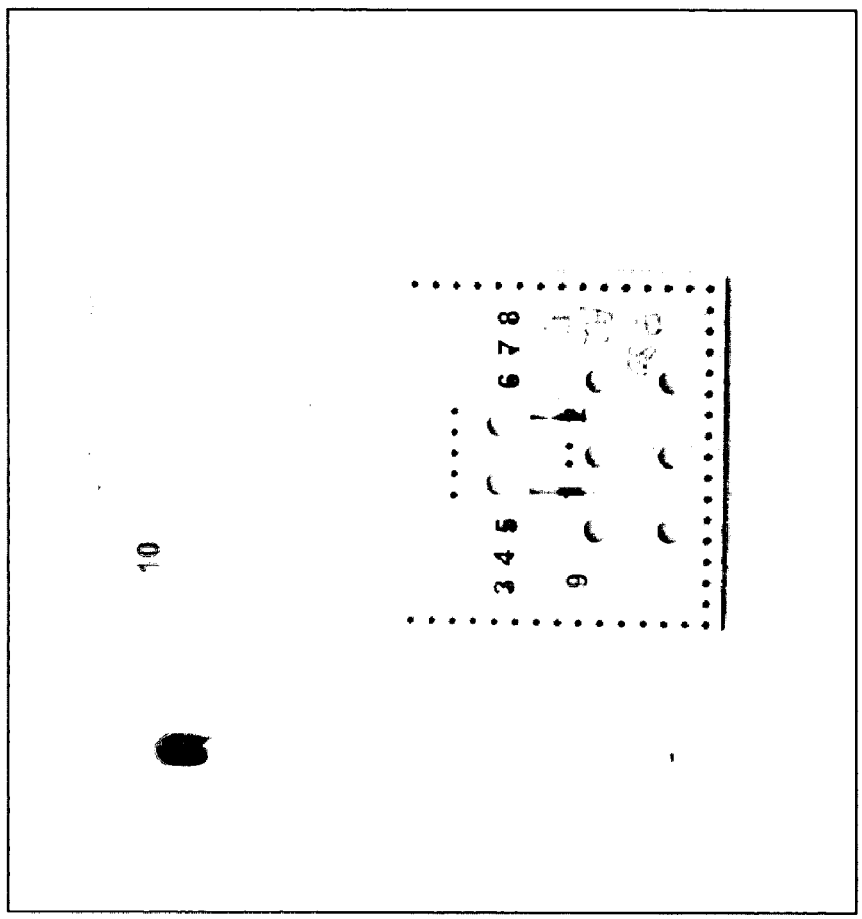

FIG. 6A depicts a picture of the backside of the print card where the two SAW sensors where attached using standard flip chip technology. (1) The SAW reference sensor surface can be seen in the small channel; (2) SAW sensing sensor can be seen in the small channel; (3)-(8) electric connections coming from the two SAW sensors ready to enter a female plug on the instrument; (9) the electric connecting material; (10) special design gasket.

FIG. 6B depicts a picture identical to FIG. 6A where the gasket (10) has been placed on top to the print card (10).

Figure 7:
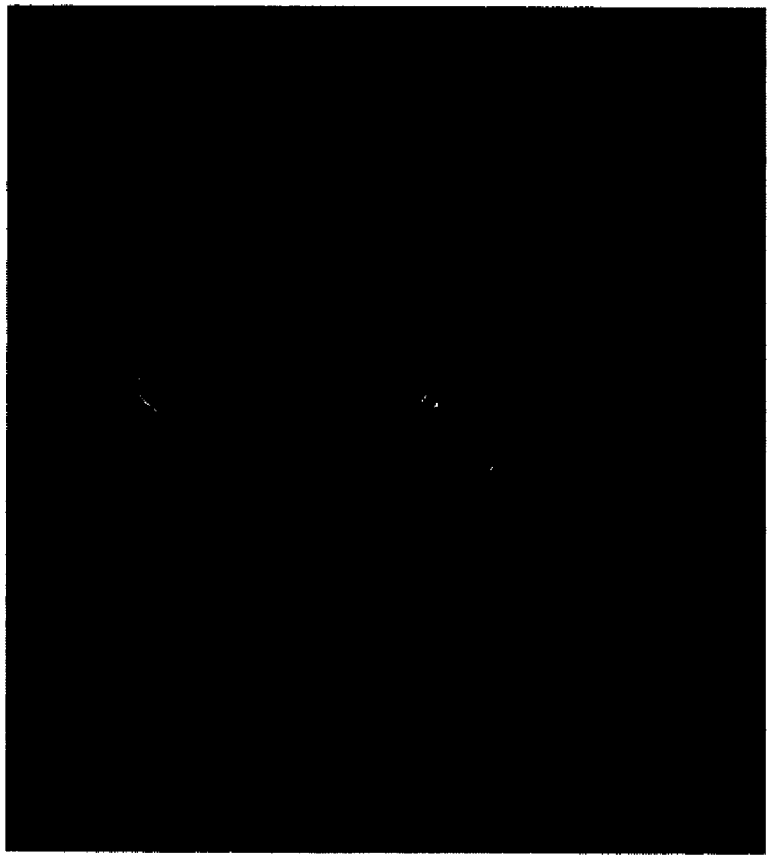

FIG. 7 depicts a picture identical to FIG. 6A where a special design PMMA block (1) has been places on top of the gasket (10) to generate the complete cartridge.

Figure 8:
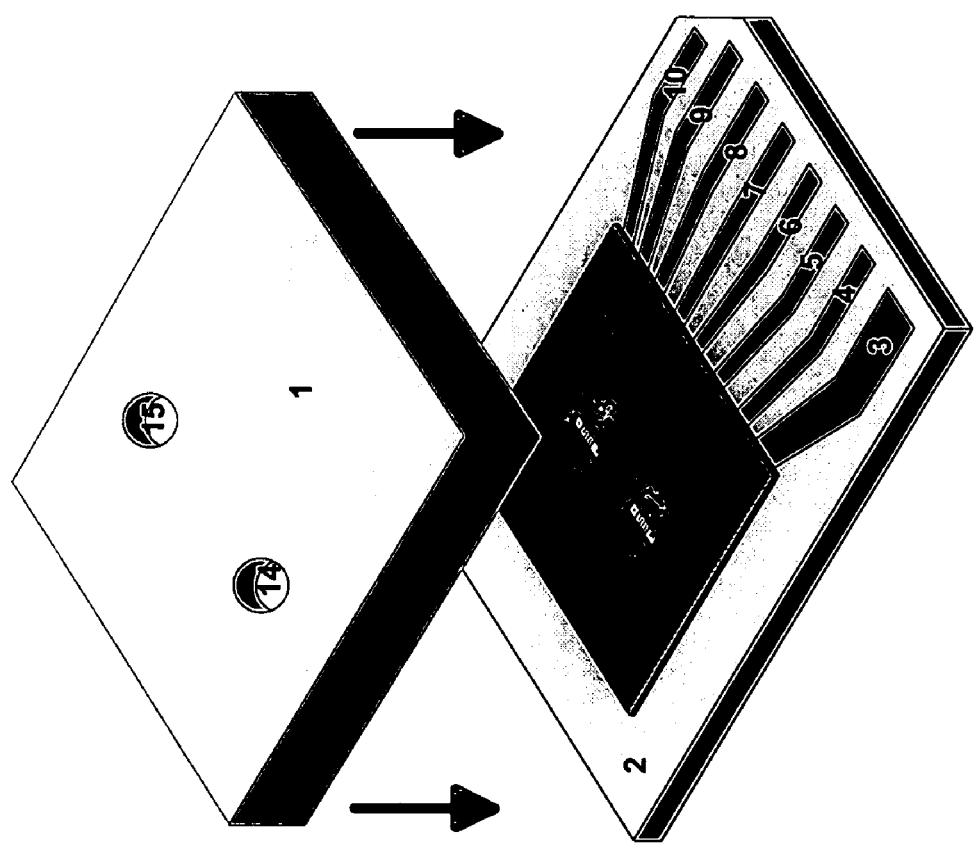

FIG. 8 depicts a schematically drawing of FIG. 7 where all the part can be seen. (1) The top PMMA block; (2) The bottom PMMA block; (3) to (10) The electric connectors; (11) one of the two gasket; (12) and (13) The two SAW sensors; (14) and (15) The sample inlets.

Figure 9:
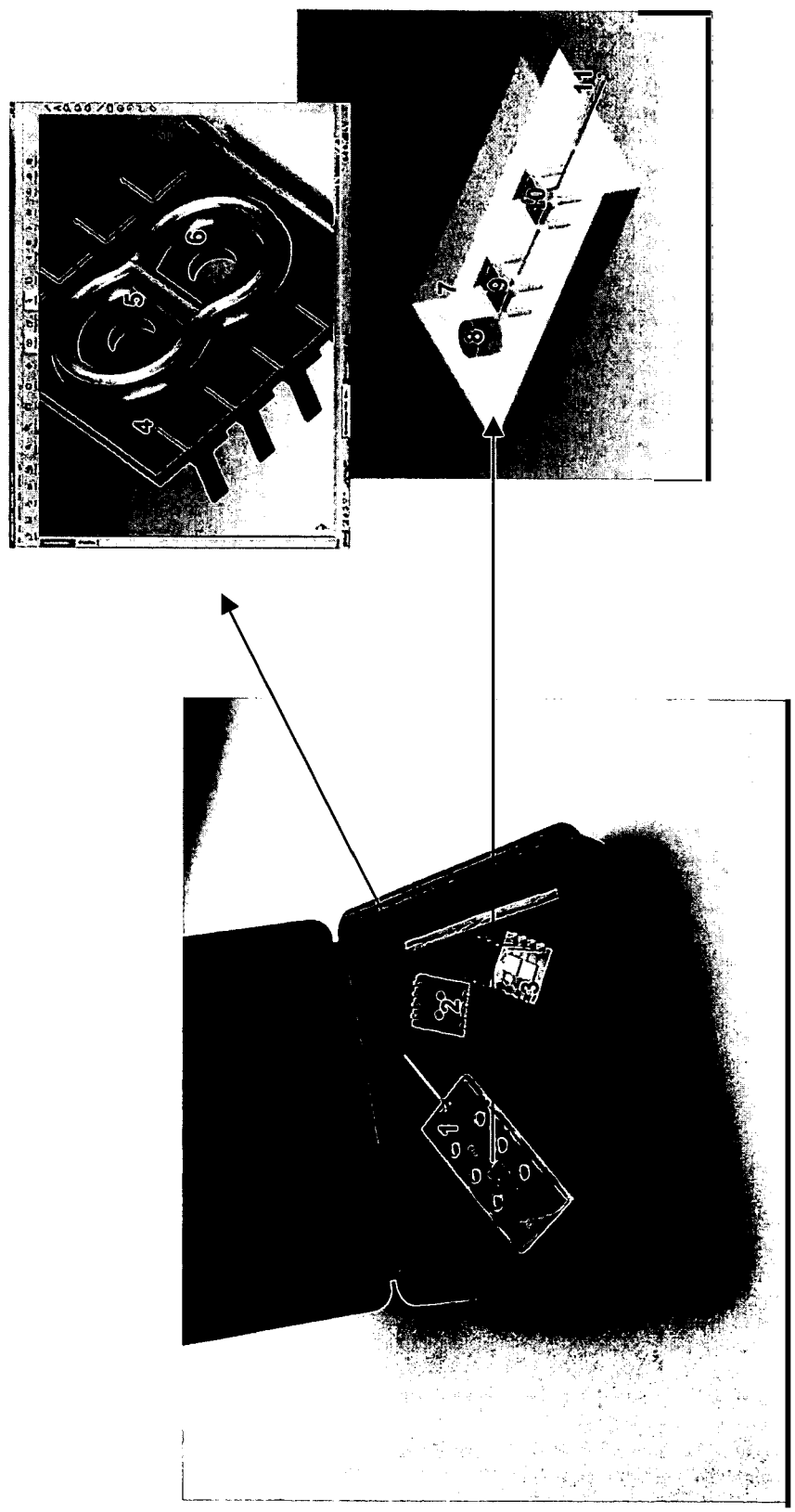

FIG. 9 depicts both a picture and a drawing of alternative cartridges for holding the two SAW sensors. (1) A flow cartridge design to hold two SAW sensors; (7) The cartridge at made in PMMA; (8) The sample inlet; (9) localization for first SAW sensor, both SAW sensor are in this setup electric connected four spring probes each; (10) localisation for second SAW sensor; (I 1) tube for connecting to a external pump; (2) a picture of the front side of the cartridge where the two SAW sensors where attached using standard flip chip technology (3) a picture of the backside of the cartridge where the four connection coming for each SAW sensor can been seen; (4) drawing of the cartridge; (5) sample inlet for the reference SAW sensor, the SAW sensor are not seen at the drawing; (6) sample inlet of the sensing SAW sensor, the SAW sensor are no seen at the drawing.

Figure 10:
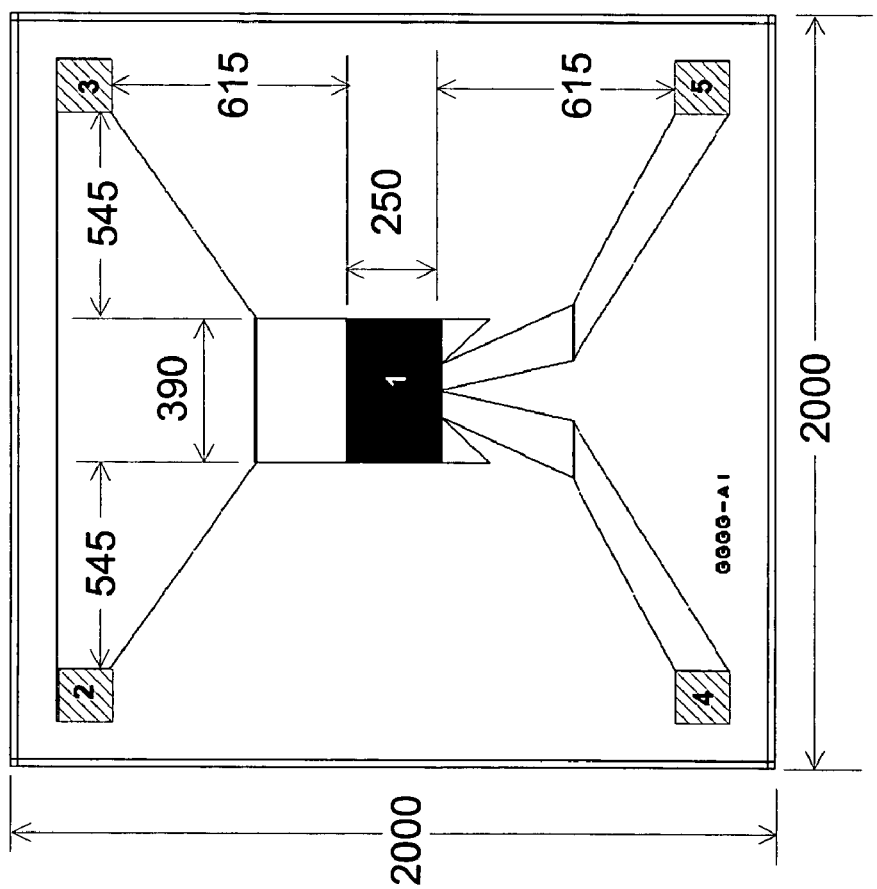

FIG. 10 depicts a drawing of the SAW sensor dimensions in micrometer. (1) The SAW sensing area; (2) to (5) The contact pads.

Figure 11:
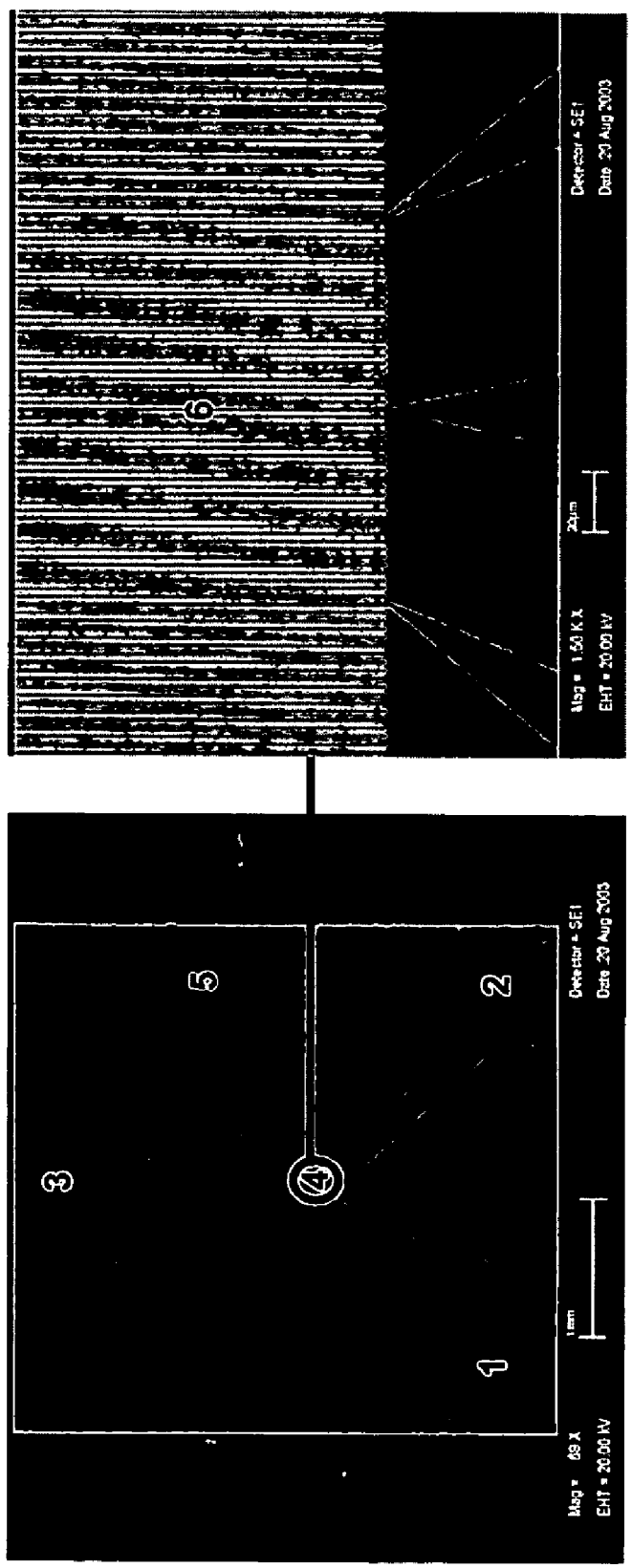

FIG. 11 depicts a enlarged picture of the SAW sensor surface. (1)-(3) The contact pads; (4) The sensing area; (5) The piezoelectric substrate; (6) The Interdigital transducers (IDT) or Interdigital Electrodes (IDE) pattern.

Figure 12:
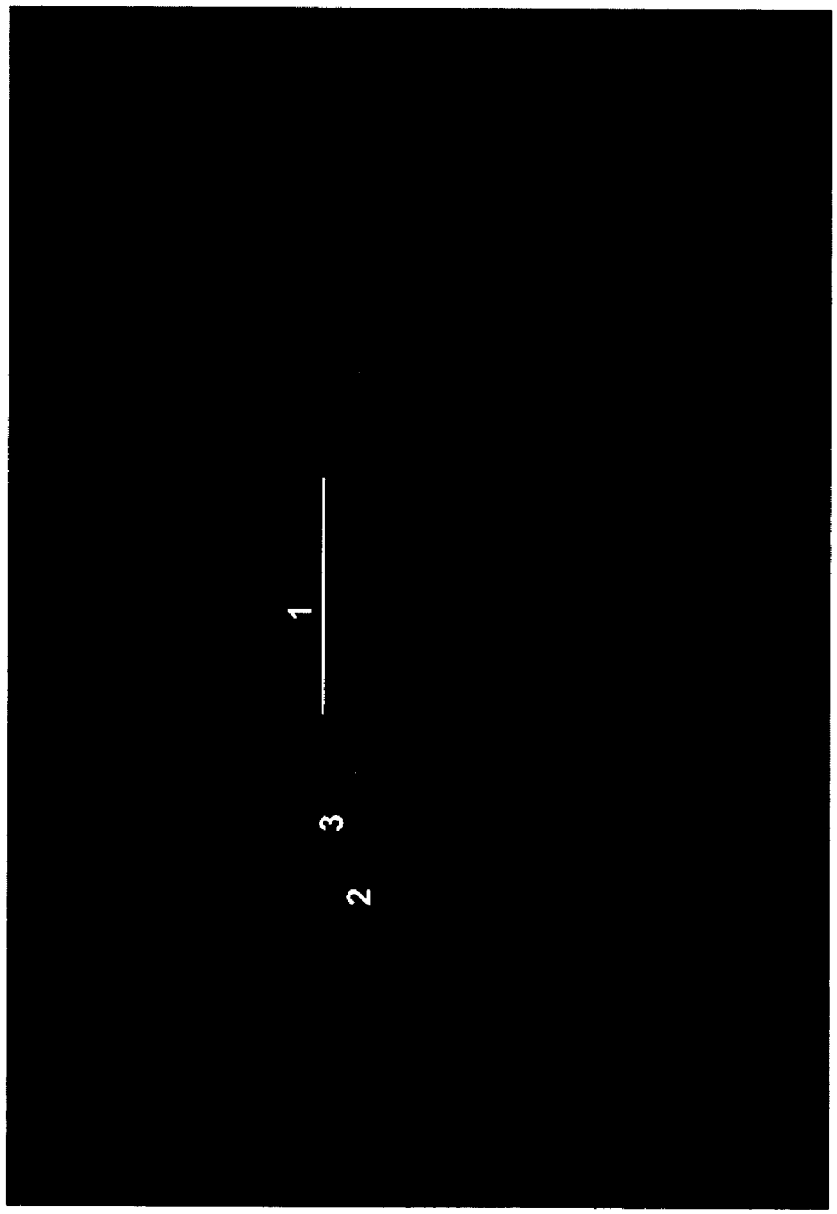

FIG. 12 depicts a enlarged picture of the cross section of to IDT. (1) Spacing I micrometer between the two electrodes; (2) The gold surface; (3) The 50 nm $SiO_2$ surface.

Figure 13:
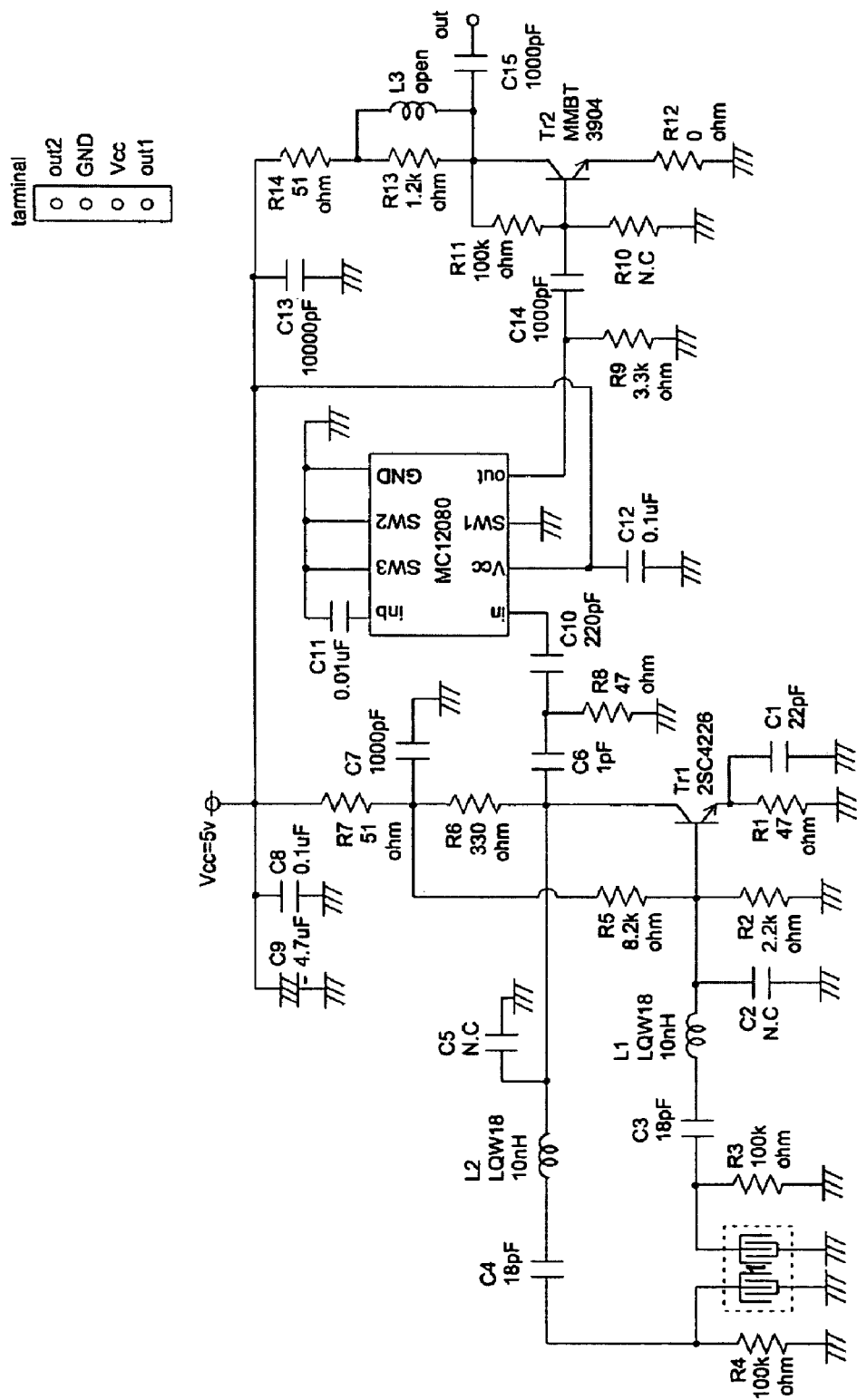

FIG. 13 depicts a schematic drawing of the electronic design: Each SAW sensor was operated by the electronics illustrated at FIG. 13. The output of each SAW sensor circuit was connected to a two-channel frequency counter HP (Agilent) 53131A. Alternative special design electronics was constructed to bypass the frequency counter.

Figure 14:
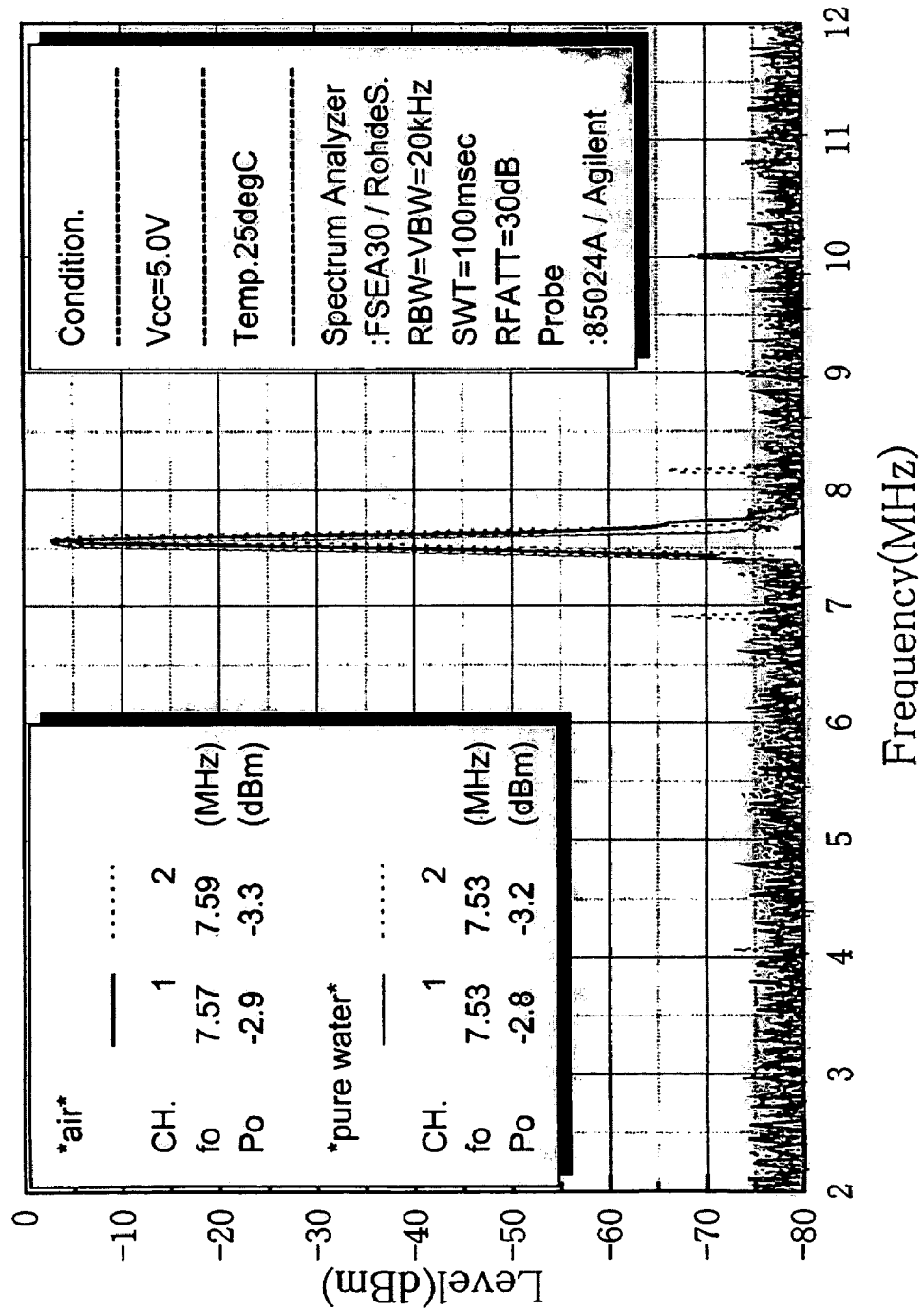

FIG. 14 depicts a measurement result showing the SAW sensors operating in air and water.

Figure 15:
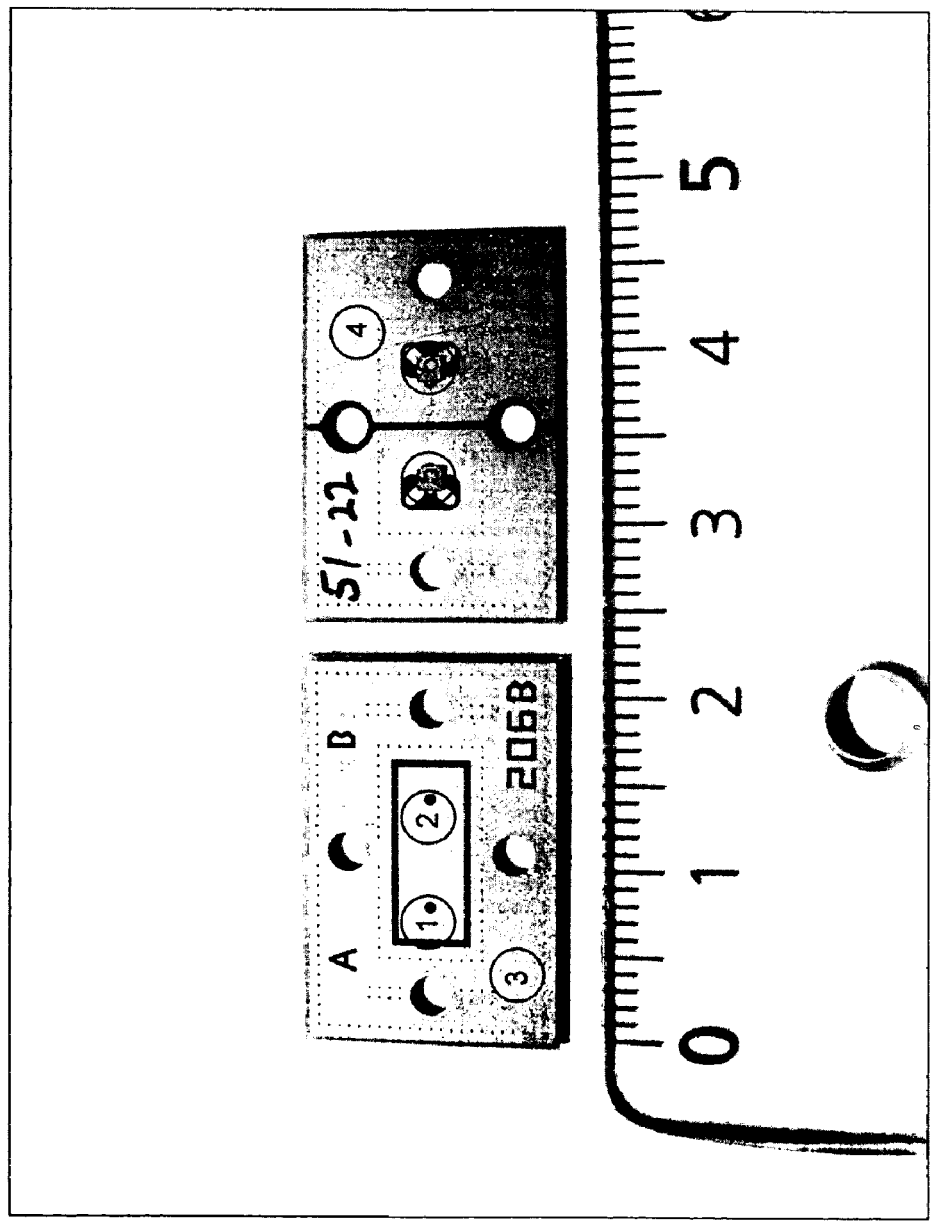

FIG. 15 depicts a picture of a sensor unit consisting of two SAW resonators. (1) The inlet hole for the sensing resonator; (2) the inlet hole for the reference resonator; (3) the gold-coated substrate upon where the two resonators are attached; (4) the backside of the sensor unit; (5) backside of the sensing resonator; (6) backside of the reference resonator.

Figure 16:
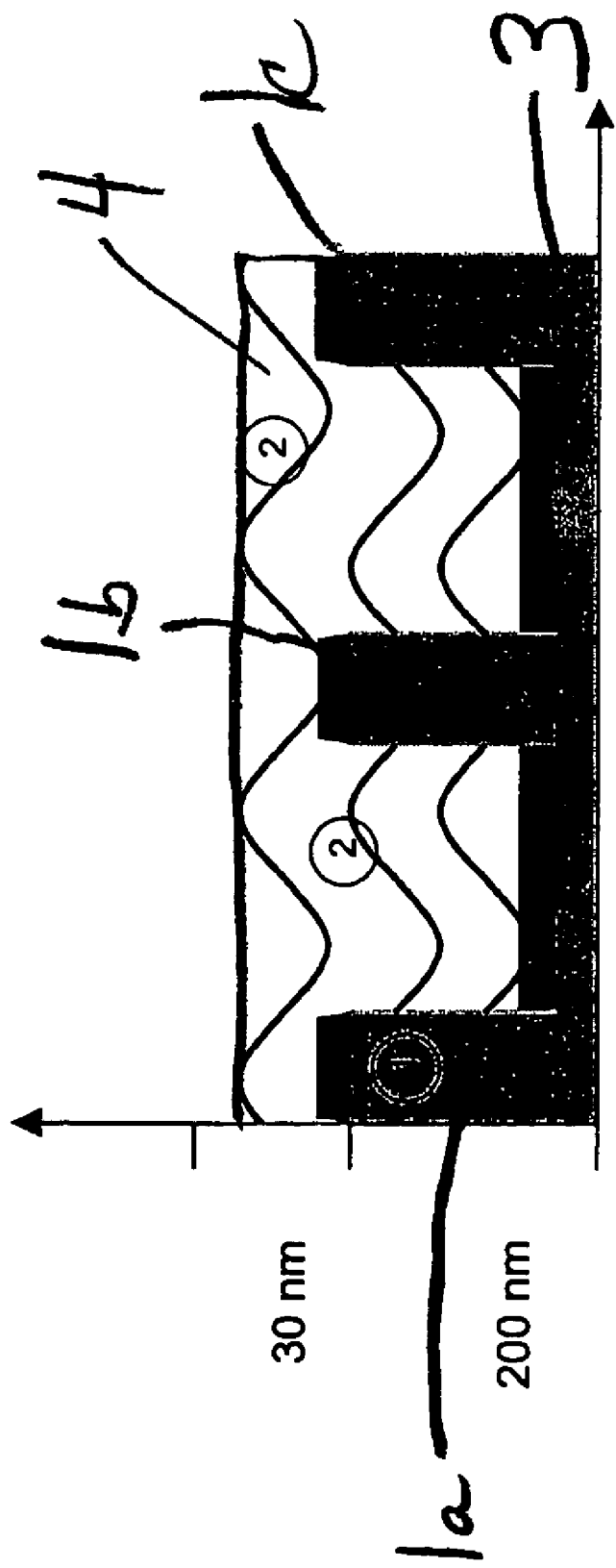

FIG. 16 depicts a schematic drawing of the IDT structures. (1) IDT structures; (2) surface acoustic wave.

Figure 17:
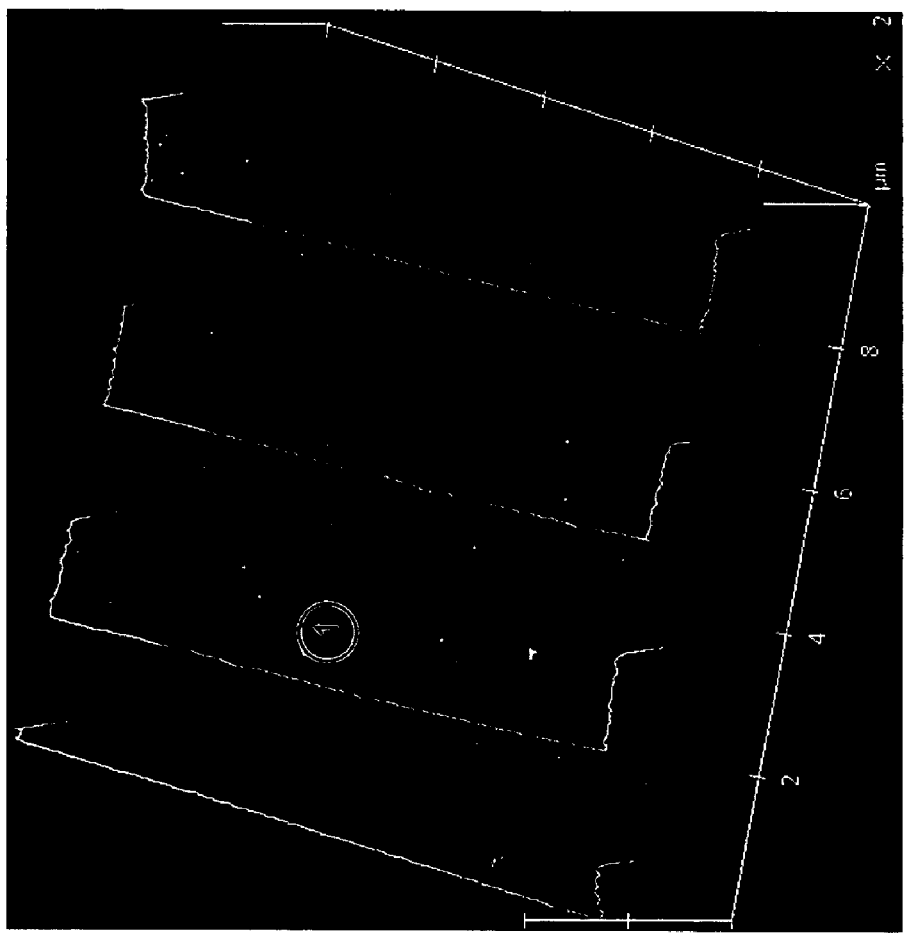

FIG. 17 depicts a picture of a AFM scanning of the IDT structures. (1) The IDT are made of gold with a 50 nm SiO2 layer on top of the gold structures.

Figure 18:
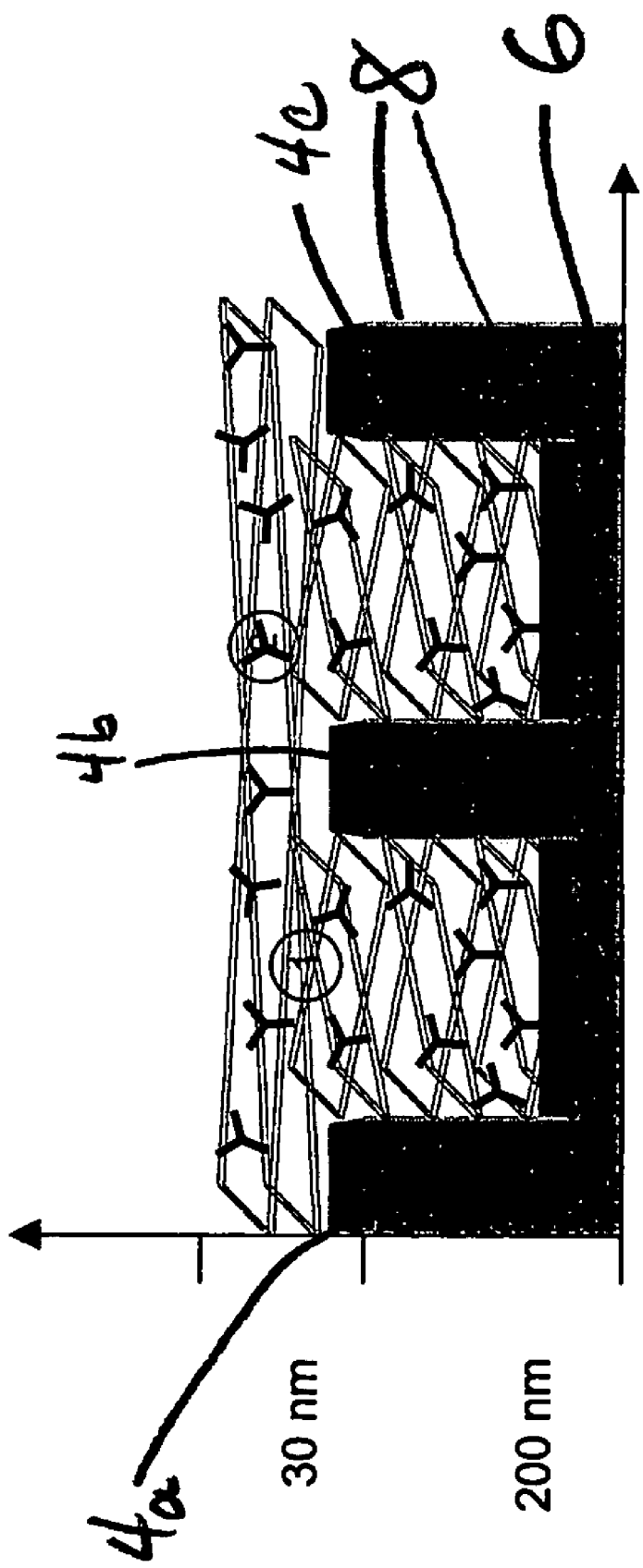

FIG. 18 depicts a schematic drawing of the IDT's is having applied the antibody/hydrogel matrix between the structures. (1) Hydrogel solution; (2) antibodies.

Figure 19:
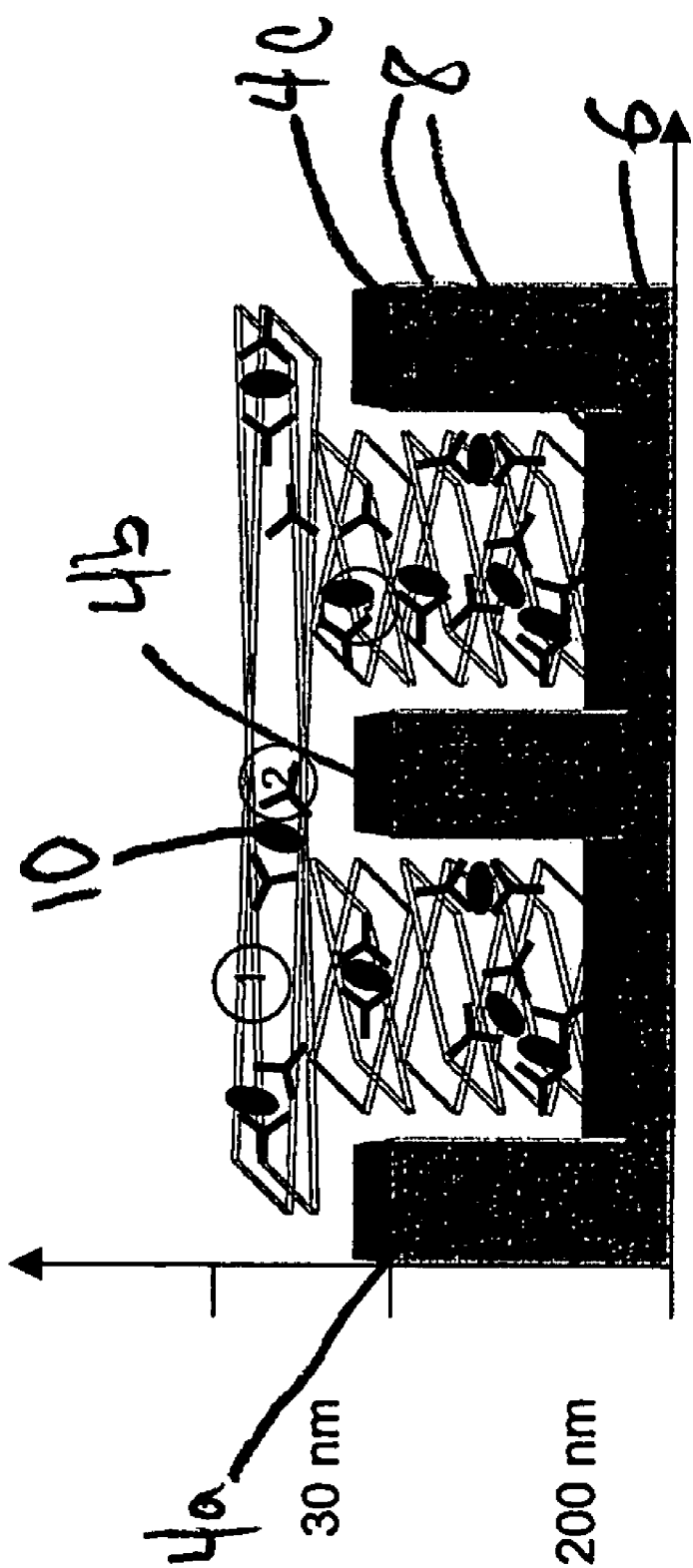

FIG. 19 depicts a schematic drawing of the IDT's is having applied the antibody/hydrogel matrix between the structures and the interaction analyte. (I) Hydrogel solution; (2) antibodies; (3) analyte.

Figure 20:
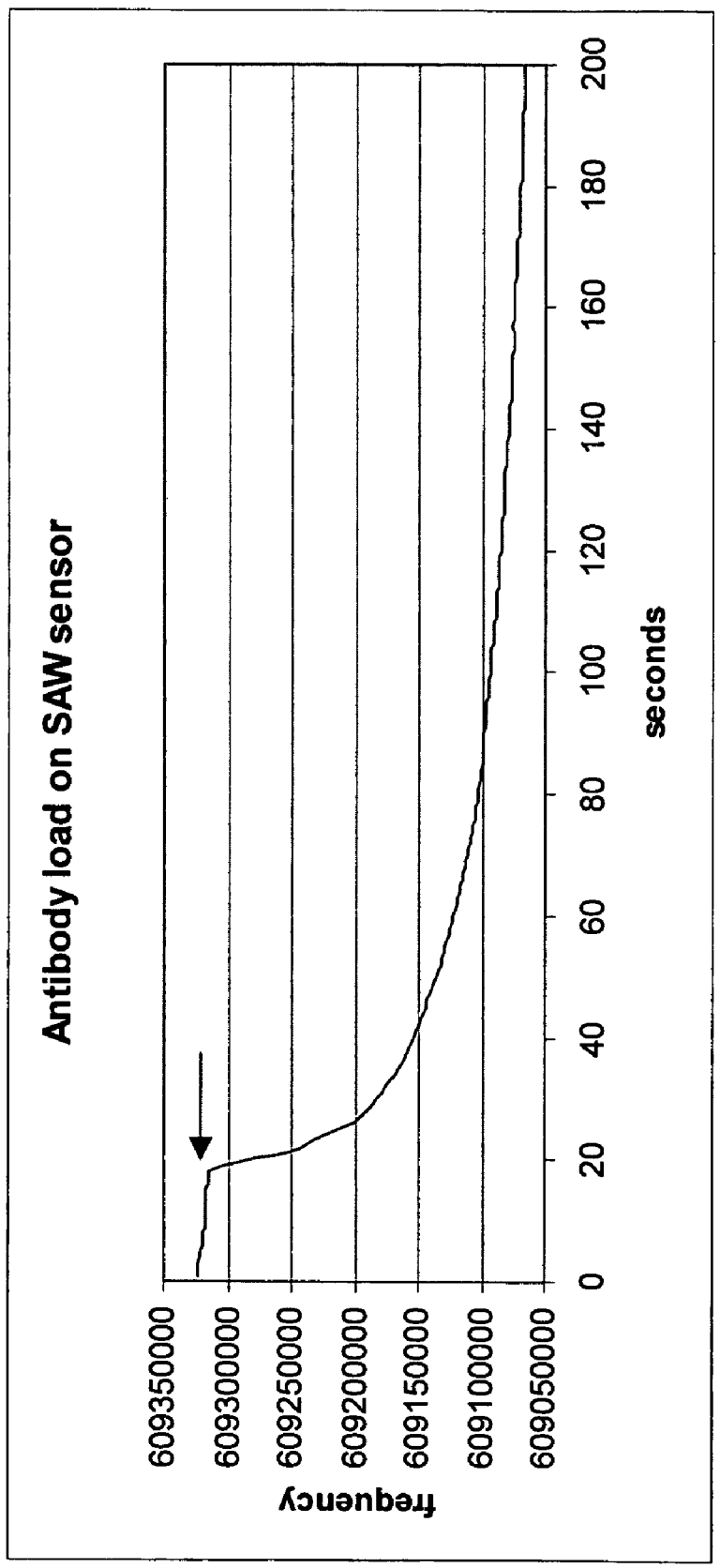

FIG. 20 depicts a frequency curve of the hydrogel/antibody solution loaded on the sensing resonator structures. The hydrogel/antibody solution is applied down in the hole illustrated at FIG. 15 (2). The hydrogel/antibody solution is applied to the SAW resonator at the arrow.

Figure 21:
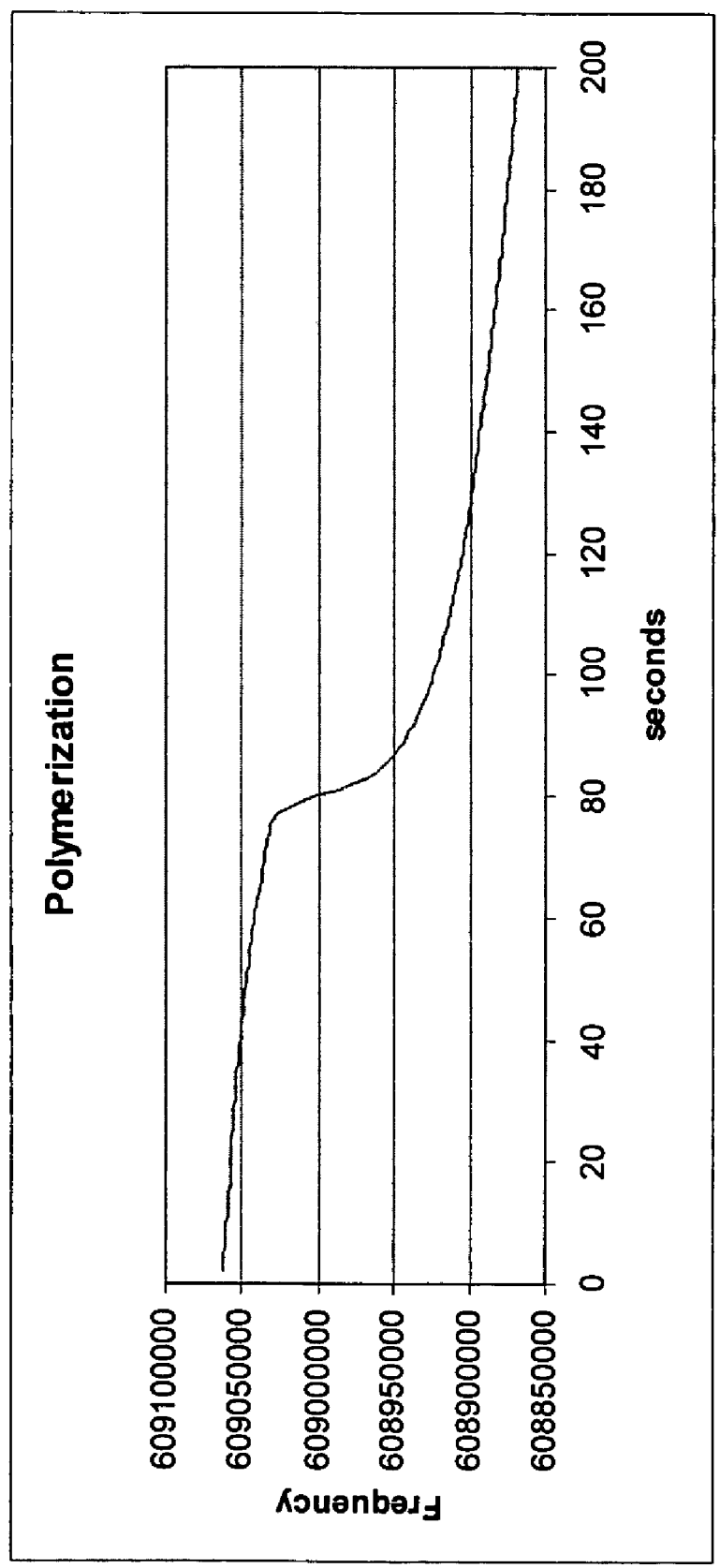

FIG. 21 depicts a frequency curve of the polymerisation reaction on the hydrogel/antibody loaded SAW resonator. 365 nm UV light are applied at time 0.

Figure 22:
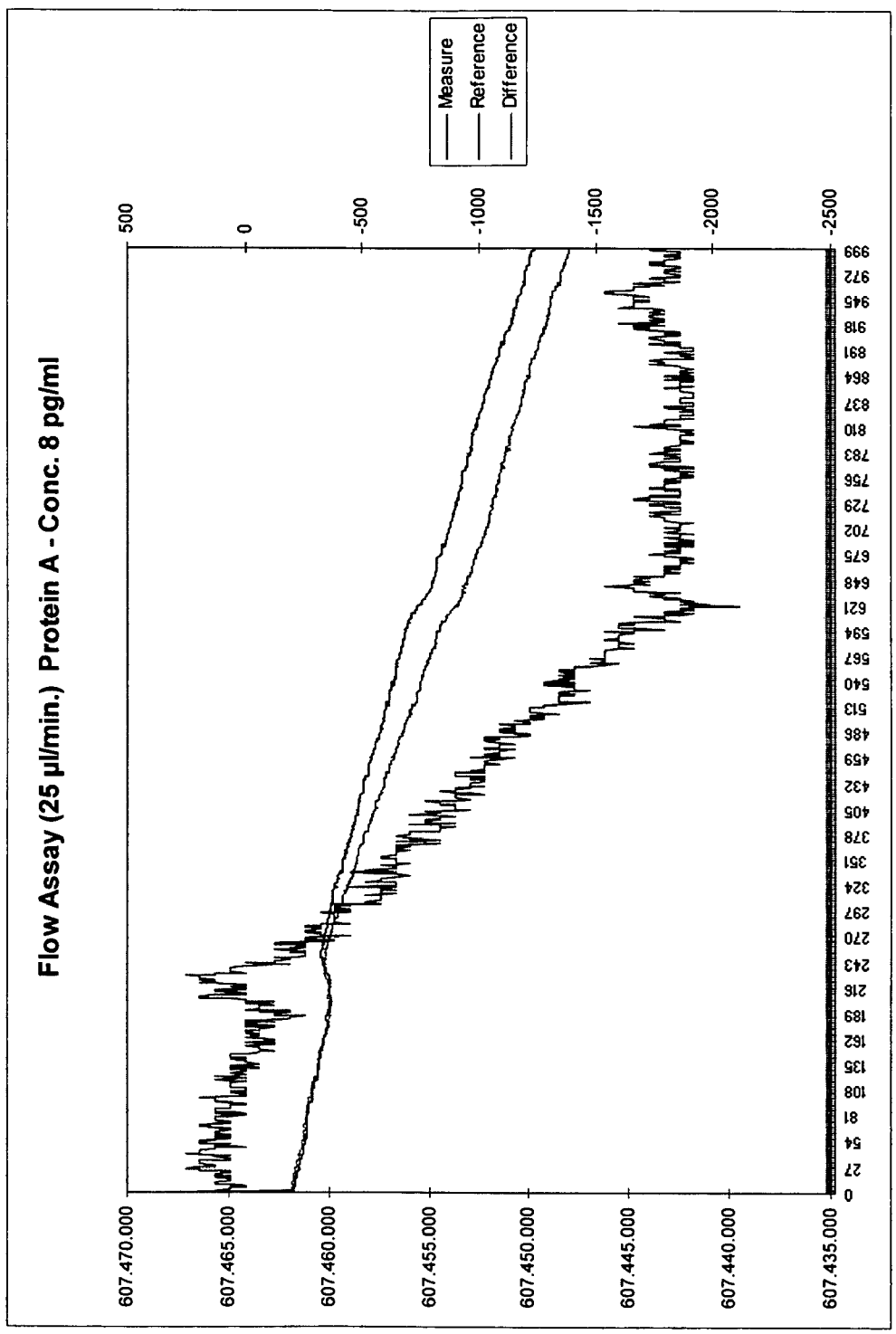

FIG. 22 depicts a frequency curve of the interaction between the analyte Protein A and the antibody against protein A. In the left Y axis the real frequency response can be observed. In the right Y axis the differential frequency response between the two SAW resonators can be observed. The time on the X axis is in seconds. Protein A sample are injected after approx. 230 seconds. The blue curve represent the signal from the reference SAW resonator only having the hydrogel solution applied to the surface. The red curve represent the signal from the sensing SAW resonator having the hydrogel/antibody solution applied to the surface. The green curve represents the differential signal between the two SAW resonator curves.

DETAILED DESCRIPTION OF THE INVENTION

The present invention is directed to microsensors and methods of using the microsensors for detecting the presence of a target analyte in a liquid sample. The microsensors include a molecular recognition component immobilized in a hydrogel located at the surface of a SAW sensor. When the molecular recognition component binds a target analyte, a change in the phase or frequency of the surface wave is observed, thereby determining the presence of the target analyte in the sample. The acoustic wave sensor disclosed herein this provides a detection method readily adaptable to detecting liquid soluble analytes, including biological molecules (e.g. nucleic acids and proteins), at high sensitivity and in the absence of labelling.

I. Surface Acoustic Wave Sensors

The microsensors disclosed herein include at least one surface acoustic wave sensor. A surface acoustic wave sensor includes a piezoelectric layer, or piezoelectric substrate, and input and output transducer(s). A surface acoustic wave is generated within the piezoelectric layer and is detected by interdigitated electrodes. As described in more detail below, binding events that alter the surface of the surface acoustic wave sensor can be detected as a change in a property of the propagating surface acoustic wave. Surface acoustic wave sensors are described in U.S. Pat. Nos. 5,130,257; 5,283,037; and 5,306,644; F. Josse, et. al. "Guided Shear Horizontal Surface Acoustic Wave Sensors for Chemical and Biochemical Detection in Liquids," Anal. Chem. 2001, 73, 5937; and W. Welsch, et. al., "Development of a Surface Acoustic Wave Immunosensor," Anal. Chem. 1996, 68, 2000-2004; each of which is hereby expressly incorporated by reference in its entirety.

Acoustic wave devices are described by the mode of wave propagation through or on a piezoelectric substrate. Acoustic waves are distinguished primarily by their velocities and displacement directions. Many combinations are possible, depending on the material and boundary conditions. The interdigital transducer (IDT) of each sensor provides the electric field necessary to displace the substrate and thus form an acoustic wave. The wave propagates through the substrate, where it is converted back to an electric field at the IDT at the opposing electrode. Transverse, or shear, waves have particle displacements that are normal to the direction of wave propagation and which can be polarized so that the particle displacements are either parallel to or normal to the sensing surface. Shear horizontal wave motion signifies transverse displacements polarized parallel to the sensing surface; shear vertical motion indicates transverse displacements normal to the surface.

The present invention combines the use of "standard" SAW biosensors with the hydrogels that include a molecular recognition component specific to a target analyte. Binding of the molecular recognition components to a target analyte results in a measurable change in phase or frequency of the SAW.

By 'surface acoustic wave sensor', or 'surface acoustic wave device' herein is meant any device that operates substantially in the manner described above. In some embodiments, 'surface acoustic wave sensor' refers to both surface transverse wave devices, where the surface displacement is perpendicular to the direction of propagation and parallel to the device surface, as well as surface acoustic wave sensors where at least a portion of the surface displacement is perpendicular to the device surface. While surface transverse wave devices generally have better sensitivity in a fluid, it has been shown that sufficient sensitivity may also be achieved when a portion of the surface displacement is perpendicular to the device surface. See, for example, M. Rapp, et. al. "Modification of Commercially Available LOW-LOSS SAW devices towards an immunosensor for in situ Measurements in Water" 1995 IEEE International Ultrasonics Symposium, Nov. 7-10, 1995, Seattle, Wash.; and N. Barie, et. al., "Covalent bound sensing layers on surface acoustic wave biosensors," Biosensors & Bioelectronics 16 (2001) 979; all of which are expressly incorporated herein by reference.

The sensors are made by a photolithographic process. Manufacturing begins by carefully polishing and cleaning the piezoelectric substrate. Metal such as gold or aluminum is then deposited uniformly onto the substrate. The device is spin-coated with a photoresist and baked to harden it. It is then exposed to UV light through a mask with opaque areas corresponding to the areas to be metalized on the final device. The exposed areas undergo a chemical change that allows them to be removed with a developing solution. Finally, the remaining photoresist is removed. The pattern of metal remaining on the device is called an interdigital transducer (IDT) or interdigital electrodes (IDE). By changing the length, width, position, and thickness of the IDT, the performance of the sensor can be maximized.

A. Piezoelectric Layer

The surface acoustic wave sensors include a piezoelectric layer, or piezoelectric substrate. Piezoelectricity refers to the production of electrical charges by the imposition of mechanical stress. The phenomenon is reciprocal. Applying an appropriate electrical field to a piezoelectric material creates a mechanical stress. Piezoelectric acoustic wave sensors apply an oscillating electric field to create a mechanical wave, which propagates through the hydrogel and is then converted back to an electric field for measurement.

The piezoelectric substrate may be made from quartz, lithium niobate ($LiNbO_3$), or any other piezoelectric material. The cut of the piezoelectric substrate relative to its crystal structure should be such that acoustic waves are trapped at the surface and the desired direction of material displacement relative to the surface and to the propagating wave (as described above) is achieved.

Among the piezoelectic substrate materials that can be used for acoustic wave sensors and devices, the most common are quartz ($SiO_2$), lithium tantalate ($LiTaO_3$), and, to a lesser degree, lithium niobate ($LiNbO_3$). Other materials with commercial potential include gallium arsenide (GaAs), silicon carbide (SiC), langasite (LGS), zinc oxide (ZnO), aluminum nitride (AlN), lead zirconium titanate (PZT), and polyvinylidene fluoride (PVdF). The piezoelectric substrate may be made from quartz, lithium niobate ($LiNbO_3$), or any other piezoelectric material.

The piezoelectric support may be formed of any suitable piezoelectric material. Generally, suitable materials will have the following properties: 1. Large surface shear horizontal displacement, 2. Large electromechanical coupling constant, 3. Zero or small piezoelectric coupling to SAW and other bulk waves, 4. Zero or small beam steering both on the surface and into the bulk, 5. Zero or small temperature coefficient of delay.

The thickness of the piezoelectric support is generally not critical but is typically of the order of 0.5 mm for ease of handling. A reflecting lower surface could result in a plate-mode configuration which is not preferred. The support may alternatively comprise a slab of non-piezoelectric material with a thin layer of piezoelectric material coated on its surface.

B. Dielectric Insulator Coating

The surfaces of the piezoelectric substrate and the electrode(s) is preferably coated or intimately contacted with a material having a good impedance match with the piezoelectric material and high acoustic absorption. This is to ensure that acoustic energy propagated through the piezoelectric material is not reflected back towards the active surface of the device. Suitable materials include plastics, wax and silicone rubber.

The dielectric layer may be formed of any suitable dielectric material. Suitable materials will have the property that the acoustic velocity in the dielectric is lower than that in the piezoelectric substrate. Examples of suitable materials include silicon dioxide and certain polymers, e.g. polymethylmethacrylate, polytetrafluoroethylene, polystyrene and polyethylene. Where polymers are used, they are preferably cross-linked to reduce infiltration of the layer by water molecules from the sample under test.

The optimum thickness of the dielectric layer will depend on numerous factors including the particular material used but in general satisfactory results are obtained with a layer of thickness 0.5 to 5 microns, typically 1 to 3 microns. The dielectric layer is mechanically stiff to couple to the motion of the support and sufficiently dense to minimise waves lost to the support.

The dielectric layer can be derivatised or activated to facilitate immobilisation thereon of suitable binding reagents for the analyte(s) under test. Such reagents include, for biological samples, antibodies or antigens, and for other chemical applications such species as crown ethers (for the determination of particular ionic species).

In preferred embodiments, surface acoustic wave sensors of the present invention comprise a dielectric layer covering all or a portion of the input and output transducers and the piezoelectric surface. The dielectric layer generally serves two purposes. The first is to shield the input and output transducers from the sample fluid. The second is to act as a waveguide to direct the propagating surface acoustic wave. The polymer layer may comprise any material that serves the above two purposes. In preferred embodiments, the polymer layer comprises $SiO_2$ or polyimide or gold or a combination of $SiO_2$ and gold.

C. Input and Output Transducer(s)

The input and output transducers are preferably interdigitated transducers. Generally, there are two interdigital transducers. Each of the input and output transducers comprises two electrodes arranged in an interdigitated pattern. A voltage difference applied between the two electrodes of the input transducer results in the generation of a surface acoustic wave in the piezoelectric substrate. The electrodes generally may comprise any conductive material, with aluminum or gold being preferred.

The electrode(s) may take any conventional form but are preferably photolithographically deposited on the surface as elongate regions of metallisation transverse to the direction of propagation of a wave along the surface of the support. The elongate metallised regions preferably have a width and spacing of the same order of magnitude. The width is typically between 1 and 40 microns, preferably between 10 and 20 microns. In certain embodiments, the width is greater than or equal to 100 nm, 200 nm, 300 nm, 400 nm, 500 nm, 600 nm, 700 nm, 800 nm, 900 nm, 1 micron, 2 microns, 3 microns, 4 microns, 5 microns, 7.5 microns, 10 microns, 15 microns, 20 microns, 25 microns, 30 microns, 35 microns, 40 microns, 45 microns, 50 microns, 60 microns, 70 microns, 80 microns or 90 microns. In other embodiments, the space between the electrodes can be equal to or less than 100 microns, 90 microns, 80 microns, 70 microns, 60 microns, 50 microns, 45 microns, 40 microns, 35 microns, 30 microns, 25 microns, 20 microns, 15 microns, 10 microns, 7.5 microns, 5 microns, 4 microns, 3 microns, 2 microns 1 microns, 900 nm, 800 nm, 700 nm, 600 nm, 500 nm, 400 nm, 300 nm, 200 nm, 100 nm, or 75 nm. It should be noted that the spacing varies inversely with the frequency of the device.

In certain embodiments, the height of the electrodes is the same as the width of the electrodes. In other embodiments, the height of the electrodes is, for example, greater than or equal to 10 nm, 20 nm, 30 nm, 40 nm, 50 nm, 75 nm, 100 nm, 200 nm, 300 nm, 400 nm, 500 nm, 600 nm, 700 nm, 800 nm, or 900 nm. In other embodiments, the depth of the space between the electrodes can be less than or equal to 1 micron, 900 nm, 800 nm, 700 nm, 600 nm, 500 nm, 400 nm, 300 nm, 200 nm, 100 nm, 75 nm, 50 nm, 40 nm, 30 nm, or 20 nm.

In an alternative embodiment there is a single interdigital transducer. In this embodiment the single interdigital transducer, serves both as both an input and output transducer. In embodiments employing a single interdigital transducer acting as both input and output transducer, a reflector structure is generally provided to generate one or more resonances within the SAW sensor. The reflector structure may, for example, be a thin film grating. The grating may comprise aluminum, or another conductive material. The generated resonances can be detected, for example, by measuring the power dissipated at the single transducer. One or more binding events in the thin structure alter these resonances, allowing the binding events to be detected. An example of a sensor and technique according to this embodiment is generally described in U.S. Pat. No. 5,846,708, hereby incorporated by reference. As described below, other electronics and/or circuitry may similarly be utilized in an embodiment employing a SAW sensor having only one interdigital transducer.

Molecular recognition molecules may be attached directly to self-assembled monolayers. For example, when gold electrodes are employed, a DNA probe molecule may be attached using a SH group on the 5' of the DNA using self-assembled monolayers as known in the art and described, for example, in K. Vijayamohanan et al. "Self-assembled monolayers as a tunable platform for biosensor applications," Biosensors & Bioelectronics 17 (2002) 1-12 and George M. Whitesides et al. "Array of Self-Assembled Monolayers for studing inhibition of Bacterial Adhesion." Anal Chem 2002, 74, 1805-1810, both of which are hereby incorporated by reference.

D. Hydrogels

In the SAW sensors of the present application, a molecular recognition component is immobilized in a hydrogel. The word "hydrogel" refers to a colloid gel in which particles are dispersed in water and cross-linked. The hydrogel forms a thin film, i.e. between about 1 nm and several millimiters. In a preferred embodiment, the hydrogel has a thickenss that is co-extensive with the depth of the channel in the IDT. When a target analyte binds the molecular recognition component, a change in the phase and/or the frequency of the hydrogel occurs.

In certain embodiments, the hydrogel is coextensive with the electrodes, not exceeding the electrode height. In certain other embodiments, the hydrogel exceeds the height of the electrodes. In other embodiments, the hydrogel is less than the height of the electrodes.

Without being limited a specific mechanism, the change in the hydrogel can be a change in volume, dimension, or conformation.

The hydrogel can be comprised any number of molecules. For example, the hydrogel can comprise a polymerized monomer or hydrogel a cross linking agent and optionally a chemical or UV-light activated inducer agent. Non-limiting examples of such monomers or dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycol-dimethacrylate, N,N'-methylenebisacrylamide, polyethyleneglycoldiacrylate(PEGDA), polyethyleneglycoldimethacrylate(PEGDMA), polyethyleneglycoldiacrylate(PEGDA), polyethyleneglycoldimethacrylate (PEGDMA), poly(vinyliden fluoride)(PVdF) based polymer, a polyacrylonitrile(PAN) based polymer, a polymethylmethacrylate(PMMA) based polymer, a polyvinyl chloride (PVC) based polymer, and a mixture of the poly(vinyliden fluoride)(PVdF) based polymer, polyacrylonitrile(PAN) based polymer, polymethylmethacrylate(PMMA) based polymer, and polyvinyl chloride(PVC) based polymer, and mixtures therof.

Cross linking agent and optionally the chemical or UV-light activated inducer agent can include N,N'-methylenebisacrylamide, methylenebismethacrylamide ethyleneglycoldimethacrylate and agent N,N'-methylenebisacrylamide. Irgacure 2959 (Ciba); 2,2-dimethoxy-2-phenylacetophenone, 2-methoxy-2-phenylacetone, benzyl-dimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1, 1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyltioxantone, chloro tioxantone, 2,2-chlorobenzophenone, benzyl benzoate, and benzoyl benzoate, TEMED, and ammonium persulfate (APS).

In one aspect, the hydrogel is acrylamide. Acrylamide ($CH_2$=$CHCONH_2$; C.A.S. 79-06-1; also known as acrylamide monomer, acrylic amide, propenamide, and 2-propenamide) is an odorless, free-flowing white crystalline substance that is used as a chemical intermediate in the production and synthesis of polyacrylamides. These high molecular weight polymers have a variety of uses and further can be modified to optimize nonionic, anionic, or cationic properties for specified uses.

A molecular recognition component is added to the hydrogel prior to formation. The concentration of hydrogel can be any concentration capable of forming the hydrogel. For example, a acrylamide polymerization solution that is 0.6-0.7% acrylamide/bisacrylamide 19/1 in water/glycerol is used, with a nominal amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature (e.g., typically at about 40° C.). Polymerization is obtained between the electrodes. The pore size (or "sieving properties") of the gel is controlled by changing the amount of crosslinker and the % solids in the monomer solution. The pore size also can be controlled by changing the polymerization temperature.

Exemplary pore size can be greater than or equal to 0.5 nm, 1 nm, 2 nm, 3 nm, 4 nm, 5 nm, 7 nm, 10 nm, 20 nm, 30 nm, 40 nm, 50 nm, 75 nm, 100 nm, 200 nm, 300 nm, 400 nm, 500 nm, 600 nm, 700 nm, 800 nm, 900 nm, 1 micron, 1.25 microns, 1.5 microns, 1.75 microns, 2 microns, 2.5 microns, or 3 microns. Exemplary pore sizes can also be equal to or less than 3 microns, 2.5 microns, 2 microns, 1.5 microns, 1 micron, 900 nm, 800 nm, 700 nm, 600 nm, 500 nm, 400 nm, 300 nm, 200 nm, 100 nm, 75 nm, 50 nm, 40 nm, 30 nm, 20 nm, 10 nm, 7 nm, 5 nm, 4 nm, 3 nm2 nm, or 1 nm.

Following fabrication of the hydrogel array, the polyacrylamide subsequently is modified to include functional groups for the attachment of moieties, and the moieties (e.g., DNA) later are attached.

E. Molecular Recognition Components

Molecular recognition components that detect any analyte are immobilized within the hydrogel.

Molecular recognition components can be any molecule capable of binding or bonding to a target analyte. Molecular recognition components can be specific to detecting biological compounds. Exemplary molecular recognition components include nucleic acids, nucleotide, nucleoside, nucleic acids analogues such as PNA and LNA molecules, proteins, peptides, antibodies including IgA, IgG, IgM, IgE, enzymes, enzymes cofactors, enzyme substrates, enzymes inhibitors, membrane receptors, kinases, Protein A, Poly U, Poly A, Poly lysine, triazine dye, boronic acid, thiol, heparin, membrane receptors, polysaccharides, coomassie blue, azure A, metal-binding peptides, sugar, carbohydrate, chelating agents, prokaryotic cells and eukaryotic cells. In certain embodiments, multiple molecular recognition components are included. The target analyte can be capable of binding more than one molecular recognition component.

In one variation, the molecular recognition component can be covalently bonded to the piezoelectric surface. Further, in an application of lithographic techniques known in the semiconductor industry, light can be applied to discrete locations on the surface of a polyacrylamide hydrogel to activate these specified regions for the attachment of a molecular recognition component, such as an antibody or antigen, hormone or hormone receptor, oligonucleotide, or polysaccharide on the surface (e.g., a polyacrylamide hydrogel surface) of a solid support (PCT International Application WO 91/07087, incorporated by reference).

FIG. 16 depicts a schematic drawing of the IDTs on the SAW resonator surface. The IDT structures 1a-1c are constructed from gold, and have a silicon oxide coating. Electrode 1b is disposed between electrodes 1a and 1c. Electrodes 1a and 1c alternate in frequency with respect to electrode 1b. The hydrogel 4 includes molecular recognition particles immobilized therein. Surface acoustic wave 2 is generated by piezoelectric material 4.

FIG. 17 shows an atomic force microscopy (AFM) picture of the SAW resonator surface structures. It is believe that the hydrogel/antibody solution are polymerising down between the IDT structures since the concentration of oxygen (inhibitor of polymerisation) are low at this location. In this embodiment, the spacing between the IDT structures is approx 1500 nm. In the present embodiment, the height of the IDT structure is approx 200 nm as illustrated at FIG. 16.

FIG. 18 depicts the IDTs having a hydrogel with immobilized antibodies as the molecular recognition component. Electrodes 4a-4c rest on piezoelectric material 6. Silicon oxide coating 8 is disposed on the piezoelectric material 6 and the electrodes 4a-4c. Hydrogel 1 is disposed on and in between electrodes 4a-4c. Antibodies 2, the molecular recognition components in this embodiment, are contained within hydrogel 1. FIG. 19 shows the SAW sensor and hydrogel of FIG. 18 with target analytes 10 bound by the antibodies 2.

II. Methods of Using the SAW Sensor

Generally, in the case of a single, active SAW sensor, an electronic input signal having an frequency and phase is applied to an input transducer. An output signal having a second amplitude, frequency, and phase is detected at an output transducer. A binding event can be detected by monitoring—continuously or at predefined times—the output signal before and after binding the target analyte. A shift in the frequency or phase of the output signal indicates a binding event.

This detection method may be extended in other embodiments to cases where more that one sensor is employed. For example, the signal of a SAW sensor may be compared to a reference sensor.

Reference sensors are generally structured similar to the sensing sensor just not having the molecular recognition component integrated in the hydrogel matrix, but are designed to generate a reference output signal corresponding to a baseline output signal indicative of the absence of binding events.

Reference sensors may be integrated with one or more active sensors. For example, a reference sensor may be formed on the same substrate as an active sensor. A reference sensor may further be formed on the same piezoelectric layer as an active sensor. Alternatively, a reference sensor may be forined independent of any active sensors, and merely operatively associated with an active sensor through electronic detection circuitry. Surface acoustic wave filters are available commercially. For example, SAW filters manufactured by MuRaTa, type SAF380F are particularly preferred for adaptation for use in the present invention.

In other embodiments, one or more sensor output signals may be compared to indicate a binding event. A discussed above, one or more output signals from active devices may further be compared to an output signal from a reference sensor. When a similar input signal had been applied to an active and a reference sensor, a direct comparison between properties of output signals may reliably indicate a binding event.

In other embodiments, those having skill in the art will appreciate that a variety of signal processing techniques may be employed to design one or more input signals and process output signals obtained from one or more sensors for reliable identification of a binding event.

Appropriate circuitry may be provided in association with the input and output transducers to generate input signals, detect, and compare output signals. This includes, for example, differential amplifiers, oscillators, oscillator circuits employing the SAW sensor as a frequency determination element, signal generators, network analyzers, voltmeters, multimeters, as well as other amplifying, frequency detecting, conditioning, control, and differential circuitry as known in the art. As appropriate, circuitry may be integrated with one or more sensors, or merely operatively associated with a sensor.

Preferably, the surface acoustic wave sensors of the invention are positioned in a channel or chamber in, for example, a microfluidic device. The channel or chamber has inlet or outlet ports that allow for the introduction of samples into the channel or chamber for analysis of target samples. In one embodiment, the sample may be separated, for example, into different channels or chambers for separate analysis. That is, in one embodiment multiple samples can be analysed simultaneously. In an alternative embodiment multiple target analytes can be analysed from a single sample. That is, a plurality of discrete microsensors may be contained within a single chamber. In this embodiment the individual microsensors are used to detect discrete target analytes from a single sample.

III. Target Analytes

The surface acoustic wave sensor of the invention is used to detect target analytes in samples. By "target analyte" or "analyte" or "chemical species" grammatical equivalents herein is meant any molecule, compound or particle to be detected. As outlined below, target analytes preferably bind to molecular recognition components, as is more fully described herein. Preferably the molecular recognition components are immobilized with the hydrogel. As will be appreciated by those in the art, a large number of analytes may be detected using the present methods; basically, any target analyte, for which a molecular recognition component exists, may be detected using the methods and apparatus of the invention.

Suitable analytes include organic and inorganic molecules, as well as biomolecules. In a preferred embodiment, the analyte may be an environmental pollutant (including heavy metals, pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc)(detection of antigen antibody interactions are described in U.S. Pat. Nos. 4,236,893, 4,242,096, and 4,314,821, all of which are expressly incorporated herein by reference); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte and molecular recognition components are nucleic acids. By "nucleic acid" or "oligonucleotide" or grammatical equivalents herein means at least two nucleotides covalently linked together.

In a preferred embodiment, the present invention provides methods of detecting target nucleic acids. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA, rRNA, siRNA, and others. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. Target sequences also include the result or product of an amplification reaction, i.e. amplicons.

A nucleic acid of the present invention will generally contain phosphodiester bonds, although in some cases, as outlined below, nucleic acid analogs that may have alternate backbones may be used. Preferably, the nucleic acid target analyte is a polynucleotide. Nucleic acid analogs are preferably used, if at all, as immobilized probes (molecular recognition component) in the hydrogel on the surface of a microsensor. Such nucleic acid analytes have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470

(1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169-176). In addition, locked nucleic acids (LNA) find use in the invention. LNA are described in more detail in Wengel et al.; J. Org Chem 63; 10035-9 1998, which is expressly incorporated herein by reference. Several nucleic acid analogs are described in Rawls, C & E News Jun. 2, 1997 page 35. All of these references are hereby expressly incorporated by reference. These modifications of the ribose-phosphate backbone may be done to facilitate the addition of labels or to increase the stability and half-life of such molecules in physiological environments.

Particularly preferred are Locked nucleic acids (LNA) described in U.S. Pat. No. 6,670,461.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids whether a target nucleic acid, probe or elongation product, for example of a polymerase or a ligase, may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As is outlined more fully below, probes (including amplification primers) are made to hybridize to target sequences to determine the presence or absence of the target sequence in a sample. Generally speaking, this term will be understood by those skilled in the art.

The target sequence may also be comprised of different target domains, for example, in "sandwich" type assays as outlined below, a first target domain of the sample target sequence may hybridize to an immobilized probe or primer on a microsensor, and a second target domain may hybridize to a solution-phase probe or primer. In addition, the target domains may be adjacent (i.e. contiguous) or separated. For example, when ligation techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below. In such cases, at least one of the primers is immobilized in the Hydrogel of the microsensor and a ligase is used to covalently join the probe.

In another preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. As discussed below, when the protein is used as a molecular recognition component, it may be desirable to utilize protein analogs to retard degradation by sample contaminants.

These target analytes may be present in any number of different sample types, including, but not limited to, bodily fluids including blood, lymph, saliva, vaginal and anal secretions, urine, feces, perspiration and tears, and solid tissues, including liver, spleen, bone marrow, lung, muscle, brain, etc.

Accordingly, the present invention provides a single or multi-component devices for the detection of target analytes. As noted above, the device includes a detection channel or chamber that includes at least one active microsensor and may preferably contain at least 4, 5, 10, 20, 30, 40, 50 or 100 active microsensors. In a preferred embodiment the chamber includes at least 100 microsensors. As described herein, the microsensors are coupled to a detector.

In one embodiment the device includes a single channel or chamber for the amplification and detection of target nucleic acids. Alternatively, the device may comprise more than one channel or chamber; for example, there may be a "sample treatment" or "sample preparation" channels or chambers that interfaces with a separate "detection" channel or chamber. By "channel" is meant a path or trough through which a sample flows, generally between chambers, although in some embodiments reactions can occur in the channels themselves. By "chamber" is meant a closed or closeable portion of the microfluidic device in which samples are manipulated and/or detected. While much of the discussion below emphasizes reactions occurring in chambers, it is appreciated that any of the reactions or manipulations also can occur in channels.

Generally, when nucleic acids are to be detected and nucleic acids serve as the probes or primers, two general schemes find use in the invention. In one embodiment the target analyte is amplified to produce amplicons. Amplicons are then detected with the microsensor. In another embodiment, the target analyte hybridizes with the probe or primer immobilized in the hydrogel matrix on the microsensor. The probe or primer is modified and the modification, which generally includes a change in properties of the hydrogel, is detected. As one of skill in the art appreciates, "target analytes" can include both targets from samples or products of an amplification reaction, i.e. amplicons. That is, amplicons can serve as target analytes. The immobilized probe can then be modified as a result of hybridization with the amplicons.

Alternatively, specific hybridization of a target with the immobilized probe on the sensor results in a detectable change in an actual or differential sensor output signal.

As noted previously, detection of target analytes can occur by hybridization of a target to a probe immobilized in the hydrogel matrix. Detection also can occur by detecting a modification of the immobilized probe or primer. This results in the formation of a "modified primer". While there are a variety of types of modifications, generally modifications that find use in the present invention are those that result in a change in mass of the immobilized probe or primer. That is, in general the probe or primer will be modified by extension such as by a DNA polymerase or ligase. Sandwich assays also find use in detection of target analytes.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay. Sandwich assays are described in U.S. Ser. No. 60/073, 011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In addition these target sequences can be used as templates for other assays that result in modification of the immobilized primers.

Single Base Extension (SBE) is an extension assay that results in the incorporation of a nucleotide into a primer sequence when the primer sequence is complementary to or hybridized with a target sequence. The nucleotide incorporated into the primer is complementary to the nucleotide at the corresponding position of the target nucleic acid. Accordingly, the immobilized primer in the hydrogel is extended, i.e. modified, and is detected by the device of the invention. As such, detection of a change in the immobilized primer is an indication of the presence of the target analyte.

In addition, just as primer extension can be detected on the microsensor, sequencing can be performed on the microsensor. When primer extension is performed, the detector detects an changes of the hydrogel dimensions that is indicative of the addition of a nucleotide. When sequencing is performed, each nucleotide that is added to the primer is detected on the microsensor. That is, the detector detects which nucleotide is added to the primer. As such, the sequence of the target can be obtained. In some embodiments, nucleotides are added to the primer extension reaction one at a time. In this embodiment, upon detecting an increase in mass on the microsensor, the sequence also is determined. In an alternative embodiment, the nucleotides are tagged or labeled with particles, i.e. gold particles, of characteristic mass. That is, each of the nucleotides is tagged with a label of discrete mass that is indicative of the particular nucleotide, due to specific changes of the hydrogel properties (dimensions).

In some embodiments, when the tag prevents subsequent primer extension, the tagged nucleotides are added in combination with untagged nucleotides. This way, a population of primers will be extended with tagged nucleotides while a population will be extended with untagged nucleotides that are available for additional extension. In this way, the sequence of the target nucleic acid is obtained.

Oligonucleotide-ligation assay is an extension of PCR-based screening that uses an ELISA-based assay (OLA, Nickerson et al., Proc. Natl. Acad. Sci. USA 87:8923, 1990) to detect the PCR products that contain the target sequence. Briefly, the OLA employs two adjacent oligonucleotides: a "reporter" probe and an "anchor" probe. The two oligonucleotides are annealed to target DNA and, if there is perfect complementarity, the two probes are ligated by a DNA ligase. The ligated probe is then captured by the probe on the SAW sensor.

Alternatively, one of the OLA primers is immobilized in the hydrogel matrix on the microsensor. Upon ligation, the mass on the microsensor is increased. The mass increase is detected as an indication of the presence of the target analyte.

In this and other embodiments, a heating and/or cooling module may be used, that is either part of the reaction chamber or separate but can be brought into spatial proximity to the reaction module. Suitable heating modules are described in U.S. Pat. Nos. 5,498,392 and 5,587,128, and WO 97/16561, incorporated by reference, and may comprise electrical resistance heaters, pulsed lasers or other sources of electromagnetic energy directed to the reaction chamber. It should also be noted that when heating elements are used, it may be desirable to have the reaction chamber be relatively shallow, to facilitate heat transfer; see U.S. Pat. No. 5,587,128.

IV. Peripheral Components

In one embodiment, the devices of the invention includes a separate detection module. That is, when the reaction channel or chamber does not include the microsensors, a separate detection channel or chamber is needed. It should be noted that the following discussion of detection modules is applicable to the microsensor when the microsensors are found in the reaction channel or chamber.

Accordingly, the present invention is directed to methods and compositions useful in the detection of biological target analyte species such as nucleic acids and proteins. In general, the detection module is based on binding partners or bioactive agents incorporated in SAW sensors as described herein.

That is, each microsensor comprises a bioactive agent. By "candidate bioactive agent" or "bioactive agent" or "chemical functionality" or "molecular recognition component" herein is meant any molecule, e.g., protein, oligopeptide, small organic molecule, coordination complex, polysaccharide, polynucleotide, etc. which can be attached to a microsensor. Preferred bioactive agents include biomolecules including peptides, nucleic acids, saccharides, fatty acids, steroids, purines, pyrimidines, derivatives, structural analogs or combinations thereof. Particularly preferred are nucleic acids and proteins.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred.

In a preferred embodiment, the bioactive agents are nucleic acids as defined above (generally called "probe nucleic acids", "primers" or "candidate probes" herein). As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

When the bioactive agents are nucleic acids, they are designed to be substantially complementary to target sequences. As noted above, the term "target sequence" or grammatical equivalents herein means a nucleic acid sequence on a single strand of nucleic acid.

A probe nucleic acid (also referred to herein as a primer nucleic acid) is then contacted with the target sequence to form a hybridization complex. Generally, the probe nucleic acid is immobilized in the hydrogel matrix. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the probe or primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on what is required for detection and/or amplification as is discussed below.

In a preferred embodiment, each microsensor comprises a single type of bioactive agent, although a plurality of individual bioactive agents are preferably attached in the hydrogel matrix on each microsensor, as described herein. In addition, as described above, the microsensor is in communication with a detector such that the presence of the target analyte can be determined.

In a preferred embodiment, the devices of the invention include a reaction module. This can include physical, chemical or biological alteration of one or more sample components. Alternatively, it may include a reaction module wherein the target analyte alters a second moiety that can then be detected; for example, if the target analyte is an enzyme, the reaction chamber may comprise a substrate that upon modification by the target analyte, can then be detected by binding to a microsensor. In this embodiment, the reaction module may contain the necessary reagents, or they may be stored in a storage module and pumped as outlined herein to the reaction module as needed.

Alternatively, the target analyte serves as a substrate for an enzymatic reaction such as a polymerase or ligase extension reaction, but the target itself is not altered or consumed. Rather, the immobilized probe or primer in the microsensor is modified in a template or target analyte dependent manner.

In a preferred embodiment, the reaction module includes a chamber for the chemical modification of all or part of the sample before or during analyte detection. That is, in one embodiment there is a separate reaction module and a separate detection module. In an alternative embodiment the reaction occurs in the detection module. This allows for simultaneous modification and detection of analytes.

Chemical modifications include, but are not limited to chemical cleavage of sample components (CNBr cleavage of proteins, etc.) or chemical cross-linking. PCT US97/07880, hereby incorporated by reference, lists a large number of possible chemical reactions that can be performed in the devices of the invention, including amide formation, acylation, alkylation, reductive amination, Mitsunobu, Diels Alder and Mannich reactions, Suzuki and Stille coupling, etc. Similarly, U.S. Pat. Nos. 5,616,464 and 5,767,259 describe a variation of ligation chain reaction (LCR; sometimes also referred to as oligonucleotide ligation amplification or OLA) that utilizes a "chemical ligation" of sorts.

In a preferred embodiment, the reaction module includes a chamber for the biological alteration of all or part of the sample before or during analyte detection. For example, enzymatic processes including nucleic acid amplification and other nucleic acid modifications including ligation, cleavage, circularization, supercoiling, methylation, acetylation; hydrolysis of sample components or the hydrolysis of substrates by a target enzyme, the addition or removal of detectable labels, the addition or removal of phosphate groups, protein modification (acylation, glycosylation, addition of lipids, carbohydrates, etc.), the synthesis/modification of small molecules, etc.

Alternatively, the modification or alteration may occur in the immobilized primer as a result of hybridization with the target molecule.

In a preferred embodiment, the target analyte is a nucleic acid and the biological reaction chamber allows amplification of the target nucleic acid. Suitable amplification techniques include polymerase chain reaction (PCR), reverse transcriptse PCR (RT-PCR), ligase chain reaction (LCR), and Invader.™. technology. Techniques utilizing these methods are well known in the art. In this embodiment, the reaction reagents generally comprise at least one enzyme (generally polymerase), primers, and nucleoside triphosphates as needed. As described herein, the amplification reactions can occur in a chamber or channel separate from the detection chamber. Alternatively, the amplification can occur in the detection chamber. As amplification proceeds, the amplicons hybridize to the immobilized probe in the hydrogel matrix on the microsensor in the detection chamber resulting in a detectable change in a property of the microsensor as outlined herein.

Alternatively, the amplicons serve as templates for subsequent reactions that result in a modification of the immobilized primer. Such modifications are discussed more fully below and include primer extension that results in lengthening the primer. Also, the primer can be ligated to another probe or primer such that the immobilized primer is lengthened.

General techniques for nucleic acid amplification are discussed below. In most cases, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques such as the use of extra probes or nucleic acid binding proteins may also be used. In one embodiment isothermal amplification is preferred.

In addition, the different amplification techniques may have further requirements of the primers, as is more fully described below.

Once the hybridization complex between the primer and the target sequence has been formed, an enzyme, sometimes termed an "amplification enzyme", is used to modify the immobilized primer. As for all the methods outlined herein, the enzymes may be added at any point during the assay, either prior to, during, or after the addition of the primers. The identification of the enzyme will depend on the amplification technique used, as is more fully outlined below. Similarly, the modification will depend on the amplification technique, as outlined below, although generally the first step of all the reactions herein is an extension of the primer, that is, nucleotides or oligonucleotides are added to the primer to extend its length.

In some embodiments, once the enzyme has modified the primer to form a modified primer, the hybridization complex is disassociated. By "modified primer" is meant a primer that has been changed or altered in a detectable manner. Generally a modified primer is lengthened by the addition of at least one nucleotide.

In an alternative embodiment proteins are the target molecules and are detected by protein affinity agents that include a nucleic acid to be amplified. By "affinity agent" is meant a molecule that binds with high affinity to the target protein. Affinity agents can include, but are not limited to aptamers, antibodies, ligands, adapter proteins, lectins, and the like. In this embodiment the affinity agent is coupled to a nucleic acid.

After a binding reaction between the protein target and the affinity agent, the unbound affinity agents are removed. Agents can be removed by methods as known in the art, such as by washing. In this embodiment it is preferable for the complexes to be immobilized so that the unbound molecules can be washed away. Once removed, the nucleic acids are amplified and the resulting amplicons are detected by hybridization to immobilized probes on the SAW sensor as described herein. Alternatively the nucleic acids are not themselves amplified, but serve to hybridize with a circular probe. The circular probe is a template for Rolling Circle Amplification. This is described in more detail in Nature Biotechnology, April, 2002, vol. 20, pp359-365, which is expressly incorporated herein by reference. Following the Rolling Circle Amplification, the amplicons again are detected on the SAW sensor as described herein.

Thus, for both protein detection and nucleic acid detection amplification of nucleic acids may occur prior to detection of the target molecule. During amplification generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

In one embodiment, after a suitable time or amplification, the amplicon is moved to a detection module and incorporated into a hybridization complex with a probe immobilized in the hydrogel matrix on the surface of a microsensor as is more fully outlined below. The hybridization complex is attached to a microsensor and detected, as is described below.

In an alternative embodiment, amplification occurs in the detection chamber (described more fully below). That is, amplification and detection occur in the same chamber. In one embodiment amplification proceeds by using at least two solution phase primers. Following amplification, amplicons hybridize with probes or primers immobilized in the hydrogel matrix of the microsensor to form hybridization complexes. Upon hybridization with the immobilized probe, the presence of the target analyte is detected. In a preferred embodiment, the hybridization complex is used as a template for further reactions that result in the modification of the immobilized probe. Such reactions include extension reactions such as single base extension (SBE), template dependent nucleic acid synthesis or the oligonucleotide ligation assay (OLA) described in more detail herein.

In an alternative embodiment amplification and primer extension proceeds by the use of a solution-phase primer and a primer immobilized on the surface of the microsensor.

In yet another alternative embodiment, amplification proceeds by the use of primer pairs immobilized in the hydrogel matrix of the microsensor. That is, both amplification primers are immobilized in the hydrogel matrix of the microsensor. As such, upon amplification of the target analyte, the amplicons also are immobilized in the hydrogel matrix of the microsensor.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), and nucleic acid sequence based amplification (NASBA) and the ligase chain reaction (LCR).

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP". "reverse transcriptase PCR" or "RT-PCR", "biotin capture PCR", "vectorette PCR", "panhandle PCR", and "PCR select cDNA subtration", among others.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostable polymerase such as Taq I polymerase and thermal cycling. In an alternative embodiment isothermal amplification is used.

Accordingly, the PCR reaction requires at least one PCR primer and a polymerase. Mesoscale PCR devices are described in U.S. Pat. Nos. 5,498,392 and 5,587,128, and WO 97/16561, incorporated by reference.

In a preferred embodiment the amplification is RT-PCR. Preferably the reaction includes either two-step RT-PCR or solid phase RT-PCR. In this embodiment RT-PCR can be performed using either solution phase primers or immobilized primers as described above. In this embodiment mRNA is reverse transcribed to cDNA and PCR is conducted by using DNA polymerase. Again PCR primers can be solution-phase or immobilized as described above.

In an additional preferred embodiment, re-amplification of cDNA (multiple-PCR system) is performed. cDNA synthesized from mRNA can be used more than once. Preferably, the cDNA is immobilized as this increases the stability of the cDNA. This allows reamplification of the same immobilized cDNA such that different or the same target sequences can be amplified multiple times. As noted above, amplification can use solution-phase primers or immobilized primers and detection of amplicons proceeds following hybridization of amplicons to the probe immobilized in the hydrogel matrix of on the microsensor.

In a preferred embodiment the RT-PCR amplification is a high throughput RT-PCR system.

In a preferred embodiment, the amplification technique is LCR. The method can be run in two different ways; in a first embodiment, only one strand of a target sequence is used as a template for ligation; alternatively, both strands may be used. See generally U.S. Pat. Nos. 5,185,243 and 5,573,907; EP 0 320 308 B1; EP 0 336 731 B 1; EP 0 439 182 B1; WO 90/01069; WO 89/12696; and WO 89/09835, and U.S. Ser. Nos. 60/078,102 and 60/073,011, all of which are incorporated by reference.

In a preferred amplification embodiment, the single-stranded target sequence comprises a first target domain and a second target domain. A first LCR primer and a second LCR primer nucleic acids are added, that are substantially complementary to its respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two LCR primers are then covalently attached, for example using a ligase enzyme such as is known in the art. This forms a first hybridization complex comprising the ligated probe and the target sequence. This hybridization complex is then denatured (disassociated), and the process is repeated to generate a pool of ligated probes, i.e. amplicons. The ligated probes or amplicons are then detected with the probe immobilized in hydrogel matrix of the microsensor.

In a preferred embodiment, LCR is done for two strands of a double-stranded target sequence. The target sequence is denatured, and two sets of primers are added: one set as outlined above for one strand of the target, and a separate set (i.e. third and fourth primer nucleic acids) for the other strand of the target. In a preferred embodiment, the first and third primers will hybridize, and the second and fourth primers will hybridize, such that amplification can occur. That is, when the first and second primers have been attached, the ligated product can now be used as a template, in addition to the second target sequence, for the attachment of the third and fourth primers. Similarly, the ligated third and fourth products will serve as a template for the attachment of the first and second primers, in addition to the first target strand. In this way, an exponential, rather than just a linear, amplification can occur.

Again, as outlined above, the detection of the LCR products can occur directly, in the case where one or both of the primers simply hybridize with a primer immobilized in the hydrogel on the microsensor; hybridization is detected as described herein. Alternatively, detection of LCR products can occur indirectly using sandwich assays, through the use of additional probes; that is, the ligated products can serve as target sequences, and detection proceeds via hybridization to probes or primers immobilized on the surface of the microsensor.

In addition, the device may include other modules such as sample preparation chambers. In this embodiment, a crude sample is added to the sample treatment channel or chamber and is manipulated to prepare the sample for detection. The manipulated sample is removed from the sample treatment channel or chamber and added to the detection chamber. There may be additional functional elements into which the device fits; for example, a heating element may be placed in contact with the sample channel or chamber to effect reactions such as PCR. In some cases, a portion of the device may be removable; for example, the sample chamber may have a detachable detection chamber, such that the entire sample chamber is not contacted with the detection apparatus. See for example U.S. Pat. No. 5,603,351 and PCT US96/17116, hereby incorporated by reference.

In addition to different channels or chambers, the device may also include one or more flow cells or flow channels allowing sample movement between chambers. In addition to flow channels, there also may be inlet ports and outlet ports separating chambers. Such ports allow for samples to be contained in different chambers without cross-contamination.

In some embodiments the device also includes a pump mechanism that hydrodynamically pumps the samples through the device. Alternatively a vacuum device is used.

In a preferred embodiment, the microfluidic device can be made from a wide variety of materials, including, but not limited to, silicon such as silicon wafers, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, brass, sapphire, etc.

The microfluidic devices of the invention can be made in a variety of ways, as will be appreciated by those in the art. See for example WO96/39260, directed to the formation of fluid-tight electrical conduits; U.S. Pat. No. 5,747,169, directed to sealing; and EP 0637996 B1; EP 0637998 B1; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are hereby incorporated by reference. Suitable fabrication techniques again will depend on the choice of substrate, but preferred methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding, and bonding techniques (see U.S. Pat. No. 5,747,169, hereby incorporated by reference). In addition, there are printing techniques for the creation of desired fluid guiding pathways; that is, patterns of printed material can permit directional fluid transport.

In a preferred embodiment, the device is configured for handling a single sample that may contain a plurality of target analytes. That is, a single sample is added to the device and the sample may either be aliquoted for parallel processing for detection of the analytes or the sample may be processed serially, with individual targets being detected in a serial fashion.

In a preferred embodiment, the solid substrate is configured for handling multiple samples, each of which may contain one or more target analytes. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection array, as described below.

Thus, the multi-chamber devices of the invention include at least one microchannel or flow channel that allows the flow of sample from the sample inlet port to the other components or modules of the system. The collection of microchannels and wells is sometimes referred to in the art as a "mesoscale flow system". As will be appreciated by those in the art, the flow channels may be configured in a wide variety of ways, depending on the use of the channel. For example, a single flow channel starting at the sample inlet port may be separated into a variety of different channels, such that the original sample is divided into discrete subsamples for parallel processing or analysis. Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used; similarly, longer lengths for separation purposes may also be desirable.

In general, the microfluidic devices of the invention are generally referred to as "mesoscale" devices. The devices herein are typically designed on a scale suitable to analyze microvolumes, although in some embodiments large samples (e.g. cc's of sample) may be reduced in the device to a small volume for subsequent analysis. That is, "mesoscale" as used herein refers to chambers and microchannels that have cross-sectional dimensions on the order of 0.1 microns to 500 microns. The mesoscale flow channels and wells have preferred depths on the order of 0.1 microns to 100 microns, typically 2-50 microns. The channels have preferred widths on the order of 2.0 to 500 microns, more preferably 3-100 microns. For many applications, channels of 5-50 microns are useful. However, for many applications, larger dimensions on the scale of millimeters may be used. Similarly, chambers in the substrates often will have larger dimensions, on the scale of a few millimeters.

In addition to the flow channel system, the microdevice may be configured to include one or more of a variety of components, herein referred to as "modules," that will be present on any given device depending on its use. These modules include, but are not limited to: sample inlet ports; sample introduction or collection modules; cell handling modules (for example, for cell lysis, cell removal, cell concentration, cell separation or capture, cell fusion, cell growth, etc.); separation modules, for example, for electrophoresis, gel filtration, sedimentation, etc.); reaction modules for chemical or biological alteration of the sample, including amplification of the target analyte (for example, when the target analyte is nucleic acid, amplification techniques are useful, including, but not limited to polymerase chain reaction (PCR), ligase chain reaction (LCR), strand displacement amplification (SDA), chemical, physical or enzymatic cleavage or alteration of the target analyte, or chemical modification of the target; fluid pumps; fluid valves; heating modules; storage modules for assay reagents; mixing chambers; and detection modules.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well or chamber. Alternatively, for example, when there is a single chamber, the sample inlet port may be configured such that samples are introduced into the single chamber for amplification and/or detection.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the devices of the invention include a cell handling module. This is of particular use when the sample comprises cells that either contain the target analyte or that are removed in order to detect the target analyte. Thus, for example, the detection of particular antibodies in blood can require the removal of the blood cells for efficient analysis, or the cells must be lysed prior to detection. In this context, "cells" include viral particles that may require treatment prior to analysis, such as the release of nucleic acid from a viral particle prior to detection of target sequences. In addition, cell handling modules may also utilize a downstream means for determining the presence or absence of cells. Suitable cell handling modules include, but are not limited to, cell lysis modules, cell removal modules, cell concentration modules, and cell separation or capture modules. In addition, as for all the modules of the invention, the cell handling module is in fluid communication via a flow channel with at least one other module of the invention.

In a preferred embodiment, the hydrogel attached to the SAW biosensor surface serves as an blood filtration unit where none of the blood cell can enter, but where all the different specific chemical species can enter the three dimensional structure of the hydrogel and find the particular molecular recognition sequence immobilized in the hydrogel.

In a preferred embodiment, the hydrogel also served as a way to reduce non-specific binding since not all molecules in the target sample can enter and or pass the hydrogel matrix. The entrance of the target molecule in the hydrogel highly depends on the pore size of the hydrogel. By changing the pore size it is possible to exclude some unwanted molecules that give rise to non-specific binding to the SAW sensor surface.

In a preferred embodiment, the cell handling module includes a cell lysis module. As is known in the art, cells may be lysed in a variety of ways, depending on the cell type. In one embodiment, as described in EP 0 637 998 B1 and U.S. Pat. No. 5,635,358, hereby incorporated by reference, the cell lysis module may comprise cell membrane piercing protrusions that extend from a surface of the cell handling module. As fluid is forced through the device, the cells are ruptured. Similarly, this may be accomplished using sharp edged particles trapped within the cell handling region. Alternatively, the cell lysis module can comprise a region of restricted cross-sectional dimension, which results in cell lysis upon pressure.

In a preferred embodiment, the cell lysis module comprises a cell lysing agent, such as detergents, NaOH, enzymes, proteinase K, guanidinium HCL, etc. In some embodiments, for example for blood cells, a simple dilution with water or buffer can result in hypotonic lysis. The lysis agent may be solution form, stored within the cell lysis module or in a storage module and pumped into the lysis module. Alternatively, the lysis agent may be in solid form that is taken up in solution upon introduction of the sample. Temperature or mixing may also be applied.

The cell lysis module may also include, either internally or externally, a filtering module for the removal of cellular debris as needed. This filter may be microfabricated between the cell lysis module and the subsequent module to enable the removal of the lysed cell membrane and other cellular debris components; examples of suitable filters are shown in EP 0 637 998 B1, incorporated by reference.

In one embodiment of sample preparation, cells are placed or distributed on a filter membrane evenly and a lysis buffer is passed through the cell layer on the filter membrane without mechanical homogenization of the cells. This can be performed in a sample preparation chamber as described above. Alternatively, it may be performed prior to addition of the sample to the chamber.

In the above, the cell lysate can be passed through the membrane of the filter plate with the aid of force generated by means of centrifugation, vacuum, or positive pressure. The filter or membrane of the filter plate includes, but is not limited to, glass fiber, polypropylene or polyolefine mesh, wool, and other membranes which have a pore size such that target cells can be trapped without any leakage of cells from the membrane, but cytosolic mRNA can pass through. For example, using glass fiber (Grade 934AH, Cambridge Technology, Inc. Watertown, Mass.) or Whatman GFIF grade glass fiber membrane, most of cultured cells and blood leukocyte can be trapped. In the above, glass fiber plates are preferable.

The lysis buffer may include a detergent for dissolving cell membranes, RNase inhibitor for inhibiting RNase activity or deactivating or destroying RNase, and pH control agent and salt for hybridization. The isolated target sample can then be analyzed as described herein Accordingly, a rapid, inexpensive, high throughput, and easily automated system can be realized.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population. These binding moieties may be immobilized either in the hydrogel matrix of the module or on a particle trapped within the module by physical absorption or by covalent attachment. Suitable binding moieties will depend on the cell type to be isolated or removed, and generally includes antibodies and other molecular recognition components, such as ligands for cell surface receptors, etc. Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size or shape. This can be done in a variety of ways, including protrusions from the surface that allow size exclusion, a series of narrowing channels, or a diafiltration type setup.

In a preferred embodiment, the cell handling module includes a cell removal module. This may be used when the sample contains cells that are not required in the assay. Generally, cell removal will be done on the basis of size exclusion as for "sieving", above, with channels exiting the cell handling module that are too small for the cells; filtration and centrifugation may also be done.

In a preferred embodiment, the cell handling module includes a cell concentration module. As will be appreciated by those in the art, this is done using "sieving" methods, for example to concentrate the cells from a large volume of sample fluid prior to lysis, or centrifugation.

In a preferred embodiment, the devices of the invention include a separation module. Separation in this context means that at least one component of the sample is separated from other components of the sample. This can comprise the separation or isolation of the target analyte, or the removal of contaminants that interfere with the analysis of the target analyte, depending on the assay.

In a preferred embodiment, the separation module includes chromatographic-type separation media such as absorptive phase materials, including, but not limited to reverse phase materials ($C_8$ or $C_{18}$ coated particles, etc.), ion-exchange materials, affinity chromatography materials such as binding ligands, etc. See U.S. Pat. No. 5,770,029.

In a preferred embodiment, the separation module utilizes binding ligands, as is generally outlined herein for cell separation or analyte detection.

When the sample component bound by the binding ligand is the target analyte, it may be released for detection purposes if necessary, using any number of known techniques, depending on the strength of the binding interaction, including changes in pH, salt concentration, temperature, etc. or the addition of competing ligands, etc.

In a preferred embodiment, the separation module includes an electrophoresis module, as is generally described in U.S. Pat. Nos. 5,770,029; 5,126,022; 5,631,337; 5,569,364; 5,750,015, and 5,135,627, all of which are hereby incorporated by reference. In electrophoresis, molecules are primarily separated by different electrophoretic mobilities caused by their different molecular size, shape and/or charge. Microcapillary tubes have recently been used for use in microcapillary gel electrophoresis (high performance capillary electrophoresis (HPCE)). One advantage of HPCE is that the heat resulting from the applied electric field is efficiently dissipated due to the high surface area, thus allowing fast separation. The electrophoresis module serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the electrophoresis module can take on a variety of forms, and generally comprises an electrophoretic microchannel and associated electrodes to apply an electric field to the electrophoretic microchannel. Waste fluid outlets and fluid reservoirs are present as required.

The electrodes comprise pairs of electrodes, either a single pair, or, as described in U.S. Pat. Nos. 5,126,022 and 5,750,015, a plurality of pairs. Single pairs generally have one electrode at each end of the electrophoretic pathway. Multiple electrode pairs may be used to precisely control the movement of sample components, such that the sample components may be continuously subjected to a plurality of electric fields either simultaneously or sequentially. Such a system is outlined in 5,858,195, incorporated herein by reference In a preferred embodiment, the devices of the invention include at least one fluid pump. Pumps generally fall into two categories: "on chip" and "off chip"; that is, the pumps (generally syringe pumps or electrode based pumps) can be contained within the device itself, or they can be contained on an apparatus into which the device fits, such that alignment occurs of the required flow channels to allow pumping of fluids.

In a preferred embodiment, the devices of the invention include at least one fluid valve that can control the flow of fluid into or out of a module of the device. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediately before the opening into a larger space such a chamber. In addition, as described in U.S. Pat. No. 5,858,195, incorporated herein by reference, a type of "virtual valve" can be used.

In a preferred embodiment, the devices of the invention include sealing ports, to allow the introduction of fluids, including samples, into any of the modules of the invention, with subsequent closure of the port to avoid the loss of the sample.

V. Applications

Once made, the device of the invention finds use in a variety of applications. Preferred applications include forensics, mutation detection, microorganism or pathogen detection and the like.

As to forensics, the identification of individuals at the level of DNA sequence variation offers a number of practical advantages over such conventional criteria as fingerprints, blood type, or physical characteristics. In contrast to most phenotypic markers, DNA analysis readily permits the deduction of relatedness between individuals such as is required in paternity testing. Genetic analysis has proven highly useful in bone marrow transplantation, where it is necessary to distinguish between closely related donor and recipient cells. Two types of probes are now in use for DNA fingerprinting by DNA blots. Polymorphic minisatellite DNA probes identify multiple DNA sequences, each present in variable forms in different individuals, thus generating patterns that are complex and highly variable between individuals. VNTR probes identify single sequences in the genome, but these sequences may be present in up to 30 different forms in the human population as distinguished by the size of the identified fragments. The probability that unrelated individuals will have identical hybridization patterns for multiple VNTR or minisatellite probes is very low. Much less tissue than that required for DNA blots, even single hairs, provides sufficient DNA for a PCR-based analysis of genetic markers. Also, partially degraded tissue may be used for analysis since only small DNA fragments are needed. Forensic DNA analyses will eventually be carried out with polymorphic DNA sequences that can be studied by simple automatable assays such as OLA. For example, the analysis of 22 separate gene sequences, each one present in two different forms in the population, could generate 1010 different outcomes, permitting the unique identification of human individuals. That is, the unique pattern of mass increases as a result of detecting unique genes, exon/intron boundaries, SNPs, mRNA and the like results in the unique identification of an individual.

In another preferred embodiment the device finds use in tumor diagnostics. The detection of viral or cellular oncogenes is another important field of application of nucleic acid diagnostics. Viral oncogenes (v-oncogenes) are transmitted by retroviruses while their cellular counterparts (c-oncogenes) are already present in normal cells. The cellular oncogenes can, however, be activated by specific modifications such s point mutations (as in the c-K-ras oncogene in bladder carcinoma and in colorectal tumors), promoter induction, gene amplification (as in the N-myc oncogene in the case of neuroblastoma) or the rearrangement of chromosomes (as in the translocation of the c-abl oncogene from chromosome 9 to chromosome 22 in the case of chronic myeloid leukemia). Each of the activation processes leads, in conjunction with additional degenerative processes, to an increased and uncontrolled cell growth. The so-called "recessive oncogenes" which must be inactivated for the fonmation of a tumor (as in the retinobiastoma (Rb gene and the osteosarcoma can also be detected with the help of DNA probes. Using probes against immunoglobulin genes and against T-cell receptor genes, the detection of B-cell lymphomas and lymphoblastic leukemia is possible. As such, the invention provides a method and device for diagnosing tumor types. Nucleic acid probes or antibodies directed to various tumor markers are used as bioactive agents for the detection of tumor markers.

An additional preferred embodiment the device finds use in transplantation analyses. The rejection reaction of transplanted tissue is decisively controlled by a specific class of histocompatibility antigens (HLA). They are expressed on the surface of antigen-presenting blood cells, e.g., macrophages. The complex between the HLA and the foreign antigen is recognized by T-helper cells through corresponding T-cell receptors on the cell surface. The interaction between HLA, antigen and T-cell receptor triggers a complex defense reaction which leads to a cascade-like immune response on the body. The recognition of different foreign antigens is mediated by variable, antigen-specific regions of the T-cell receptor-analogous to the antibody reaction. In a graft rejection, the T-cells expressing a specific T-cell receptor which fits to the foreign antigen, could therefore be eliminated from the T-cell pool. Such analyses are possible by the identification of antigen-specific variable DNA sequences which are amplified by PCR and hence selectively increased. The specific amplification reaction permits the single cell-specific identification of a specific T-cell receptor. Similar analyses are presently performed for the identification of auto-immune disease like juvenile diabetes, arteriosclerosis, multiple sclerosis, rheumatoid arthritis, or encephalomyelitis.

In an additional preferred embodiment the device finds use in genome diagnostics. Four percent of all newborns are born with genetic defects; of the 3,500 hereditary diseases described which are caused by the modification of only a single gene, the primary molecular defects are only known for about 400 of them. Hereditary diseases have long since been diagnosed by phenotypic analyses (anamneses, e.g., deficiency of blood: thalassemias), chromosome analyses (karyotype, e.g., mongolism: trisomy 21) or gene product analyses (modified proteins, e.g., phenylketonuria: deficiency of the phenylalanine hydroxylase enzyme resulting in enhanced levels of phenylpyruvic acid). The additional use of nucleic acid detection methods considerably increases the range of genome diagnostics.

In the case of certain genetic diseases, the modification of just one of the two alleles is sufficient for disease (dominantly transmitted monogenic defects); in many cases, both alleles must be modified (recessively transmitted monogenic defects). In a third type of genetic defect, the outbreak of the disease is not only determined by the gene modification but also by factors such as eating habits (in the case of diabetes or arteriosclerosis) or the lifestyle (in the case of cancer). Very frequently, these diseases occur in advanced age. Diseases such as schizophrenia, manic depression or epilepsy should also be mentioned in this context; it is under investigation if the outbreak of the disease in these cases is dependent upon environmental factors as well as on the modification of several genes in different chromosome locations. Using direct and indirect DNA analysis, the diagnosis of a series of genetic diseases has become possible: sickle-cell anemia, thalassemias, al-antitrypsin deficiency, Lesch-Nyhan syndrome, cystic fibrosis/mucoviscidosis, Duchenne/Becker muscular dystrophy, Alzheimer's disease, X-chromosome-dependent mental deficiency, Huntington's chorea.

In an additional preferred embodiment the device finds use in pharmacogenomics. Pharmacogenomics has evolved from the academic science into an important tool for drug research and development. Accordingly, a new paradigm has evolved to target drug to patients with a specific genetic profile that predicts a favorable response to therapy. Different genes expression level of specific SNP's into certain genes can be useful for the treatment of cancer, diabetes and cardiovascular disease. Those candidate genes can be used to profile patients and their disease to allow for optimal treatment based on the presence or absence of specific genetic polymorphisms. By focusing on loci that appear to predict the onset of disease, it is the hope that pharmaceutical companies will intervene with new compounds designed to halt the progression of disease.

When pharmacogenomics is integrated into drug research it allows pharmaceutical companies to stratify patient populations based on genetic background. During drug development, these same markers can be used to link efficacy or disease susceptibility to new pharmaceutical compounds. To be able to measure such changes in either single gene, many genes either as SNP or simple changes in expression level it requires a method as described to which may be utilized to overcome the challenges of modifying biological material such as DNA before measurement, enhance sample number throughput in a wide variety of based assays and overcome the used of highly specialized and expensive equipment.

In an additional preferred embodiment the device finds use in infectious disease. The application of recombinant DNA methods for diagnosis of infectious diseases has been most extensively explored for viral infections where current methods are cumbersome and results are delayed. In situ hybridization of tissues or cultured cells has made diagnosis of acute and chronic herpes infection possible. Fresh and fomalin-fixed tissues have been reported to be suitable for detection of papillomavirus in invasive cervical carcinoma and in the detection of HIV, while cultured cells have been used for the detection of cytomegalovirus and Epstein-Barr virus. The application of recombinant DNA methods to the diagnosis of microbial diseases has the potential to replace current microbial growth methods if cost-effectiveness, speed, and precision requirements can be met. Clinical situations where recombinant DNA procedures have begun to be applied include the identification of penicillin-resistant *Neisseria gonorrhea* by the presence of a transposon, the fastidiously growing chlamydia, microbes in foods; and simple means of following the spread of an infection through a population. The worldwide epidemiological challenge of diseases involving such parasites as leishmania and plasmodia is already being met by recombinant methods.

In an additional preferred embodiment the device finds use in gene expression analysis. One of the inventions disclosed herein is a high throughput method for measuring the expression of numerous genes (1-100) in a single measurement. The method also has the ability to be done in parallel with greater than one hundred samples per process. The method is applicable to drug screening, developmental biology, molecular medicine studies and the like. Thus, within one aspect of the invention methods are provided for analyzing the pattern of gene expression from a selected biological sample, comprising the steps of (a) exposing nucleic acids from a biological sample, (b) combining the exposed nucleic acids with one or more selected nucleic acid probes each located on a particular microsensor, under conditions and for a time sufficient for the probes to hybridize to the nucleic acids, wherein the hybridization correlative with a particular nucleic acid probe and detectable by the DNA-amplification-microsensor technology.

In additional preferred embodiments the device finds use in detection of micro-organisms, specific gene expression or specific sequences in nucleic acid. The use of DNA probes in combination with the DNA-amplification-microsensor technology can be used to detect the presence or absence of micro-organisms in any type of sample or specimen. Detectable nucleic acid can include mRNA, genomic DNA, plasmid DNA or RNA, rRNA viral DNA or RNA.

In an additional preferred embodiment the device finds use in mutation detection techniques. The detection of diseases is increasingly important in prevention and treatments. While multi factorial diseases are difficult to devise genetic tests for, more than 200 known human disorders are caused by a defect in a single gene, often a change of a single amino acid residue (Olsen, Biotechnology: An industry comes of age, National Academic Press, 1986). Many of these mutations result in an altered amino acid that causes a disease state.

Those point mutations are often called single-nucleotide polymorphisms (SNP) or cSNP when the point mutation are located in the coding region of a gene.

Sensitive mutation detection techniques offer extraordinary possibilities for mutation screening. For example, analyses may be performed even before the implantation of a fertilized egg (Holding and Monk, Lancet 3:532, 1989). Increasingly efficient genetic tests may also enable screening for oncogenic mutations in cells exfoliated from the respiratory tract or the bladder in connection with health checkups (Sidransky et al., Science 252:706, 1991). Also, when an unknown gene causes a genetic disease, methods to monitor DNA sequence variants are useful to study the inheritance of disease through genetic linkage analysis. However, detecting and diagnosing mutations in individual genes poses technological and economic challenges. Several different approaches have been pursued, but none are both efficient and inexpensive enough for truly widescale application.

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants, it is within that last described this invention has its strong advances compared to known status of the art technology.

Mutations are a single-base pair change in genomic DNA. Within the context of this invention, most such changes are readily detected by hybridization with oligonucleotides that are complementary to the sequence in question. In the system described here, two oligonucleotides are employed to detect a mutation. One oligonucleotide possesses the wild-type sequence and the other oligonucleotide possesses the mutant sequence. When the two oligonucleotides are used as probes on a wild-type target genomic sequence, the wild-type oligonucleotide will form a perfectly based paired structure and the mutant oligonucleotide sequence will form a duplex with a single base pair mismatch.

As discussed above, a 6 to 7° C. difference in the Tm of a wild type versus mismatched duplex permits the ready identification or discrimination of the two types of duplexes. To effect this discrimination, hybridization is performed at the Tm of the mismatched duplex in the respective hybotropic solution. The extent of hybridization is then measured for the set of oligonucleotide probes. When the ratio of the extent of hybridization of the wild-type probe to the mismatched probe is measured, a value to 10/1 to greater than 20/1 is obtained. These types of results permit the development of robust assays for mutation detection.

Other highly sensitive hybridization protocols may be used. The methods of the present invention enable one to readily assay for a nucleic acid containing a mutation suspected of being present in cells, samples, etc., i.e., a target nucleic acid. The "target nucleic acid" contains the nucleotide sequence of deoxyribonucleic acid (DNA) or ribonucleic acid (RNA) whose presence is of interest, and whose presence or absence is to be detected for in the hybridization assay. The hybridization methods of the present invention may also be applied to a complex biological mixture of nucleic acid (RNA and/or DNA). Such a complex biological mixture includes a wide range of eucaryotic and procaryotic cells, including protoplasts; and/or other biological materials which harbor polynucleotide nucleic acid. The method is thus applicable to tissue culture cells, animal cells, animal tissue, blood cells (e.g., reticulocytes, lymphocytes), plant cells, bacteria, yeasts, viruses, mycoplasmas, protozoa, fungi and the like. By detecting a specific hybridization between nucleic acid probes of a known source the specific presence of a target nucleic acid can be established.

An exemplary hybridization assay protocol for detecting a target nucleic acid in a complex population of nucleic acids is described as follows: A probe containing the SNP at the 3' end is immobilized in the hydrogel on one active microsensor at it's 5' end (probe 1). Within the surroundings of the first micro-sensor a second microsensor is immobilized with a probe having the wild type sequence (probe 2). Two primers are designed for PCR amplification of a PCR product containing the potential SNP site. Normally the probe sites are located close to one of the primer sites. The following events may occur simultaneously in the chamber: 1) DNA amplification of target nucleic acid molecule in solution using the two above primers 2) hybridization of amplified target nucleic acid molecule to the probe 1 and probe 2 immobilized on two different hydrogel matrixes (microsensors). The target nucleic acid molecules are capable of hybridizing to the 3' region of the immobilized probe sequence, to thereby form a hybridization complex that has a 3' terminus; 3) 3' extension of the DNA strand hybridized to the immobilized probe on the surface of the sensor to form a modified primer. If the DNA tested has the SNP site, probe 1 will hybridize more efficiently to the DNA compared to probe 2 where a 3' mismatch will inhibit the 3' extension reaction of the DNA strand hybridized to the immobilized probe in the hydrogel matrix. If the DNA tested does not contain SNP site (wild type), probe 2 will hybridize more efficiently to the DNA compared to probe 1 where a 3' mismatch will inhibit the 3' extension reaction of the DNA strand hybridized to the immobilized probe on the surface of the sensor. Those observations can be directly observed due to the frequency differences between the output signals of each microsensor, or the different frequency shifts between the input and output signal of each sensor.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

In an additional preferred embodiment the device finds use in vitro diagnosis of allergic (type I; type II; type III and type IV). A predominant task of the human immune system is to distinguish between endogenous and exogenous substances and, where appropriate, initiate destruction of the exogenous substances. The progress in the development of immunological methods in the past has repeatedly revealed novel diagnostic and therapeutic possibilities. Thus, for example, highly specific monoclonal antibodies are used as detectors for pathogenic viruses, bacteria and parasites or for detecting pathological cellular alterations. It has additionally been found recently that numerous chronic disorders are attributable to a pathological reaction of the immune system. In so-called autoimmune diseases such as myasthenia, rheumatoid arthritis or else juvenile diabetes, the immune response is directed against endogenous cells and substances. Also to be categorized as pathological are the cases where the body initiates an excessive immune response as a result of contact with an exogenous substance. These hypersensitivities, referred to as allergies, to substances which are innocuous per se, may induce cutaneous and mucosal swelling over the whole body or, in serious cases, life-threatening reactions in conjunction with an anaphylactic shock.

Elucidation of the individual immunological functional processes, especially the diagnosis of the specific reaction of the individual patient to particular allergens, represents a task, which is, especially in recent times, becoming increasingly important in medicine.

A large number of very disparate processes are known for detecting allergic reactions: Thus, for example, blood samples are routinely taken. After the blood samples have been taken they are deprived of nutrients and rapidly die. With suitable staining methods and immunohistological labeling methods it is possible to draw conclusions, from morphological changes and from the detection of particular antigens, about certain allergic reactions. These histopathological methods do not, however, permit any conclusions about the substances, which induce an immediate allergic reaction (called a type I reaction). Likewise, no statements about the current functioning of the immune cells are possible. Essentially two different test methods are employed for diagnosing these type I allergies today; "the skin test" and "the blood test" for measuring the total and specific amount of IgE; IgG and IgA.

The most widely used are the skin test methods. These entail extracts of suspected allergens being introduced into the skin by either scratching or pricking, or they are placed on the skin. The locally stimulated allergic reaction is then manifested as reddening and swelling of the affected area of skin. The skin test is difficult to perform uniform each time and the result is sometime depended on the physician that performs the test. It can produce false-positive/negative reactions and there is also a chance for adverse systemic reactions (anaphylaxis). Moreover, the skin test is difficult to perform on children and/or persons with skin eruptions. The skin test cannot be performed during the patient's symptomatic days. Some people react with swelling by scratches and for this reason will react on all allergens tested. On those people it is not possible to use the skin test at all, because the action when making a prick in the skin will provoke a swelling and will not be due to an allergic reaction. For these reasons, the scientific community have for sometime recommended that the skin test is replaced with a blood test with is the other method used for type one allergy testing.

Today most physicians use the skin test as an aid to point out IgE antibodies. To make a comprehensive diagnosis, anamneses and a blood sample are taken for further analysis, it is possible to test for more than 100 different allergens, however as a routine and standard test only 10 allergens are tested. A blood test today is performed in medium to large laboratories. Pharmacia Diagnostic offers instrumentation and reagents to perform the blood test based on the ELISA technique. Serum from the blood sample is sent to a local or regional testing laboratory running a Pharmacia UniCAP system. The UniCAP 100 system processes up to 48 tests with a maximum of 4 different methods in a single run, which take 3 hours. For IgE mediated allergy the following test are necessary to perform on the UniCAP system: Step 1: To distinguish between atopic and non-atopic disease (atopic allergy is Asthma, Hay Fever and Eczema). Step 2: Next test is to measure total IgE in a blood sample, which provide valuable information about the total allergy load and/or overview of the patient's atopic status. Step 3: To make an exact diagnosis it is required to determine the specific IgE's that are the cause of the allergic reaction. Total and specific antibodies responsible for allergy can be measured by in vitro methods such as radioallergosorbent test (RAST) or ELISA test. By using the surface acoustic wave sensors technology immobilized with a particular allergen in the hydrogel it is possible to perform a specific allergy (type 1) test within 5-30 minutes compare to the today exciting methods like the ELISA test and other label based technologies.

In a preferred embodiment the microsensor can be used for determining the presence or absence of a target allergen in a test sample comprising: contacting a specific target IgE molecule in blood or serum or plasma with the microsensor comprising a hydrogel surface having an immobilized allergen which hybridised to the specific target IgE molecule to form a hybridisation complex; applying an input signal to an input transducer to generate a surface acoustic wave within the surface acoustic wave sensor; receiving the surface acoustic wave at an output transducer; generating an electronic output signal; and measuring a parameter of the output signal which provides an indication of whether or not the specific target IgE molecule is present in the test sample.

In a preferred embodiment the microsensor can be used for determining the presence or absence of a target allergen in a test sample comprising: contacting a specific air born target IgE molecule with the microsensor comprising a hydrogel surface having an immobilized allergen which hybridised to the specific target IgE molecule to form a hybridisation complex; applying an input signal to an input transducer to generate a surface acoustic wave within the surface acoustic wave sensor; receiving the surface acoustic wave at an output transducer; generating an electronic output signal; and measuring a parameter of the output signal which provides an indication of whether or not the specific target IgE molecule is present in the test sample.

In a preferred embodiment the microsensor can be used for determining the presence or absence of a total IgE in a test sample comprising: contacting total target IgE molecules in blood or serum or plasma with a microsensor comprising a hydrogel surface having an immobilized anti-IgE molecules which hybridised to the total target IgE molecule to form a hybridisation complex; applying an input signal to an input transducer to generate a surface acoustic wave within the surface acoustic wave sensor; receiving the surface acoustic wave at an output transducer; generating an electronic output signal; and measuring a parameter of the output signal which provides an indication of whether or not the total target IgE molecule is present in the test sample.

In a preferred embodiment the microsensor can be used for specific determining the presence or absence of a antigen where the following specific allergen is selected as molecular recognition component from the group consisting of but limited to: Foods; Abalone, Allspice, Almond, Anise, alpha-lactalbumin, Anchovy, Anise, Apple, Apricot, Asparagus, Aubergine, Avocado, Bamboo shoot, Banana, Barley, Basil, Bay leaf, Beef, Beetroot, beta-lactoglobulin, Blackberry, Black pepper, Black current, Blue berry, Blue vetch, Blue mussel, Bovine lactoferrin, Brazil nut, Broccoli, Brussel sprouts, Buckwheat, Cabbage, Carambola, Caraway, Cardamon, Carob, Carrot, Casein, Cashew nut, Cauliflower, Celery, Cheese (Camembert), Cheese (Cheddar), Cheese (Edam), Cheese (Goats), Cheese (Gouda), Cheese, (Mould), Cheese (Parmisan), Cheese (Roquefort), Cherry, Chestnut, sweet, Chick pea, Chicken meat, Chilipepper, Chub mackerel, Cinnamon, Clam, Clove, Cochinal extract (*Dactylophus coccus*), Cocoa, Coconut, Cod fish, Coffee, Conalbumin, Common millet, Corn (Maize), Coriander, Cows milk, Cows milk (boiled), Crab, Cranberry, Crayfish, Cucumber, Curry (Santa Maria), Date, Dill, Duck, Egg, Egg white, Egg yolk, Eel, Elk meat/Moose meat, Fennel seed, Fennel fresh, Fenugreek, Fig, Foxtail millet, Garlic, Ginger, Gluten, Goats milk, Grape, Grapefruit, Green bean, Green pepper, Guar (*Cyamopsis tet*- ragonolobus), Guava, Gum Arabic, Hake, Halibut fish, Hazel nut, Herring, Honey, Hop (fruit cone), Horse meat, Jack fruit, Jack mackerel (*Trachurus japonicus*), Japanese millet, Jujube, Kiwi fruit, Langust, Lamb/mutton, Lemon, Lentil, Lettuce, Lime, Linseed, Litchi, Lobster (*Homarus gammarus*), Lovage, Lupine seed, Macadamia nut, Mace, Mackerel (*Scomber scombrus*), Maize, Malt, Mandarin, Mango fruit, Mare's milk, Marjoram, Megrim, Melon, Milk, Milk (boiled), Milk-powder (Alfare, Nestle), Mint, Mushroom, Mustard, Mutton, Nutmeg, Oat, Octopus, Olive (black fresh, *Olea europaea*), Onion, Orange, Oregano, Ovalbumin, Ovomucoid, Oyster, Pacific squid, Papaya, Paprika, Parsley, Passion fruit, Pea, Peach, Peanut, Pear, Pecan nut, Persimon (*Diospyros kaki*), Pine nut, Pineapple, Pistacio nut, Plaice, Plum, Poppy seed, Pork, Potato (*Solanbum tubersome*), Pumpkin, Pumpkin seed, Quinoa, Rabbit meat, Rape seed, Raspberry, Red current, Red kidney bean, Rice, Rose hip, Rye, Saffron, Sage, Salmon, Sardine (*Sardinops melanosticta*), Sardine (*Sardinia pilchardus*), Scallop, Sesame seed, Sheep milk, Sheep whey, Shrimp, Snail, Sole, Soyabean, Spinach, Squid (*Loligo* spp), Strawberry, Sunflower seed, Sugar-beet seed, Swordfish, Sweet potato (*Ipomea batatas*), Tarragon, Tea, Thyme, Tomato, Tragacanth, Trout fish, Tuna fish, Turkey meat, Vanilla, Walnut, Watermelon, Wheat, Whey (liquid product after milk forms curds), White bean, Wine (red), Wine (white), Yeast, Yoghurt, Animal Dander & Epithelia; BSA (bovine serum albumin), Budgerigar droppings, Budgerigar feathers, Budgerigar serum protein, Canary feathers, Cat dander, Cat serum albumin, Chicken droppings, Chicken feathers, Chicken serum proteins, Chinchilla epithelium, Cow dander, Deer epithelium, Dog dander, Dog epithelium, Dog serum albumin, Duck feathers, Ferret epithelium (*Putorius putorius*), Finch feathers, Fox epithelium, Gerbil epithelium, Goat epithelium, Goose feathers, Guinea pig epithelium, Hamster epithelium, Horse dander, Horse serum proteins, Mink epithelium, Mouse, Mouse epithelium, Mouse urine proteins, Mouse serum proteins, Parrot feathers, Pigeon droppings, Pigeon feathers, Rabbit epithelium, Rabbit serum proteins, Rabbit urine proteins, Rat, Rat epithelium, Rat urine proteins, Rat serum proteins, Reinder epithelium, Sheep epithelium, Swine epithelium, Swine serum albumin, Swine urine proteins, Turkey feathers, TREE POLLEN; Acacia, American beech, Australian pine, Birch, Box elder, Cedar, Chestnut, Common silver birch, Cottonwood, Date, Douglas fir, Eldertree, Elm, *Eucalyptus* spp., Grey alder, Hazel, Horn beam, Horse chestnut, Italian cypress (*Cupressus sempervirens*), Japanese cedar, Linden (*Tilia cordata*), London plane, Melaleuca (Cajeput-tree), Mesquite, Mountain juniper, Mulberry, Oak, Olive, Paloverde, Pecan, Pepper tree, Pine, Privet (*Ligustrum vulgare*), Queen palm, Spruce, Sweet gum, Virginia live oak, Walnut, Willow, White ash, White pine, Tree Pollen (Recombinant); Bet v 1 Birch Pollen (Recombinant), Bet v 2 profilin Birch Pollen (Recombinant), Bet v 4 Birch Pollen (Recombinant), Weeds; Camomile, Cocklebur, Common pigweed, Common ragweed, Dandelion, English plantain (Ribwort), False ragweed, Firebush, Gigant ragweed, Golden rod, Goosfoot (Lamb's quarters), Lupin, Marguerite, Mugwort, Nettle, *Parietaria officinalis*, Plantain, Rape, Rough inarshelder, Saltwort (Russian thistle), Scale (Lenscale), Sheep sorrel, Sugar-beet, Sunflower, Wall pellitory (*Parietaria officinalis*), Wall pellitory (*Parietaria judacia*), Western ragweed, Wormwood, Grass Pollen; Bahia grass (*Paspalum notatum*), Barley (*Hordeum vulgare*), Bermuda grass (*Cynodon dactylon*), Brome grass (*Bromus inermis*), Canary grass (*Phalaris arundinacea*), Cocksfoot (*Dactylis glomerata*), Common reed (*Phragmites communis*), False Oat grass (*Arrhenaatherum elatius*), Johnson grass (*Sorghum halepense*), Maize/Corn (*Zea mays*), Meadow fescue (*Festuca elatior*), Meadow foxtail (*Alopecurus pratensis*), Meadow grass (*Poa pratensis*), Oat-Cultivated (*Avena sativa*), Perennial Rye, Redtop, Bentgrass (*Agrostis stonlonifera*), Rye-Cultivated (*Secale cereale*), Rye-Grass (*Lolium perenne*), Salt grass (*Distichlis spicata*), Sweet vernal (*Anthoxanthum odoratum*), Timothy grass (*Phleum pratense*), Velvet grass (*Holcus lanatus*), Wheat-Cultivated (*Tricum sativum*), Wild Rye grass (*Elymus triticoides*), Grass Pollen (Recombinant and purified native); rPhl p 1 Timothy pollen (Recombinant), rPhl p 2 Timothy pollen (Recombinant), rPhl p 4 Timothy pollen (Native), rPhl p 5 Timothy pollen (Recombinant), rPhl p 6 Timothy pollen (Recombinant), rPhl p 7 Timothy pollen (Recombinant), rPhl p II Timothy pollen (Recombinant), rPhl p 12 profilin Timothy pollen (Recombinant), Moulds; *Altenaria alternata* (*A. tenuis*), *Aspergillus fumigates*, *Aspergillus niger*, *Aureobasidium pullulans*, *Botrytis cinerea*, *Candida albicans* (yeast), *Cephalosporium acremonium*, *Chaetomimum globosum*, *Cladosporium herbarum*, *Curvularia lunata*, *Epicoccum purpurascens*, *Fusarium moniliforme*, *Helminthosporium halodes*, *Mucor racemosus*, *Penicillium frequentans*, *Penicillium notatum*, *Phoma betae*, *Pityrosporum orbiculare*, *Rhizopus nigricans*, Staphylococcal enterotoxin, Staphylococcal enterotoxin A, Staphylococcal enterotoxin B. Staphylococcal enterotoxin C, Staphylococcal enterotoxin D, *Stemphylium botryosum*, *Trichoderma viride*, *Trichophyton*, ment. var interdigitale, *Trichophyton*,ment. var qoetzii, *Trichophyton rubrum*, *Trichosporon pullulans*, *Ulocladium chartarum*, *Ustilago nuda/tritici*, Moulds (Recombinant); rASP f 1 *Aspergillus* (Recombinant), rASP f 2 *Aspergillus* (Recombinant), rASP f3 *Aspergillus* (Recombinant), rASP f4 *Aspergillus* (Recombinant), rASP f6 *Aspergillus* (Recombinant), Insects and Venoms; Berlin beetle, Blood worm, Bumblebee, Cockroach (*Blatella germanica*), Cockroach (*Blatella orientalis*), Cockroach (*Periplaneta Americana*), European Hornet, Fire Ant, Grain weevil, Green nimitti, Honey bee, Horse fly (*Tabanus* spp.), Horse bot fly (*Gasterophilus intestinalis*), Mediterranean flour mith, *Mosquito* spp., Moth, *Polistes* spp. (Paper wasp), *Vespula* spp (Common wasp, Yellow jacket), Wasp, White Faced Hornet, Yellow hornet, House Dust; Greer Labs. Inc., Hollister-Stier Labs, Dust Mites: Domestic; *Blomia tropicalis*, *Dermatophagoides farinae*, *Dermatophagoides microceras*, *Dermatophagoides pteronyssinus*, *Euroglyphus maynei*, Dust Mites: Storage; *Acarus Siro*, *Glycophagus domesticus*, *Lepidoglyphus destructor*, *Tyrophagus putrescentiae*, Parasites; *Anisakis*, *Ascaris*, *Echinococcus*, Occupationals, Chemicals; Abachi wood dust, Alkalase, Alpha-amylase, *Bougainvillea* spp., Bromelin, Castor bean, Cotton seed, Chloramin T, Ethyle oxide, *Ficus* spp., Formaldehyde/Formalin, Green coffee bean, Hexahydrophtalic anhydride, Histamine, Isocyanate HDI, Isocyanate MDI, Isocyanate TDI, Ispaghula, Latex, Lysozyme, Maleic anhydride, Maxatase, Methyltetrahydrophtalic anhydride, Papain, Pepsin, Phospholipase, Phthalic anhydride, Savinase, Silk-Natural, Silk-Waste, Sunflower seed, Trimellitic Anhydride (TMA), Drugs; ACTH (Adrenocorticotrophic hormone), Amoxycillin, Ampicillin, Cefaclor, Chymopapain, Insulin Bovine, Insulin Human, Insulin Porcine, Pencillin G, Penicillin V, Protamine, Suxamethonium (Succinylcholine), Tetanus toxoid, Miscellaneous; *Artemisia salina* (fish feed), Crude cotton, Duphina (fish feed), Mealworm (*Tenebrio molitor*), Tetramin (fish food), Tobacco leaf, Seminal fluid.

In a preferred embodiment the microsensor can be used for detecting waterborne pathogens such as *E. coli* O157:H7 and *listeria* and *Salmonella*.

In a preferred embodiment the microsensor can be used as sensor unit in a handheld instrument for a bio warfare detection system.

VII. Alternative Biosensors

The present invention is not limit to the use of SAW. Technologies such as Cantilevers or surface plasmon resonance (SPR) can be used in combination with hydrogels that undergoes a conformation changes when bind a target analyte.

In an exemplary embodiment a biosensor for detecting the presence of a chemical species in a solution, comprising: cantilever sensor having a hydrogel attached to the sensor surface; the hydrogel having pendant moieties that are charged under measuring conditions; the hydrogel having molecular recognition component immobilized in the hydrogel structure capable of detecting the chemical species; the cantilever sensor capable of detecting a volume, dimensional, or conformational change in the hydrogel due to the free chemical species binding to the molecular recognition component immobilized in the hydrogel.

In a preferred embodiment any biosensor are described wherein the hydrogel that undergoes a volume, dimensional, or conformational change in response to the chemical species. When the volume, conformation, or dimension of the hydrogel changes, changes of the cantilever sensor surface; comparing the change measurements to determine the presence of the chemical species, wherein the changes is caused by the contact of the chemical species with the molecular recognition component and wherein the changes correlates with the presence of the chemical species.

In a preferred embodiment a biosensor for detecting the presence of a chemical species in a solution, comprising: surface plasmon resonance (SPR) sensor having a hydrogel disposed on the sensor surface; the hydrogel having pendant moieties that are charged under measuring conditions; the hydrogel having molecular recognition component immobilized in the hydrogel structure capable of detecting the chemical species; the SPR sensor capable of detecting a volume, dimensional, or conformational change of the hydrogel due to the free chemical species binding to the molecular recognition component immobilized in the hydrogel.

In a preferred embodiment a biosensor is described wherein the hydrogel undergoes a volume, dimension, or conformational change in response to the chemical species. When the volume, dimension, or conformation of the hydrogel changes, the SPR sensor surface changes. The changes following exposure to the solution are measured. The changes determine the presence of the target analyte.

Different types of target analytes can be detected, including chemicals, gases in solution, analytes corresponding to the presence of various medical conditions, biological molecules, and analytes important in the field of medical diagnostics.

Some polymers reversibly change conformation in response to a specific external stimulus. For example, almost all polymers undergo some reversible conformational change with changes in solvents, and some, such as poly N-isopropylacrylamide, undergo conformational changes in response to temperature changes. Solutes that interact with the side groups on the polymer backbone may also induce conformational changes; introduction of ionized groups onto the backbone of the polymer thus sensitizes the polymer conformation to changes in ionic strength. Polymers that change conformation in response to the concentration of a single, specific solute can therefore be prepared by adding to that polymer a functional group that selectively interacts with that single solute. Such polymers can be further mixed with crosslinking agents to form gels that exhibit the same response to stimuli as the polymer from which they are formed. For example, these gels can undergo volume changes at conditions when the constituent polymer chains change conformation. Volume changes between 0.1 and 50%, or even greater, are contemplated by the present invention.

In another aspect, the present invention is directed to a sensor device comprising: a hydrogel characterized by the property of undergoing a volume change in response to a specific chemical species. The hydrogel in one embodiment of the present invention generally comprises a crosslinking agent, a gel component and a molecular recognition component. The crosslinking agent can be any crosslinking agent compatible with the other components of the hydrogel. Examples of suitable crosslinkers include N,N'-methylenebisacrylamide, methylenebismethacrylamide and ethyleneglycoldimethacrylate, with N,N'methylenebisacrylamide being preferred. In addition to forming the polymer network in the CCA, the cross-linking agent as used in this step assists formation of the hydrogel and strengthens the resulting hydrogel so that a self-supporting film results. Hydrogels can be formed when as little as 1 part in 100 parts by weight of the monomer mixture is the cross-linking agent. Generally, increasing the amount of crosslinking agent lowers the sensitivity of the gel to the analyte being detected. Preferably, crosslinker is used in an amount between about 4 and 15% of monomer weight, more preferably about 5% of monomer weight.

The phase transition properties of the hydrogel are modified by functionalizing the hydrogel with a reagent that specifically binds a target analyte. Thus the gel is modified so as to detect the presence of a stimulus by means of this molecular recognition component. More specifically, a monomer capable of selectively interacting with a specific solute is incorporated in the hydrogel. Typically, the more molecular recognition component present, the more sensitive the device to the desired analyte. This relationship, however, is only observed up to a certain concentration of the molecular recognition component, after which the sensitivity of the gel decreases. Any monomer having molecular recognition capabilities for the desired solute can be used.

When the analyte binds to the gel matrix, it causes a change in the hydrophilicity of the matrix, and therefore changes the swelling properties of the gel. As the hydrogel shrinks and swells, the CCA embedded in the hydrogel follows.

In addition, a third monomer component can be added to change the sensitivity of the device by making the hydrogel even more hydrophobic or hydrophilic, as desired by the needs of the user. The more hydrophobic the gel, the more it tends to stay in a collapsed or shrunken state. For example, an acrylamide, which is more hydrophilic than NIPA, can be added, or N-butylacrylamide, which is more hydrophobic than NIPA, can be added to adjust the properties of the hydrogel.

A method for making a device according to the present invention generally comprises the steps of allowing charged particles to self assemble into a crystalline colloidal array; adding a first comonomer that is a gel monomer, a crosslinking agent, a second comonomer that is a molecular recognition monomer to a medium comprising the crystalline colloidal array and a polymerization initiator; and polymerizing the mixture to form a crystalline colloidal array embedded in a hydrogel.

An alternative method for making a device according to the present invention generally comprises the steps of allowing charged particles to self assemble into a crystalline colloidal array; adding a crosslinking agent, a gel monomer, and a polymerization initiator; polymerizing the mixture to form a crystalline colloidal array embedded in a hydrogel; and adding a molecular recognition component capable of binding with the hydrogel.

Any suitable particles can be used. For example, the particles used to create the CCA can be colloidal polystyrene, polymethylmethacrylate, silicon dioxide, aluminum oxide, polytetrafluoroethylene or any other suitable materials which are generally uniform in size and surface charge. Colloidal polystyrene is preferred. The particles are chosen depending upon the optimum degree of ordering and the resulting lattice spacing desired for the particular application. The particles preferably have a diameter between about 50 and 500 nanometers and may be either synthesized as discussed below or obtained commercially.

Monodisperse particle colloids can be prepared by emulsion polymerization or any other means. For example, an emulsion polymer colloid can be prepared by mixing the desired monomer with a cross-linking agent, a surfactant to aid in the formation of the emulsion, a buffer to keep the pH of the solution constant and to prevent particle coagulation, and a free-radical initiator to initiate polymerization. In a preferred embodiment, the monomer is styrene, the crosslinking agent is divinylbenzene, the surfactant is sodium-di(1,3-dimethylbutyl)sulfosuccinate, the initiator is preferably potassium persulfate and an ionic comonomer is also added, preferably 1-sodium, 1-allyloxy-2-hydroxypropane sulfonate. Other suitable compounds can also be used to prepare the emulsion polymer colloid, so long as compatibility problems do not arise. The particles should then be purified by the use of centrifugation, dialysis and/or an ion exchange resin. Purification of the commercially available particles is also required.

Following polymerization, the particles may be stored in an ion exchange resin, preferably in a bath of 10% by weight suspension of ion exchange resin such as analytical grade AG51X8 mixed bed resin commercially available from Biorad of Richmond, Calif. The ion exchange resin should preferably be cleaned prior to use through a suitable procedure such as that of Vanderhoff et al. in the Journal of Colloid and Interface Science, Vol. 28, pp. 336-337 (1968).

The electrically charged particles are then allowed to self assemble to form a crystalline colloidal array. This assembly takes place in a suitable solvent, preferably water. To the CCA medium is then added a gel monomer, a molecular recognition monomer, a cross-linking agent and a polymerization initiator. Any suitable initiator can be used, such as a thermal initiator or a photoinitiator. Preferably, a UV photoinitiator is used. A preferred UV photoinitiator for this use is 2,2'-diethoxyacetophenone. Any cross-linking agent, gel monomer and molecular recognition monomer discussed above can be used.

After formation, the mixture is then polymerized. Any means known in the art can be used to initiate polymerization, so long as the method for polymerization does not destroy or otherwise disorder the CCA. Preferably, the polymerization is accomplished by placing the mixture between two plates, preferably quartz plates separated by a parafilm spacer, at a temperature from between about 0° to 10° C. The plates are then exposed to UV light. Exposure to the UV light effects complete polymerization after about 5 minutes. Upon completion of the polymerization, the plates are removed and a stable polymerized CCA (PCCA) results. This film can be approximately about 150 microns (0,15 mm) thick and can be made thinner based upon the needs of the user.

The response rate of the hydrogel as the preferred embodiment, having a thickness of about 150 microns, is typically less than about 5 minutes. Response rate can be improved by decreasing the thickness of the hydrogel. The response rate is partially determined by the mass transport of cations into the gel, and partially determined by the kinetics of complexation. Decreasing the gel thickness and the monomer content of the gel will markedly increase the rate of analyte mass transport to the active sites on the gel, and therefore decrease response time. Response rate will also be affected by the molecular recognition component used, as some will be more selective than others. Response rates of between about 1 and 5 minutes can be achieved with a 150 micrometer thick gel and response rates on the order of seconds can be achieved with thinner gels. The response rate is inversely proportional to the thickness of the gel.

In another embodiment of the present invention, the hydrogel in which the CCA is polymerized comprises a crosslinking agent, a gel monomer and a biomolecular recognition component. This biomolecular recognition component is a biomolecule that selectively binds a specific chemical specie as part of its biological function. This component can be bound to the gel directly or by one or more linking molecules. Examples of such biomolecular recognition components include but are not limited to enzymes, antibodies, antigens, porphyrins, ferritin, or pheromone receptors. These natural recognition components can respond to simple chemical species, or to the presence of particular proteins. These sensor devices can therefore further comprise one or more linking molecules that bind the biomolecular recognition component to the gel monomer. In addition, the biomolecular recognition component can be modified by being reacted with a molecule that can be bound to the linking agent, or to the gel itself. A particularly preferred linking molecule is 5-(biotinamido) pentylamine, and a preferred molecule for reaction with the biomolecular recognition component is avidin; avidin is a protein extracted from egg whites and has four binding sites for biotin. The sensor devices of this embodiment have particular application in the area of detection of disease markers, for example in detecting the presence of Troponin I antibodies. The gel can be sensitive to very low concentrations of species, if the recognition element has a high binding constant.

For example, an antigen can be added to a gel monomer to form a hydrogel that binds such things as antibodies to Troponin I, Troponin T, tuberculosis cells, cancer cells. The antigen is chosen based on what medical condition is to be detected. Enzymes can also be attached to the gel for medical diagnostics. For example, binding glucose oxidase to the hydrogel will allow for the detection of glucose. Thus this embodiment of the present invention has application as a medical diagnostic tool. As above, the sensitivity of the sensor can be adjusted to the desired concentration by modifying the ratio of gel monomer to recognition component, the degree of crosslinking and the hydrophobicity of the gel monomer. Hydrophobicity can be adjusted as discussed above with the addition of another monomer that is either more or less hydrophobic than the gel monomer, depending on the needs of the user.

The antibody and antigen based sensors function much the same way as the chemical sensors discussed above.

In the case of the enzyme based sensors, the enzyme changes the chemical nature of the analyte by first binding to the analyte substrate and then cleaving or otherwise reacting with the analyte substrate. The gel of the enzyme based sensors swells because the interior of the gel has a high concentration of reaction products and a low concentration of analyte substrate, while the liquid surrounding the gel has the opposite characteristics. This causes an osmotic pressure imbalance between the inside and outside of the gel. A solvent, preferably water, diffuses into the gel to relieve that pressure imbalance; it is this excess solvent that causes the gel to swell. If immersed in a fresh solution of the substrate, the sensor will expand again. The response of the sensor, therefore, is dependent upon the concentration and amount of substrate in its immediate environment.

In yet another embodiment of the present invention, interpenetrating networks (IPNs) can be used to produce hydrogel with recognition elements that are normally incompatible with the required self assembly of the CCA prior to polymerization into a PCCA. For example, some molecular recognition functionalized comonomers may be ionic, and would screen the electrostatic colloidal particle repulsive interactions required for CCA self assembly. In this case, the sensor is made in two steps. First, a loosely crosslinked PCCA is formed without the molecular recognition element. Following formation of this PCCA, the functionalized monomer having the recognition element is diffused into the existing PCCA network. A second polymerization is then effected, wherein the polymer chains of the second network will form an interpenetrating network within the voids of the first network. The second network of the IPN will shrink or swell in response to the presence of the analyte, and the PCCA will expand or contract along with the second network due to the physical entanglement of the two networks.

The present invention is also directed to sensors that do not utilize electrostatic interactions for volume changes, but instead utilize the non-ionic volume phase transition phenomenology of NIPA-like hydrogels.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

The following non-limiting examples serve to more fully describe the manner of using the above-described invention. It is understood that these examples in no way serve to limit the scope of this invention, but rather are presented for illustrative purposes.

Example I

Short Description of the Single Components in the Instrument Setup.

SAW sensor design: A special design and constructed 610 MHz SAW Resonator Oscillator was constructed as illustrated at FIG. 10; FIG. 11 and FIG. 12. The interdigital gold electrodes was constructed on a piezoelectric support comprises lithium tantalite. The spacing between the interdigital gold electrodes is approx. 1 micrometer (FIG. 12) Each SAW sensor was coated with 50 nm of $SiO_2$ for electric insulation and chemical attachments purposes. As illustrated at FIG. 12 the thin layer of $SIO_2$ can be seen.

Figure 6:
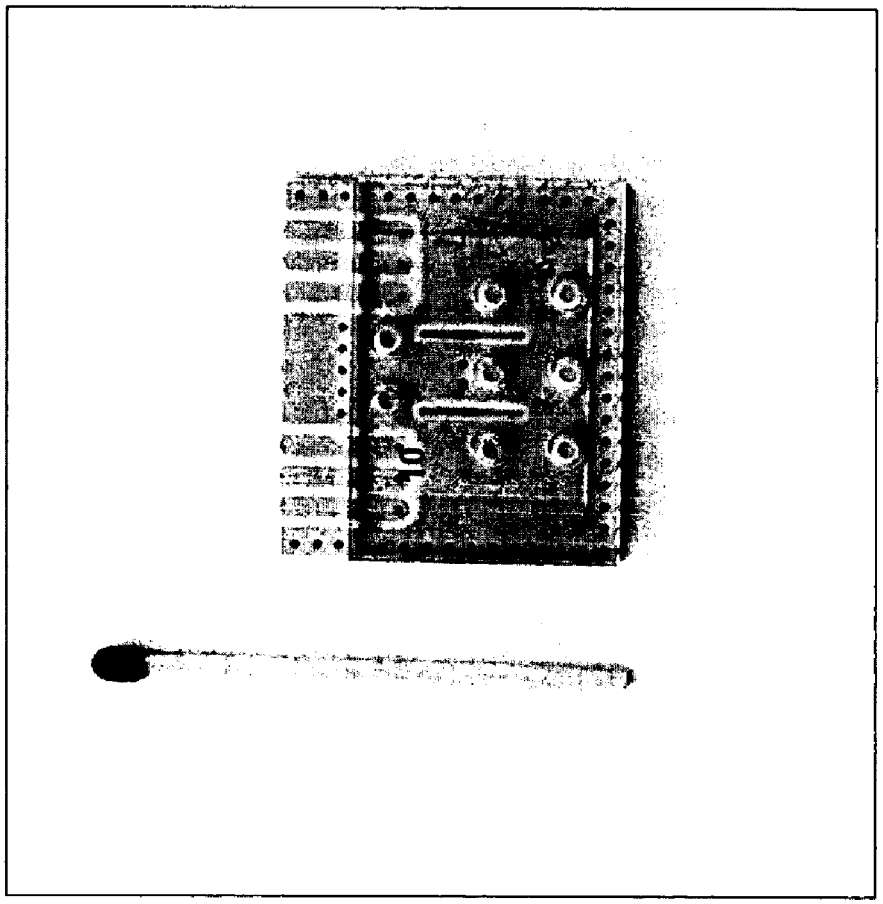

Cartridge design: Two SAW sensors were assembled in a special cartridge as illustrated on FIG. 5 to FIG. 9. The cartridge consist of a special design print card where the two SAW sensors where attached using standard flip chip technology (FIG. 5 to FIG. 8). All electric connections from the two SAW sensors were constructed as illustrated in FIG. 5 and FIG. 6). Two special modified PMMA blocks was attached to each side of the print card to generate a flow channel connecting the two SAW sensors as illustrated at FIG. 8. This cartridge constriction makes is possible to both perform flow experiment and non-flow experiments.

Electronic design: Each SAW sensor was operated by the electronics illustrated at FIG. 13. The output of each SAW sensor circuit was connected to a two-channel frequency counter HP (Agilent) 53131A. Alternative special design electronics was constructed to bypass the frequency counter.

Software: Using the frequency counter HP (Agilent) 53131A, a special program that measures the difference between the SAW sensor (sensing) and the SAW sensor (reference) was constructed in the software VEE from Agilent. A curve illustrating the time on X-axis and delta frequency on Y-axis was displayed. Alternative either company made software or the LabVIEW software from National Instruments was used. The difference in signal between the two SAW sensors are recorded in the following way:

Delta frequency=SAW sensor(reference)–SAW sensor (sensing)

Example II

Modification of the Empty Surface Acoustic Wave Sensor Surface Using Double Stranded Lambda DNA.

The purpose of this example is to demonstrate the effect on binding a 10.000 ds-DNA molecule to the surface acoustic wave sensor surface.

SAW sensor cleaning: Any $SiO_2$ surface that has been removed from its vacuum deposition chamber really cannot be considered clean, unless some effort has been made to clean it. The extreme sensitivity of the microsensor system demands that all measurements be performed under conditions that closely control the binding of materials to and the removal of materials from the SAW sensor surface. It is critical to clean the SAW sensor surface to minimize signal interference because contaminants that can randomly attach to or come off of the SAW surface will interfere with the intended signal. A solution of 0.1 M NaOH and 1% Triton X-100 was injected into the cartridge to effectively removes small amounts of surface contamination. The cartridge was rinse in water afterwards.

Sulfhydryl-silylation of the $SiO_2$ surface: A 95% ethanol/5% water solution is adjusted to pH 5.0 with acetic acid. 3(mercaptopropyl)trimethoxy silane solution are added with stirring to yield a 2% final concentration. The solution should be stirred for five minutes to allow for hydrolysis and silanol formation. Each SAW sensor is contacted with this solution in five minutes. The SAW sensor are rinsed in ethanol and left for cure over night at room temperature.

Figure 2:
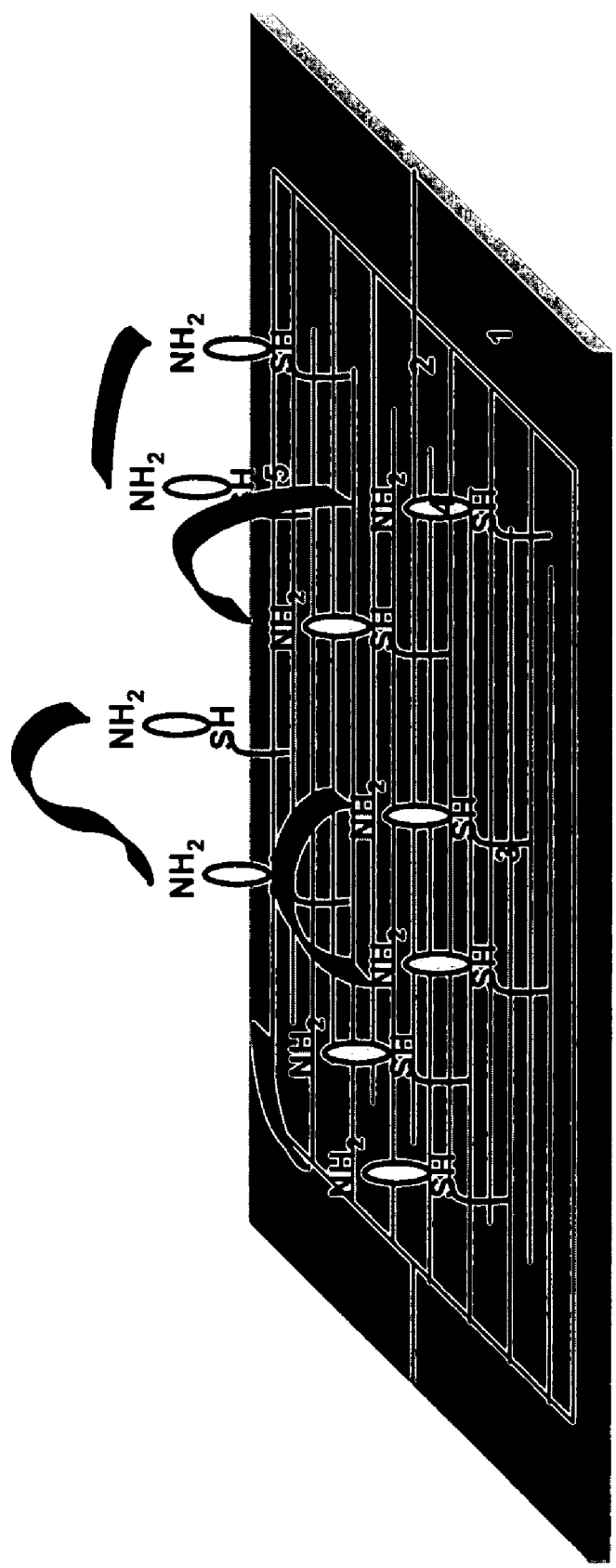
FIG. 2A depicts a schematic drawing of the SAW sensor surface having a molecular recognition component bound to the thin layer of $SiO_2$ on the SAW surface via coupling of amino groups located in each and of the DNA molecule to the cross linker molecule GMBS. (1) The SAW sensor surface; (2) The gold IDT on the surface; (3) 3(mercaptopropyl)trimethoxy silane; (4) GMBS crosslinker; (5) the molecular recognition agent crosslinked to the SAW surface via the amino groups.
FIG. 2B depicts a schematic drawing of the SAW sensor surface having a 10.000 bp DNA molecules bound to the thin layer of $SiO_2$ on the SAW surface via coupling of amino groups located in each and of the DNA molecule to the cross linker molecule GMBS. At the FIGURE the 10.000 bp DNA molecule (5) have been cut with the restriction enzyme BgI, this particular enzyme cut several internal locations in the DNA fragments.
Figure 2:
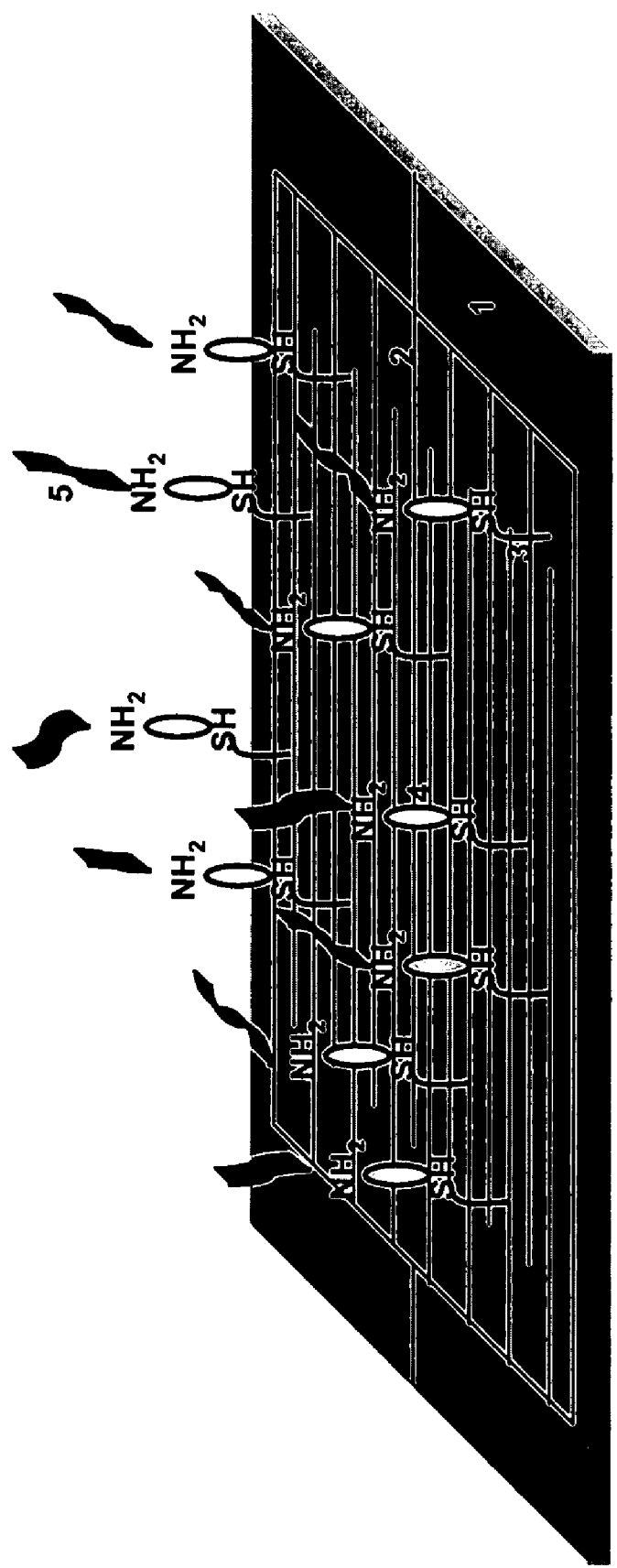

GMBS attachment to the free —SH groups: For binding free amino groups on DNA molecule, the amino and sulfhydryl reactive cross linker molecule GMBS are attach to the free surface bound sulfhydryl groups. The sensing SAW sensor was contacted with 10 mM GMBS in 1× couplings buffer (5× couplings buffer; 100 mM Hepes, 750 mM NaCl, 50 mM EDTA pH 7.1) in 90 minutes. The sensing SAW sensor are rinsed in water and left for cure over night at room temperature. The construction is illustrated at FIG. 2A. The molecular recognition agent in this case is the DNA molecule.

A 10.000 bp double stranded lambda DNA fragment having both ends modified with an amino-group was constructed using the PCR process with the 5'amino modified primers: amino-5'-ATA TAC CGA AGA GGC GCA GA-3' (SEQ ID NO:1) and "mangler".

The lambda DNA fragment has 13 BglI internal site. The DNA fragment was after PCR amplification purified using a Qiagen PCR purification kit. The concentration of the DNA fragment was adjusted to 0.1 ug/ml.

The 10.000 bp DNA fragment was injected into the cartridge contracting both SAW sensors. After 1 hour a changes in delta frequency of >500.000 Hz was observed.

A mixture of the restriction enzyme BgII in standard concentration was injected into the cartridge for contacting the two SAW sensors. This enzyme cuts the DNA fragment 13 different internal location as illustrated at FIG. 2B. After one hour the delta frequency signal between the two SAW sensors was back to baseline leverage as illustrated at table 1.

TABLE I

|  | Delta frequency at experimental start | Delta frequency after injecting the 10.000 bp DNA fragments. | Delta frequency after injecting the Bgl restriction enzyme mixture. |
|---|---|---|---|
| Delta frequency signal | Stable baseline signal | >+500.000 Hz | Back to baseline leverage |

Example III

Modification of the Empty Surface Acoustic Wave Sensor Surface Using Polymerized Acrylamide Attached to the Surface Via an Oligonucleotide Acryldite Link.

Identical procedures as EXAMPLE II for cleaning, attachment of Sulfhydryl-silylation and attachment of the cross linker molecule GMBS to the SAW sensor surface.

A special design 25 bases oligonucleotide having an internal HinP1 I site, an acrylamide-group (Acrydite) in the 5'end and an amino group in the 3'end was purchase from Integrated DNA Tech Company.

The oligonucleotide was injected into the cartridge contacting only the sensing SAW sensor and incubated in 90 minutes at room temperature. The SAW sensor surface was rinsed in water and air-dried.

A Solution (2×10 ul) of a copolymerization mixture containing 5% (w/v) acrylamide/bisacrylamide monomers, UV initiator (2,2'-diethoxyacetophenone) in PBS buffer was overlaid the two SAW sensor through the two injections inlet in the cartridge as illustrated at FIG. 3A.

The two SAW sensors were exposed to UV light and at the same time the delta frequency signal was detected.

As indicated at table II the delta frequency was highly influence by the polyacrylamide photo polymerization process.

TABLE II

|  | Delta frequency at experimental start | Delta frequency after the polyacrylamide photo polymerization process | Delta frequency after injecting the HinP1 I restriction enzyme mixture. |
|---|---|---|---|
| Delta frequency signal | Stable baseline signal | >+500.000 Hz | Back to baseline leverage |

A mixture (2×10 ul) of the restriction enzyme HinP1I in standard concentration was overlaid the two SAW sensors. The restriction enzyme cut in the primer so the polyacrylamide anchor gets released from the SAW sensor surface as illustrated at FIG. 3B. After one hour the delta signal between the two SAW sensors was back to baseline leverage as illustrated at table II.

Example IV

Modification of the Empty Surface Acoustic Wave Sensor Surface Using Polymerized Acrylamide Attached to the Surface Via an Antibody/Antigen Link.

As illustrated at FIG. 4A the SAW sensing sensor surface are attached with a specific antibody via an amino group attachment to the GMBS cross linker molecule. A metacrylic-modified antigen are hybridised to the surface attached antibody. A film of polyacrylamide where the all ready bound metacrylic-modified antigen are taken part of the polymerization process are placed on top of the SAW sensor as illustrated in FIG. 4A. Any free antigen analyte will compete with the bound metacrylic-modified antigen, and thereby relishing the polyacrylamide film from the SAW sensor surface as illustrated at FIG. 4B. This release will result in a delta frequency shift, and thereby an indication of the presence of the particular specific antigen.

The antigen against the analyte are metacrylic-modified after the following procedure essential as described in "A. Yu. Rubina et al; BioTechniques 2003, Vol 34, No 5, page 1009". Protein solution (100 uL at 20 uM in 0.01 M borate buffer, pH 9.3, was mixed with 29 uL of a 0.1-10 mM solution of N-hydroxysuccinimide ester of 6-methacrylaminohexanoic acid in dimethyl formamide (DMF), and the mixture was stirred from ½ to 2 hours a room temperature. The protein: modifier molar ration was varied from 1:1 to 1:100. The modified protein were purified on a micro bio-spin column with sephadex G25 or used for copolymerization in the reaction mixture without purification. The number of methacrylic groups introduced into the antigen was determined by MALDI mass spectra.

Example V

Theoretic Example

Modification of the Empty Surface Acoustic Wave Sensor Surface Using a Photonic Crystal Sensing Motif Attached to the Surface Via Arylamide/Silane Containing Molecule.

This example is a theoretic example on how an SAW sensor could function using a polymerized crystalline colloidal array.

A special design molecule (in the following named: attaching molecule) having an acrylamide group (Acrydite) in one end and an silane-group in the opposite end should be designed.

The attaching molecule are injected into the cartridge contacting the SAW sensor surfaces covered with $SiO_2$ and incubated in x minutes at room temperature. The attaching molecule will bind to the $SiO_2$ surface via the silane group. The SAW sensor surfaces was rinsed in detergent and air-dried.

A Solution of a copolymerization mixture containing highly charged monodisperse polystyrene colloids, acrylamide/bisacrylamide monomers, UV initiator (2,2'-diethoxyacetophenone) and the metacrylic-modified antibody was overlaid the sensing SAW sensor surface through the injections inlet giving access to the sensing SAW sensor surface.

A Solution of a copolymerization mixture containing highly charged monodisperse polystyrene colloids, acrylamide/bisacrylamide monomers, UV initiator (2,2'-diethoxyacetophenone) but not the metacrylic-modified antibodyadded was overlaid the reference SAW sensor surface through the injections inlet giving access to the reference SAW sensor surface.

Figure 1A:
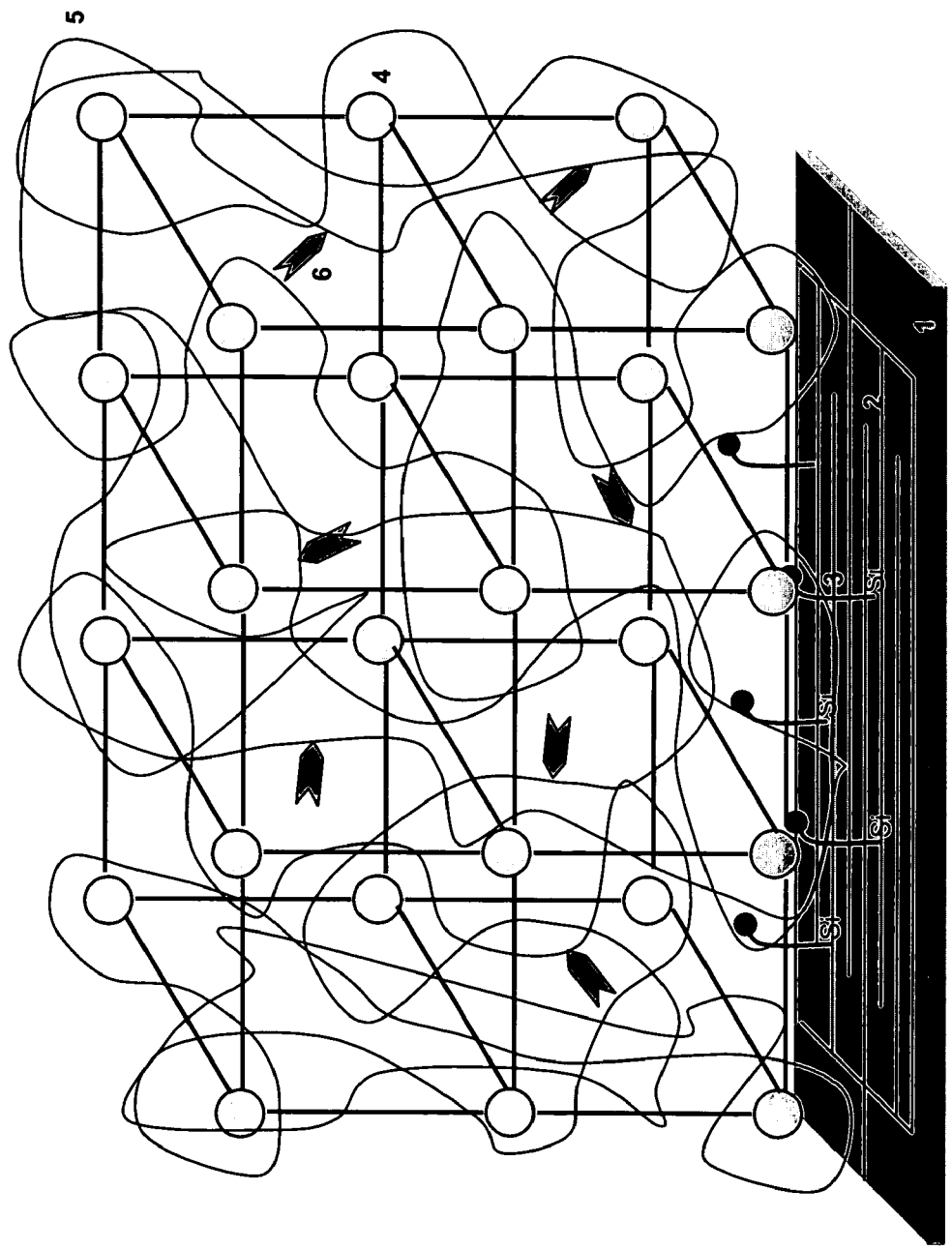
FIG. 1A depicts a schematic drawing of the SAW sensor surface having attached the thin three dimensional film structure comprising a crystalline colloidal array of charged particles polymerized in a hydrogel including a molecular recognition component. (1) The SAW sensor surface; (2) The gold IDT on the surface; (3) The anchored molecules having a silane group in one end and an acrylamide group in the opposite end; (4) The colloidal charged particles; (5) The polymerized acrylamide net; (6) The molecular recognition component.
Figure 1:
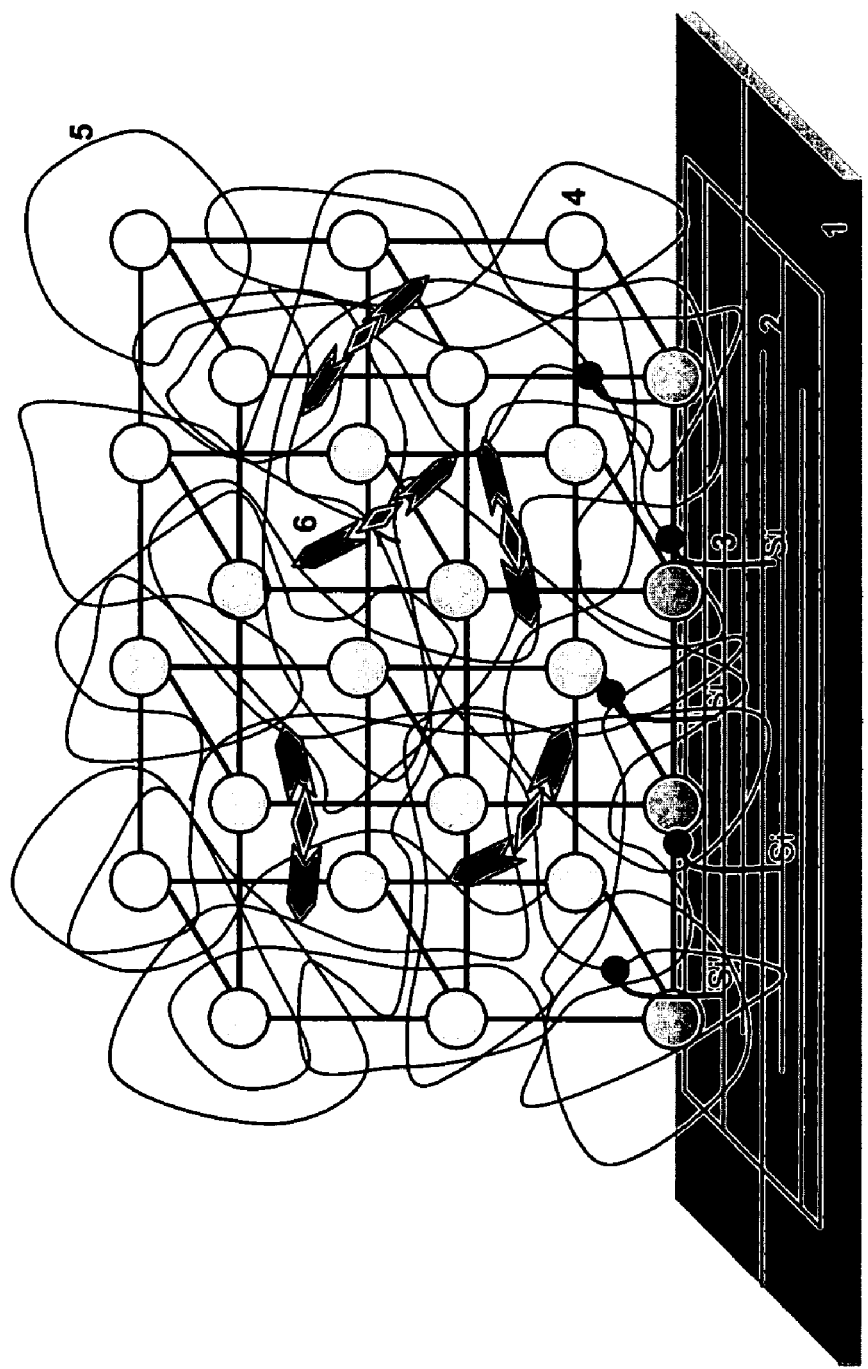
FIG. 1B depicts a schematic drawing of the SAW sensor surface having attached a hydrogel including a crystalline colloidal array of charged particles.

The sensing surface is illustrated in FIG. 1A.

The two SAW sensor surfaces were photo polymerization by exposed to UV light.

By adding the specific antigen on top of the two SAW sensors the antigen will diffuse into the hydrogel matrix and bind to the immobilized antibody as illustrated in FIG. 1B. This event will give rice to a conformations changes of the hydrogel whereby effecting the sensing SAW sensor.

This conformation changes will result in a large delta frequency shift, and thereby an indication of the presence of the particular antigen.

Example VI

Water Effect (Damping) on One SAW Senser.

A simple measurement was performed one SAW with and without water present. As illustrated at FIG. 14 almost no damping effect was seen after injecting water into the cartridge.

Results and Discussion

Example I illustrated the set-up of a full operational SAW based detection instrument. Example II and Example III demonstrated that the interdigital gold electrodes on the surface of the elastic layer are under highly influence of surface modification such as DNA cross linking between the electrodes or overlaid the electrodes with a polyacrylamide film. In Example VI and V theoretic examples shows how those features can be used for constructing a sensor unit based on the modification of the interdigital electrodes. In example VI its was show the excellent performance of the SAW sensor under water.

Example VII

Measuring Low Among of Protein A from *Staphylococcus Areus*.

This example describes how to build up a SAW resonator sensor unit including: applying hydrogel matrix and or antibody solution on sensor surface, polymerising the hydrogel matrix and or antibody solution and interaction between the antibody/hydrogel matrix and antigen (protein A) at a concentration of 8 pg/ml protein A in PBS buffer.

A sensor unit consist of two SAW resonators, one served as reference (without detecting antibody) and one served at sensing sensor (with detecting antibody) as illustrated in FIG. 15.

The two SAW resonators that makes up a sensor unit are oscillating at 610 MHz and are electronically assembled on a special gold coated substrate using flip chip technology as illustrated at FIG. 15.

The sensor unit are build up in two separated steps:

Step 1: Applying the hydrogel/antibody matrix to the sensor unit.

Step 2: The detection step between the polymerised antibody/hydrogel matrix and the antigen (in this example protein A).

In step 1 the difference solutions are added directly to the sensor surfaces.

In step 2 the sensor unit are assemble in a flow system and the analyte are injected over the two sensor surfaces at a flow speed of 25 ul/min.

Step 1: Applying the Antibody/Hydrogel Matrix to the Sensor Unit.

Preparation of acrylated Goat polyclonal antibody to Protein A (ab7243, abcam): Add 100 ul antibody solution (conc.: 1 mg/ml) to a eppendorf tube.

Add further 90 ul PBS and 10 ul of a N-Acryloxysuccinimide solution (conc. 1 ug/ml).

Incubate 1 hour at 37 C.

Ready for use, store at 4 C.

Preparation of 0.25% photoinitiator solution: Add 1.0 gram of Irgacure 2959 (Ciba Specially Chemicals) to 400 ml PBS buffer (standard).

Heat up to 80-90 C under steering until the photoinitiator is dissolved.

Store at 4 C.

Preparation of hydrogel solution: Add 100 ul Poly(ethylene glycol)diacrylate (Aldrich 437441) to 9.9 ml standard PBS buffer.

Mix 8.0 ml of above solution with 2.0 ml of 0.25% photoinitiator solution, the hydrogel solution is now ready for use.

Preparation of an antibody/hydrogel solution: Mix 80 ul of hydrogel solution with 20 ul of acrylated Goat polyclonal antibody to Protein A (conc. 500 ug/ml), final concentration of antibody 100 ug/ml, this solution are named "antibody/hydrogel solution".

Mix 80 ul of hydrogel solution with 20 ul of PBS, this solution is named "hydrogel solution".

Add 4 ul of the antibody/hydrogel solution to the sensing SAW resonator (FIG. 15 (1)).

Add 4 ul of the hydrogel solution to the reference SAW resonator (FIG. 15 (2)).

Incubate the sensor unit for 200 seconds.

Switch on a 365 nm UV light source for 200 seconds (Vilber Lourmat M03 5950).

Wash each SAW resonator three times with PBS buffer by pipetting 3×4 ul up/down in over the two SAW resonator surfaces in the sensor unit.

FIG. 21 depicts the antibody/hydrogel solution applied to the sensing SAW resonator indicated by the arrow. As can be seen the frequency are decreasing approx. 250.000 Hz. This is believed to be due to absorption of the antibody/hydrogel solution to the SAW resonator structures. The polymerisation reaction are illustrated for the antibody/hydrogel solution. The 365 nm UV light source are started at time 0 seconds. As can be illustrated a characteristic frequency drop of approx. 150.000 are observed after approx. 80 seconds. It is believed this is due to the major part of the polymerisation reaction of the antibody/hydrogel solution between the IDT's structures.

Step 2: The Detection Step Between the Polymerised Antibody/Hydrogel Matrix and the Antigen (In This Example Protein A).

1. Preparation of a Protein A solution (conc. 8 pg/ml): Dissolve 5 mg of Protein A 2. (Sigma P60319) in 5 ml of PBS buffer.

3. Add 2 ul of the above solution to 998 ul PBS buffer.

4. Add 2 ul of the above solution to 998 ul PBS buffer.

5. Add 2 ul of the above solution to 998 ul PBS buffer.

6. The final conc. is 8 pg/ml of Protein A in PBS buffer.

The sensor unit are assembled in a flow system as illustrated at FIG. 15 and a flow of PBS buffer is initiated at a flow speed of 25 ul/ml. After stable baseline are obtained the analyte (protein A) are injected at a conc. of 8 pg/ml over the sensor surface.

FIG. 18 depicts the IDTs including the antibody/hydrogel matrix are illustrated. FIG. 19 the interactions with the analyte (Protein A) are illustrated. It is believe that both the directly interaction (mass loading) between the antibody and analyte but also the changes of hydrogel structure upon antibody/analyte interaction are the reason for the very sensitive frequency response at very low analyte concentration.

FIG. 22 illustrates the response of protein A over the two SAW resonator surfaces. In the left Y axis the real frequency response can be observed. In the right Y axis the differential frequency response between the two SAW resonators can be observed. The time on the X axis is in seconds. Protein A sample are injected after approx. 230 seconds.

All publications, patents, and patent applications cited herein are hereby incorporated by reference in their entirety for all purposes to the same extent as if each individual publication, patent, or patent application were specifically and individually indicated to be so incorporated by reference.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the disclosure.

I claim:

1. A microsensor for detecting the presence of a target analyte in a test sample solution comprising a surface acoustic wave sensor comprising a hydrogel located on a surface of said sensor and at least one molecular recognition component immobilized within said hydrogel that is capable of detecting said target analyte, wherein the hydrogel comprises an array of charged colloidal particles within the hydrogel.

2. The microsensor according to claim 1, wherein a dimensional and or volume change of said hydrogel occurs when the target analyte binds to the molecular recognition component.

3. The microsensor according to claim 1, wherein two different molecular recognition components are capable of binding a single target analyte.

4. The microsensor according to claim 1, wherein the hydrogel comprises vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides; amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N, N'-methylenebisacrylamide, methylenebismethacrylamide ethyleneglycol- dimethacrylate, N, N'-methylenebisacrylamide, polyethyleneglycoldiacrylate(PEGDA), polyethyleneglycoldimethacrylate(PEGDMA), polyethyleneglycoldiacrylate(PEGDA), polyethyleneglycoldimethacrylate(PEGDMA), poly(vinyliden fluoride)(PVdF) based polymer, a polyacrylonitrile(PAN) based polymer, a polymethylmethacrylate(PMMA) based polymer, a polyvinyl chloride(PVC) based polymer, and a mixture of the poly(vinyliden fluoride)(PVdF) based polymer, polyacrylonitrile (PAN) based polymer, polymethylmethacrylate(PMMA) based polymer, and polyvinyl hloride(PVC) based polymer, or mixtures thereof.

5. The microsensor according to claim 4, further comprising a cross linking agent wherein the cross linking agent comprises N,N'- methylenebisacrylamide, methylenebismethacrylamide ethyleneglycol-dimethacrylate or agent N, N'- methylenebisacrylamide.

6. The microsensor according to claim 1, wherein said surface acoustic wave sensor is a surface acoustic wave resonator.

7. The microsensor according to claim 1, wherein the charged colloidal particles comprise polystyrene, polymethylmethacrylate, silicon dioxide, aluminum oxide, polytetrafluoroethylene or poly N-isopropylacrylamide.

8. The microsensor according to claim 1, further comprising a reference surface acoustic wave sensor comprising a reference hydrogel located on a surface of said reference sensor, wherein said reference hydrogel does not contain said molecular recognition component and wherein said microsensor is capable of subtracting the signal of said reference sensor from the signal of said sensor.

9. The microsensor according to claim 1, wherein the molecular recognition component is selected from the group consisting of nucleic acids, nucleotide, nucleoside, nucleic acids analogues such as PNA and LNA molecules, proteins, peptides, antibodies including IgA, IgG, IgM, IgE, enzymes, enzymes cofactors, enzyme substrates, enzymes inhibitors, membrane receptors, kinases, Protein A, Poly U, Poly A, Poly lysine, triazine dye, boronic acid, thiol, heparin, membrane receptors, polysaccharides, coomassie blue, azure A, metal-binding peptides, sugar, carbohydrate, chelating agents, prokaryotic cells or eukaryotic cells.

10. The microsensor according to claim 1, wherein the hydrogel comprises a polymerized monomer or hydrogel, a cross linking agent and optionally a chemical or UV-light activated inducer agent.

11. The microsensor according to claim 1, wherein the hydrogel comprises acrylamide, purified agarose, N-vinylpyrolidone, methacrylate, N-isopropylacrylamide, substituted acrylamide or poly(ethylene glycol) diacrylate (PEG-DA).

12. A microsensor for detecting the presence of a target analyte in a test sample solution comprising a surface acoustic wave sensor comprising a hydrogel located on a surface of said sensor and at least one molecular recognition component immobilized within said hydrogel that is capable of detecting said target analyte, wherein said surface of said sensor comprises interdigitated electrodes having channels between said electrodes and wherein said channels contain all or part of said hydrogel.

13. A handheld device for detecting target analytes comprising the microsensor of claim 1 or 12.

14. The microsensor of claim 13 wherein said channels have a height of 10 nm to 1 micron.

15. The microsensor of claim 14 wherein said channels have a width of 100 nm to 10 microns.

16. The microsensor according to claim 13, wherein a dimensional and or volume change of said hydrogel occurs when the target analyte binds to the molecular recognition component.

17. The microsensor according to claim 13, wherein two different molecular recognition components are capable of binding a single target analyte.

18. The microsensor according to claim 13, wherein the hydrogel comprises vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N, N'-methylenebisacrylamide, methylenebismethacrylamide ethyleneglycol-dimethacrylate, N, N'-methylenebisacrylamide, polyethyleneglycoldiacrylate(PEGDA), polyethyleneg lycoldimethacrylate(PEGDMA), polyethyleneglycoldiacrylate(PEGDA), polyethyleneglycoldimethacrylate(PEGDMA), poly(vinyliden fluoride)(PVdF) based polymer, a polyacrylonitrile(PAN) based polymer, a polymethylmethacrylate(PMMA) based polymer, a polyvinyl chloride(PVC) based polymer, and a mixture of the poly(vinyliden fluoride)(PVdF) based polymer, polyacrylonitrile (PAN) based polymer, polymethylmethacrylate(PMMA) based polymer, and polyvinyl hloride(PVC) based polymer; or mixtures therof.

19. The microsensor according to claim 18, further comprising a cross linking agent wherein the cross. linking agent comprises N, N'-methylenebisacrylamide, methylenebismethacrylamide ethyleneglycol-dimethacrylate or agent N, N'-methylenebisacrylamide.

20. The microsensor according to claim 13, wherein said surface acoustic wave sensor is a surface acoustic wave resonator.

21. The microsensor of claim 13 wherein said hydrogel further comprises an array of charged colloidal particles within the hydrogel.

22. The microsensor according to claim 21 wherein the charged colloidal particles comprise polystyrene, polymethylmethacrylate, silicon dioxide, aluminum oxide, polytetrafluoroethylene or poly N-isopropylacrylamide.

23. The microsensor according to claim 13, further comprising a reference surface acoustic wave sensor comprising a reference hydrogel located on-a surface of said reference sensor, wherein said reference hydrogel does not contain said molecular recognition component and wherein said microsensor is capable of subtracting the signal of said reference sensor from the signal of said sensor.

24. The microsensor of claim 23 wherein the surface of said reference acoustic wave sensor comprises interdigitated electrodes having channels between said electrodes and wherein said channels contain all or part of said hydrogel.

25. The microsensor according to claim 13, wherein the molecular recognition component is selected from the group consisting of nucleic acids, nucleotide, nucleoside, nucleic acids analogues such as PNA and LNA molecules, proteins, peptides, antibodies including IgA, IgG, IgM, IgE, enzymes, enzymes cofactors, enzyme substrates, enzymes inhibitors, membrane receptors, kinases, Protein A, Poly U, Poly A, Poly lysine, triazine dye, boronic acid, thiol, heparin, membrane receptors, polysaccharides, coomassie blue, azure A, metal-binding peptides, sugar, carbohydrate, chelating agents, prokaryotic cells or eukaryotic cells.

26. The microsensor according to claim 13, wherein the hydrogel comprises a polymerized monomer or hydrogel, a cross linking agent and optionally a chemical or UV-light activated inducer agent.

27. The microsensor according to claim 13, wherein the hydrogel comprises acrylamide, purified agarose, N-vinylpyrolidone, methaaylate, N-isopropylacrylamide, substituted acrylamide or poly(ethylene glycol) diacrylate (PEG-DA).

* * * * *

UNITED STATES PATENT AND TRADEMARK OFFICE
CERTIFICATE OF CORRECTION

PATENT NO. : 7,473,551 B2
APPLICATION NO. : 11/134821
DATED : January 6, 2009
INVENTOR(S) : Peter Warthoe It is certified that error appears in the above-identified patent and that said Letters Patent is hereby corrected as shown below:

Claim 4, Column 49, Line 50,

Please delete "anhydrides;"

and replace with

-- anhydrides, --

Claim 4, Column 49, Lines 56 – 61,

Please delete "N,N'-meth-ylenebisacrylamide, polyethyleneglycoldiacrylate(PEGDA), polyethyleneglycoldimethacrylate(PEGDMA), polyethyleneglycoldiacrylate(PEGDA), polyethyleneglycoldimethacrylate(PEGDMA), poly(vinyliden fluoride)(PVdF) based polymer,"

and replace with

-- N,N'-meth-ylenebisacrylamide, polyethyleneglycoldiacrylate(PEGDA), polyethyleneglycoldimethacrylate(PEGDMA), poly(vinyliden fluoride)(PVdF) based polymer, --

Claim 4, Column 49, Line 66,

Please delete "polyvinyl hloride(PVC)"

and replace with

-- polyvinylchloride(PVC) --

Signed and Sealed this

Tenth Day of August, 2010

David J. Kappos
*Director of the United States Patent and Trademark Office*

Claim 9, Column 50, Lines 42 – 44,

Please delete "membrane receptors, kinases, Protein A, Poly U, Poly A, Polylysine, triazine dye, boronic acid, thiol, heparin, membrane receptors, polysaccharides,"

and replace with

-- membrane receptors, kinases, Protein A, Poly U, Poly A, Polylysine, triazine dye, boronic acid, thiol, heparin, polysaccharides, --

Claim 14, Column 50, Line 66,

Please delete "claim 13 wherein"

and replace with

-- claim 12, wherein --

Claim 16, Column 51, Line 3,

Please delete "claim 13, wherein"

and replace with

-- claim 12, wherein --

Claim 17, Column 51, Line 7,

Please delete "claim 13, wherein"

and replace with

-- claim 12, wherein --

Claim 18, Column 51, Line 10,

Please delete "claim 13, wherein"

and replace with

-- claim 12, wherein --

Claim 18, Column 51, Lines 21 – 26,

Please delete "N,N'-meth-ylenebisacrylamide, polyethyleneglycoldiacrylate(PEGDA), polyethyleneglycoldimethacrylate(PEGDMA), polyethyleneglycoldiacrylate(PEGDA), polyethyleneglycoldimethacrylate(PEGDMA), poly(vinyliden fluoride)(PVdF) based polymer,"

and replace with

-- N,N'-meth-ylenebisacrylamide, polyethyleneglycoldiacrylate(PEGDA), polyethyleneglycoldimethacrylate(PEGDMA), poly(vinyliden fluoride)(PVdF) based polymer, --

Claim 18, Column 51, Line 31,

Please delete "polyvinyl hloride(PVC)"

and replace with

-- polyvinylchloride(PVC) --

Claim 19, Column 51, Line 34,

Please delete "the cross. linking agent"

and replace with

-- the cross linking agent --

Claim 20, Column 51, Line 38,

Please delete "claim 13, wherein"

and replace with

-- claim 12, wherein --

CERTIFICATE OF CORRECTION (continued)
U.S. Pat. No. 7,473,551 B2

Claim 21, Column 52, Line 1,

Please delete "claim 13 wherein"

and replace with

-- claim 12, wherein --

Claim 23, Column 52, Line 8,

Please delete "claim 13, wherein"

and replace with

-- claim 12, wherein --

Claim 23, Column 52, Line 10,

Please delete "located on-a surface"

and replace with

-- located on a surface --

Claim 25, Column 52, Line 20,

Please delete "claim 13, wherein"

and replace with

-- claim 12, wherein --

Claim 25, Column 52, Lines 26 – 28,

Please delete "membrane receptors, kinases, Protein A, Poly U, Poly A, Polylysine, triazine dye, boronic acid, thiol, heparin, membrane receptors, polysaccharides,"

and replace with

-- membrane receptors, kinases, Protein A, Poly U, Poly A, Polylysine, triazine dye, boronic acid, thiol, heparin, polysaccharides, --

Claim 26, Column 52, Line 31,

Please delete "claim 13, wherein"

and replace with

-- claim 12, wherein --

Claim 27, Column 52, Line 35,

Please delete "claim 13, wherein"

and replace with

-- claim 12, wherein --

Claim 27, Column 52, Lines 36 – 37,

Please delete "N-vinylpyrolidone, methaaylate, N-isopropylacrylamide,"

and replace with

-- N-vinylpyrolidone, methacrylate, N-isopropylacrylamide, --